United States Patent
Weeks et al.

(10) Patent No.: US 11,712,157 B2
(45) Date of Patent: Aug. 1, 2023

(54) SYSTEM AND METHOD FOR ENDOSCOPIC IMAGING AND ANALYSES

(71) Applicant: PacificMD Biotech, LLC, Henderson, NV (US)

(72) Inventors: Brian Hunter Weeks, San Diego, CA (US); Ashley Sikand, Las Vegas, NV (US); Jetmir Palushi, Irvine, CA (US)

(73) Assignee: PACIFICMD BIOTECH, LLC, Henderson, NV (US)

( * ) Notice: Subject to any disclaimer, the term of this patent is extended or adjusted under 35 U.S.C. 154(b) by 0 days.

(21) Appl. No.: 17/669,952

(22) Filed: Feb. 11, 2022

(65) Prior Publication Data
US 2022/0257102 A1 Aug. 18, 2022

Related U.S. Application Data

(60) Provisional application No. 63/293,251, filed on Dec. 23, 2021, provisional application No. 63/225,175, (Continued)

(51) Int. Cl.
*A61B 1/05* (2006.01)
*A61B 1/233* (2006.01)
(Continued)

(52) U.S. Cl.
CPC ............ *A61B 1/05* (2013.01); *A61B 1/00048* (2013.01); *A61B 1/227* (2013.01); *A61B 1/233* (2013.01)

(58) Field of Classification Search
CPC ............ A61B 1/00004; A61B 1/00006; A61B 1/00009; A61B 1/000094;
(Continued)

(56) References Cited

U.S. PATENT DOCUMENTS

2013/0178763 A1\* 7/2013 Al-Terki ............ A61B 17/3211
600/590
2013/0258080 A1\* 10/2013 Kuriyama ........ A61B 1/000094
348/240.99

(Continued)

OTHER PUBLICATIONS

International Search Report and Written Opinion of the International Searching Authority for International Patent App. No. PCT/US2022/16141 dated Apr. 25, 2022 (11 pages).

*Primary Examiner* — Timothy J Neal
*Assistant Examiner* — Pamela F Wu
(74) *Attorney, Agent, or Firm* — Ulmer & Berne LLP

(57) ABSTRACT

An ear nose and throat (ENT) imaging and analysis system includes an endoscope usable to capture images of the nasal canal and other aspects of patient anatomy. Endoscopic images may be presented to a user via a touchscreen display, and the software may provide different imaging modes that aid in identifying particular anatomical structures or areas within the nasal canal. In one mode, the system uses an object recognition process to identify the nasal valve opening within the images at a relaxed state, and during forceful inhalation, and then calculates the difference between the two states, which may be suggestive of nasal valve collapse. In other modes, the system is configured to identify abnormalities of the inferior turbinate, septum, or other anatomy, as well as empty spaces within the nasal canal, as well as areas and volumes of empty space and user defined boundaries.

14 Claims, 40 Drawing Sheets

Related U.S. Application Data filed on Jul. 23, 2021, provisional application No. 63/150,179, filed on Feb. 17, 2021.

(51) Int. Cl.
*A61B 1/227* (2006.01)
*A61B 1/00* (2006.01)

(58) Field of Classification Search
CPC .............. A61B 1/000095; A61B 1/233; A61B 1/00045; A61B 1/0005; A61B 1/05; A61B 5/0033; A61B 5/1128; A61B 1/04; A61B 1/045–053; A61B 1/000096; G06T 7/00; G06T 7/10–13; G06T 7/0012; G06T 2207/20081
USPC ......................................................... 600/109
See application file for complete search history.

(56) References Cited

U.S. PATENT DOCUMENTS

| | | |
|---|---|---|
| 2016/0133014 A1 | 5/2016 | Staples et al. |
| 2018/0153383 A1 | 6/2018 | Goshayesh et al. |
| 2019/0231220 A1 | 8/2019 | Refai et al. |
| 2019/0246951 A1* | 8/2019 | Baron .................. A61B 5/1128 |
| 2019/0297276 A1 | 9/2019 | Sachdev et al. |
| 2019/0380787 A1* | 12/2019 | Ye ...................... A61B 1/00149 |
| 2020/0297444 A1 | 9/2020 | Camarillo et al. |
| 2021/0015554 A1 | 1/2021 | Chow et al. |
| 2021/0037173 A1 | 2/2021 | Uemori et al. |
| 2021/0042553 A1* | 2/2021 | Oosake ................ A61B 1/0005 |
| 2022/0358773 A1* | 11/2022 | Thienphrapa ........ A61B 1/0005 |

* cited by examiner

SYSTEM AND METHOD FOR ENDOSCOPIC IMAGING AND ANALYSES

CROSS-REFERENCE TO RELATED APPLICATIONS

The present application claims the priority of U.S. Provisional patent Application Ser. No. 63/150,179, entitled System and Method For Endoscopic Imaging and Analyses, filed Feb. 17, 2021, U.S. Provisional patent Application Ser. No. 63/225,175, entitled System and Method For Endoscopic Imaging and Analyses, filed Jul. 23, 2021, and U.S. Provisional patent Application Ser. No. 63/293,251, entitled System and Method For Endoscopic Imaging and Analyses, filed Dec. 23, 2021, the disclosure of each of which is incorporated herein by reference in its entirety.

FIELD

The disclosed technology pertains to a system for imaging and analysis to detect anatomical characteristics and determine disease state prognosis.

BACKGROUND

Medical diagnosis is an important part of medical practice and may include a series of questions asked of a patient, physical examination or manipulation of the patient, collection of patient specimen samples, and use of instruments such as endoscopes and other diagnostic data collecting instruments. Each treatment that is provided to a patient may be contingent upon one or more prior diagnostic steps, and some diagnostic steps may themselves be contingent upon prior assessments. As a result, patients visiting a health care provider may be subjected to dozens of diagnostic steps over the course of identifying and treating a condition.

With these frequent diagnostic steps, factors such as time, cost, and patient comfort become very important. An initial examination for a bone or joint injury might include physical manipulation and a series of questions during a 5 minute interview where the patient experiences slight discomfort, while a magnetic resonance imaging scan ("MRI") or Computed Tomography (CT) for the same injury might require an hour or more where the patient is immobilized and isolated within the close confines of an MRI or CT machine. In addition the use of MRI or CT machines to precisely diagnose certain treatments that endoscopic systems are not able to detect currently, exposes the patient and staff to potential health hazards such as cause of cancer.

In the context of ear, nose, and throat ("ENT") treatment, diagnosing a treatable condition within the narrow passages of the nose and sinuses can be difficult due to the location and inability to directly view or access some anatomy related to ENT diagnosis. For example, while an otoscope may be used to quickly assess a patient for an ear infection, assessment of a patient for an obstruction of the nasal airways may require a computerized tomography scan ("CT"), MRI, or other complex, costly, and time consuming imaging procedure. While such imaging procedures are important and useful for medical professionals, the results are often meaningless or confusing to patients since they are computer generated images based upon various signal feedback rather than direct imaging of the patient anatomy. Furthermore, the use of the currently diagnostic systems such as CT and MRI scanners, do not allow the doctor to direct the patient to perform certain tasks, such as for example breathing in and out, to detect the state of the disease progression based on the anatomy changes which is the case for airflow obstruction.

What is needed, therefore, is an improved system for providing information usable by medical professionals and patients to diagnose and understand certain anatomical characteristics.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION

The inventors have conceived of novel technology that, for the purpose of illustration, is disclosed herein as applied in the context of medical imaging. While the disclosed applications of the inventors' technology satisfy a long-felt but unmet need in the art of medical imaging, it should be understood that the inventors' technology is not limited to being implemented in the precise manners set forth herein, but could be implemented in other manners without undue experimentation by those of ordinary skill in the art in light of this disclosure. Accordingly, the examples set forth herein should be understood as being illustrative only, and should not be treated as limiting.

Figure 1A:
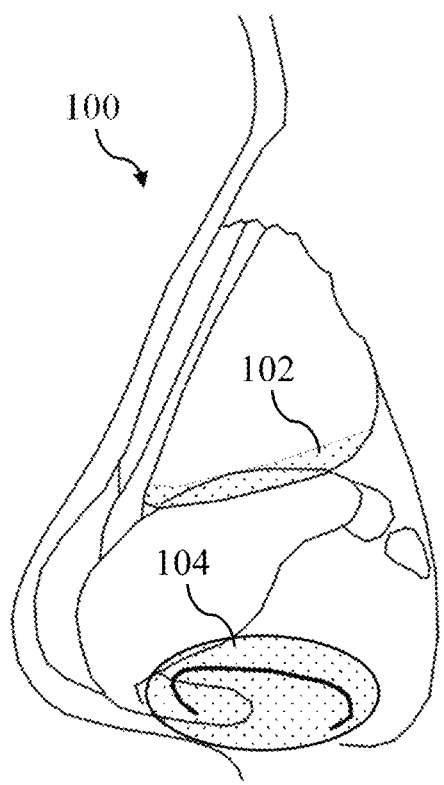
FIG. 1A is a schematic diagram that illustrates the positions of an internal nasal valve and an external nasal valve.

FIG. 1A is a schematic diagram that illustrates the positions of an internal nasal valve (102) and an external nasal valve (104) of a human nose (100). The external nasal valve (104) includes the tissue around the nostril opening, while the internal nasal valve includes the tissues within the nasal cavity, and is typically the narrowest point within the nasal cavity. Several ENT related conditions may be diagnosed based upon characteristics of the internal (102) and external nasal valve (104), which may be collectively referred to as the nasal valve. As an example, nasal valve collapse describes a weakness in the external (104) and/or internal nasal valve (102) muscle tissue that holds the valve open, which causes them to collapse into and obstruct the flow of air through the nasal cavity during heavy inhalation. As a result, the already narrow passageway becomes further obstructed which may reduce the patient's ability to effectively breathe through the nose, or block it altogether.

Figure 1B:
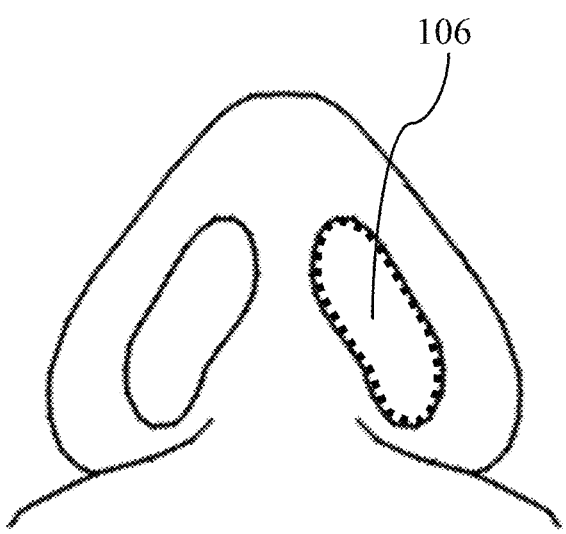
FIG. 1B is a schematic diagram that illustrates an airway of the nose during a relaxed state.
Figure 1C:
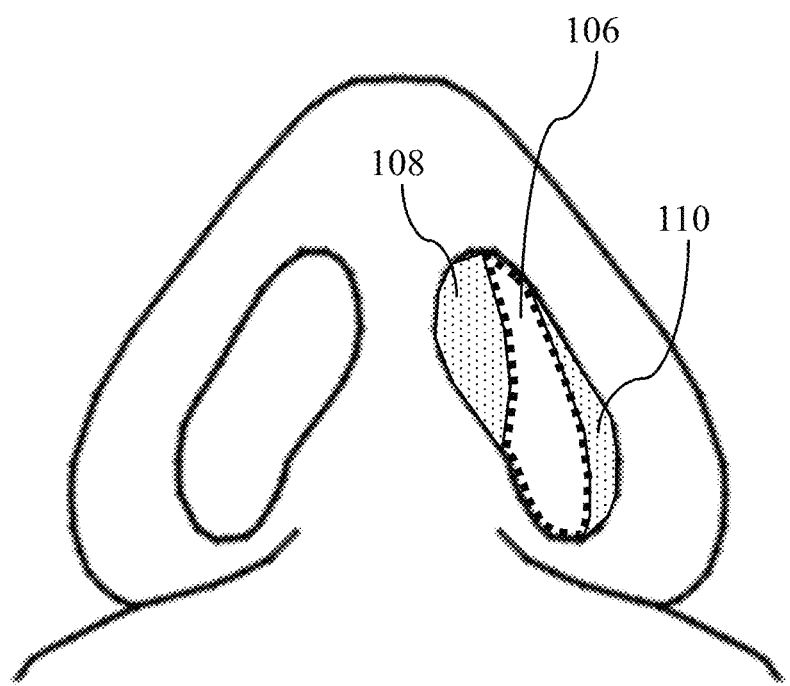
FIG. 1C is a schematic diagram that illustrates an airway of the nose during forceful inhalation.

FIGS. 1B and 1C illustrate the nasal valve during a relaxed state, and during forceful inhalation. In FIG. 1B, the nasal valve opening (106) is designated by a dotted boundary line. In FIG. 1C, the cross sectional area of the nasal valve opening (106) has reduced to about 50% of the area of its relaxed state, due to the collapse of anatomical tissues (108, 110) into the nasal canal. In addition to the obstruction of the airflow due to weakness of muscle tissue causing the collapse of external and/or internal nasal valve (104), also portions of the septum, inferior turbinate, or other tissues can cause airflow obstruction.

Figure 2:
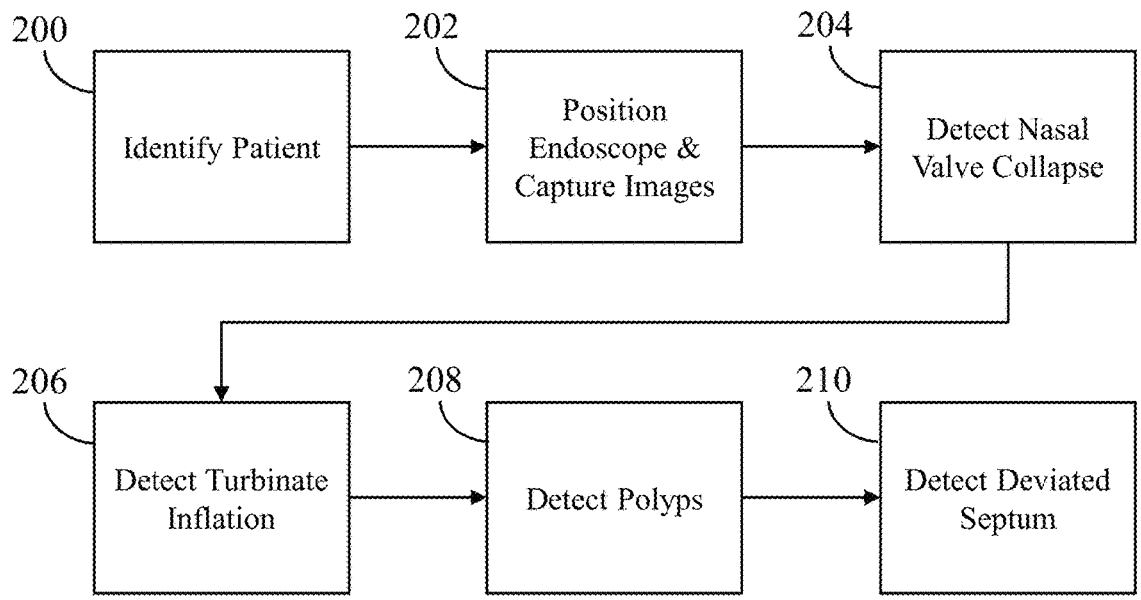
FIG. 2 is a flowchart of an exemplary set of high level steps that may be performed to provide ENT imaging and analysis.
Figure 3:
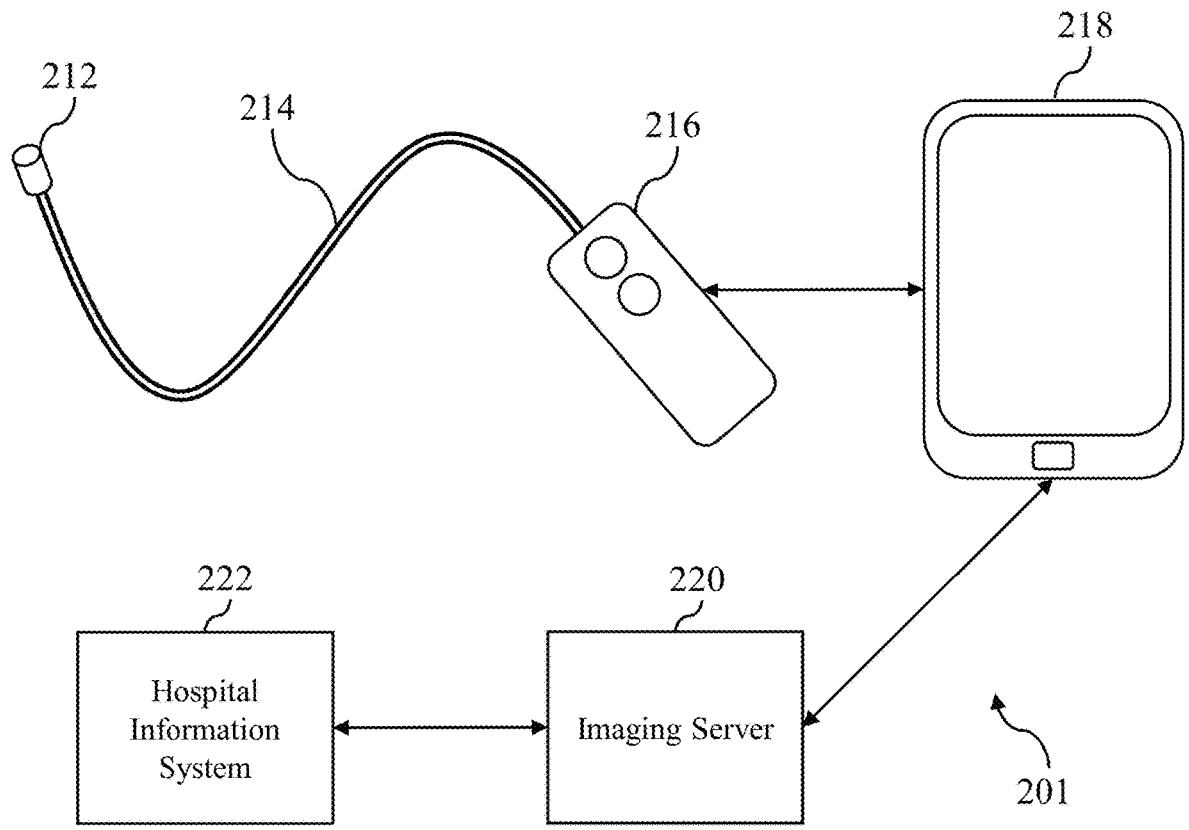
FIG. 3 is a schematic diagram of a system configured to perform ENT imaging and analysis.

Implementations of the disclosed technology may be used to aid in identifying nasal valve collapse in patients, and may also be used in other ENT and non-ENT related procedures. As an example, FIG. 2 is a flowchart of a set of high level steps that may be performed to provide ENT imaging and analysis using the disclosed systems, devices, and features. FIG. 3 shows a schematic diagram of a system (201) configured to perform ENT imaging and analysis, including some or all of the steps describes in FIG. 2 and elsewhere.

During imaging and analysis with the system (201), a patient may first be identified (200), which may include providing identifying information for the patient, or may include automatic identification of the patient using an endoscope (212) that will also be used to capture image data during the imaging and analysis of the patient anatomy. The endoscope (212) is coupled to a control (216) via a shaft (214) that contains cabling for exchanging power and data between the endoscope and the control (216), and which may be flexible, rigid, extendable and retractable, or of varying lengths depending upon a particular implementation.

The control (216) may include user controls such as buttons or other interfaces allowing a user to operate the endoscope (212), may include status lights or other indicators that may provide information to the user, and may include other components such as a processor, memory, and communication device capable of exchanging information with other devices wirelessly or via a wired connection. The control (216) may be in communication with an imaging device (218) which may be, for example, a smartphone, tablet, laptop, computer, or other proprietary computing device. In some implementations the control (216) and imaging device (218) may be an integrated unit or device sharing the same case, processor, memory, and other features. The imaging device (218) includes a processor, memory, and communication device, and also includes features such as a touchscreen display.

The imaging device (218) may be configured to provide a graphical user interface that guides the user through the imaging process, including identification (200) of the patient. As an example, an interface may be displayed on a touchscreen display showing a circular area overlaid up on images captured by the endoscope (212), with instructions to center the patient's face within the circular area. Once captured, a facial image may be used to create unique identifying information that is associated with the patient's imaging results and data, and may be used on subsequent appointments to verify the patient's identify and access prior records. While facial recognition is a known feature, the system (201) uniquely provides a guided interface that utilizes the same endoscope (212) that will be used for ENT imaging for facial recognition and association.

The system (201) also includes an imaging server (220), which may include one or physical servers, virtual servers, cloud servers, or other computing environments. The imaging server (220) is configured to provide image analysis features to remotely connected devices via a network, and to store, maintain, and update datasets and algorithms usable to aid in identifying certain characteristics of patient anatomy. The imaging server (220) may also be in communication with a hospital information system ("HIS") (222), which may store patient records, procedure records, practitioner records, and other information. The results of imaging and analysis may be provided to the HIS (222), as well as other information such as patient identifying (200) information usable to verify the patient.

Returning to FIG. 2, an endoscope such as the endoscope (212) may be positioned (202) based on the particular ENT process that is being performed, and images may be captured of the patient anatomy. Positioning (202) of the endoscope (212) will vary, but may generally include insertion of the endoscope (212) into the nasal canal via the nostril to varying depths. As images are captured by the endoscope (212), the user interface provided via the imaging device (218) may guide the practitioner through additional steps related to positioning (e.g., repositioning the endoscope (212) field of view by rotation, insertion, extraction, etc.) and identifying patient anatomy related to the ENT process. This may include identification of imaging characteristics suggestive of nasal valve collapse (204), inferior turbinate inflation (206), polyps (208), deviated septum (210), and other conditions, as will be described in more detail below. Each discrete type of identification may be performed based upon a user selected mode (e.g., a user may select a mode to detect nasal valve collapse), or a software interface may guide the user through each step (e.g., a user may be instructed to position the endoscope and aid in identifying nasal valve collapse, and next to reposition the endoscope and aid in identifying turbinate inflation, etc.).

A distinct advantage of the implementations disclosed in FIGS. 2 and 3 is the use of the endoscope (212) for imaging. As compared to CT, MRI, and other imaging systems, use of an endoscope to aid in diagnosis can be performed quickly and with minimal setup and pre-configuration. As an example, the endoscope (212) and control (216) may be battery powered, and small enough to fit within a pocket or easily held in the hand. Additionally, the results of imaging will be direct digital images of patient anatomy, and so may show details that are useful and relevant to both the patient and practitioner, and that are not available via indirect imaging of the patient anatomy.

Figure 4:
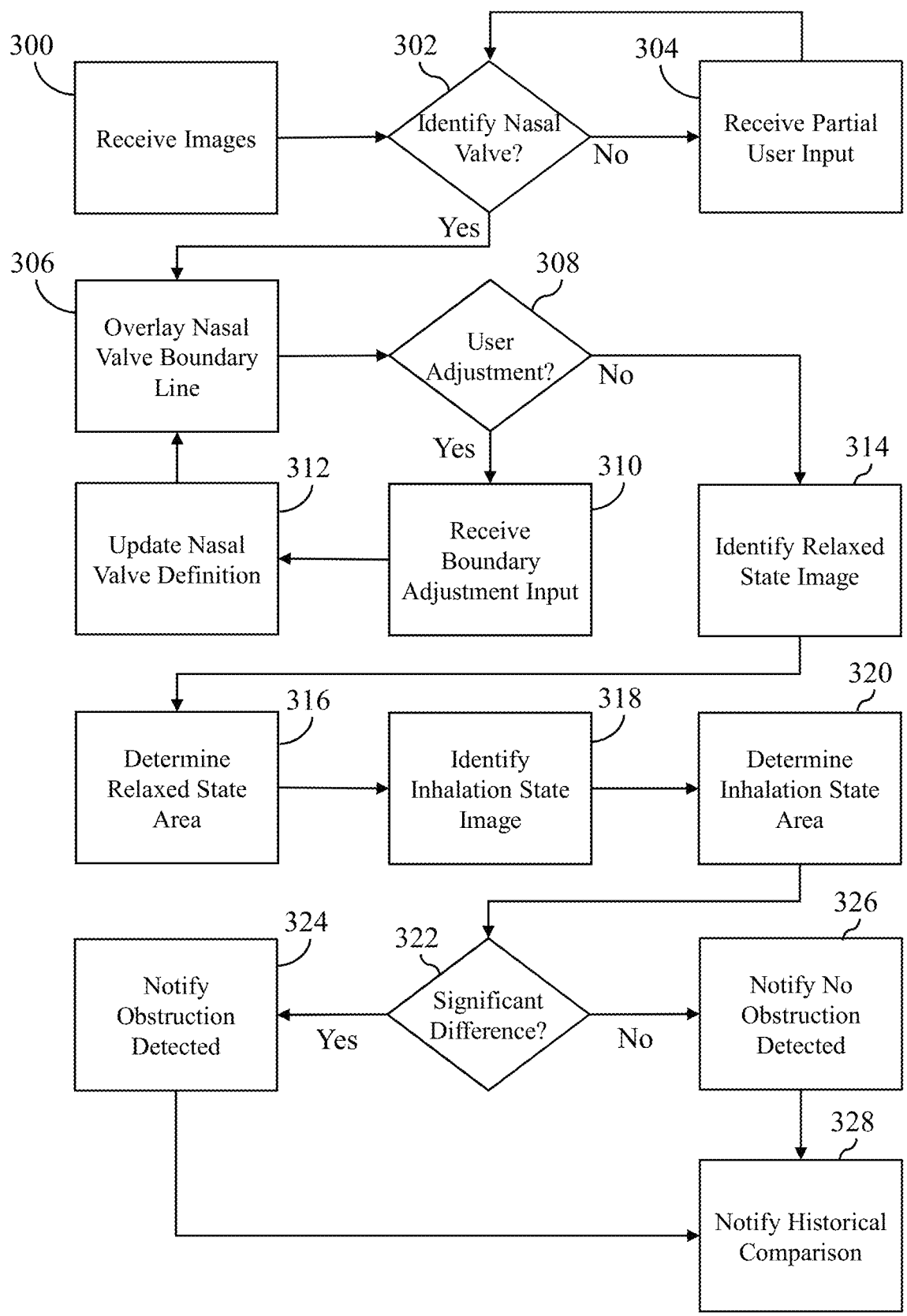
FIG. 4 is a flowchart of an exemplary set of steps that may be performed with the system of FIG. 3 to identify nasal valve obstruction.

As has been described, nasal valve collapse is one condition which implementations of the disclosed system may aid a practitioner in identifying. FIG. 4 is a flowchart of an exemplary set of steps that may be performed with a system such as that of FIG. 3 to identify nasal valve collapse or other obstruction. The steps of FIG. 4, as well as other figures, may be performed by one or more of the control (216), the imaging device (218), and the imaging server (220), depending upon a particular implementation. As an example, in some implementations the datasets and algorithms used for image analysis may be stored and executed by the imaging server (220) as images are captured by the endoscope and transmitted to the imaging server (220). In some implementations, these datasets and algorithms may be downloaded and stored locally on the imaging device (220) and/or control (216). In some implementations, pre-processing of the images may occur prior to transmitting images to the imaging server (220), and may include processing to reduce file size of the image, crop irrelevant portions of the image, adjust color and contrast settings of the image to highlight certain anatomy, and other changes.

As images are captured by the endoscope and received (300), the system may attempt to identify (302) the anatomical structures of the external nasal valve (104), internal nasal valve (102), or both, if they are present in the image. Identification (302) of the nasal valve anatomy may be performed using an object recognition process that attempts to identify the particular anatomy based upon a definition dataset that describes the colors, shapes, arrangements, and relationships between defined anatomies with through a combination of anatomical images and user defined annotations identifying particular anatomical structures within those images. Such object recognition may be performed using an expert system, artificial intelligence, or other process. As one example, this may include a convolutional neural network ("CNN") configured and trained to segment images and identify defined structures. A training dataset used to train the CNN may include images and associated annotations that define characteristics of those images, and may initially include between about 200 and 500 images of nasal passageways, from different patients, and from different perspectives (e.g., both the ideal perspective of the endoscope (212) once positioned, and non-ideal positions), and a set of annotations defining particular characteristics within those images (e.g., empty space, various anatomical structures).

In some scenarios, the system may be able to identify (302) the anatomy related to nasal valve collapse without manual intervention, such as where the captured image shares many similarities with images that have been used to train the object recognition process. Where the system is not able to identify (302) the nasal valve anatomy, a user may be prompted to provide a partial input defining the anatomical structure. As an example, this may include prompting the user to begin tracing the edge of the exterior nasal valve, or interior nasal valve, using their finger via a touchscreen display of the imaging device (218). As partial inputs are received (304), the system will continuously re-evaluate the image with the object recognition process while considering the partial user input. As an example, the external nasal valve may not be immediately recognized due to lighting issues or unique anatomical characteristics, but as partial user input is received the system is able to narrow the portions of the image being searched for recognizable anatomy, and is able to user the manual inputs as a guideline for identifying known structures within its dataset.

Figure 10:
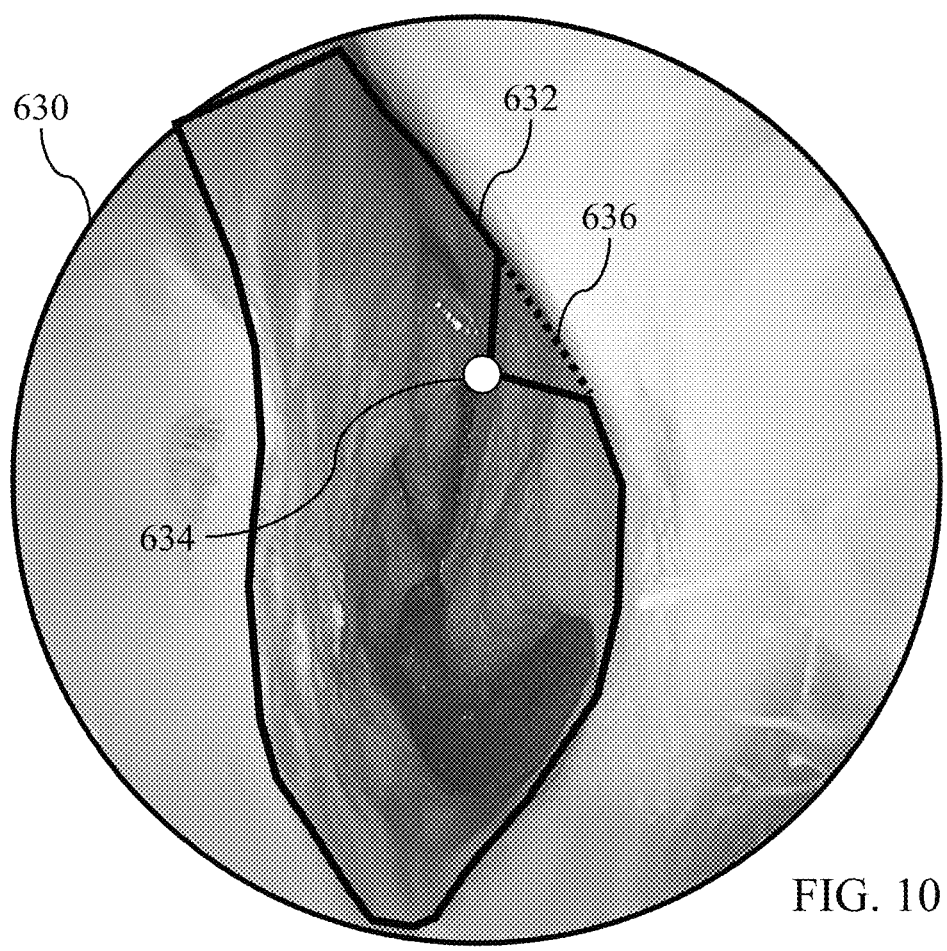
FIG. 10 is a screenshot of an exemplary interface for identifying and manually adjusting boundaries for selected anatomy.

Once the nasal valve anatomy is identifiable (302), the system will determine the boundary of that anatomy within the image and overlay (306) a boundary line on the display of that image (e.g., via the software interface of the imaging device (218)). Where a user is providing partial user input that is used to identify (302) the nasal valve anatomy, the boundary will automatically complete in near-real time so that the user may cease tracing the anatomy. Where a user does not agree with the automatically applied boundary, the user may provide a manual adjustment (308) via the touchscreen display that, when received (310), will be used by the system to update (312) the defined boundary of the nasal valve anatomy and overlay (306) an updated boundary line. FIG. 10 provides one example of an interface that allows a user to manually adjust (308) an overlaid boundary line. An image (630) captured by the endoscope may be displayed with a boundary line (632) surrounding the defined anatomy (e.g., in the case of FIG. 10, the boundary line surrounds and identifies the largest cross-sectional empty space of the nasal canal). Automatic overlay of the boundary may result in a portion of the boundary being displaced from the accurate boundary position (636), illustrated as a dotted line. Using the touchscreen display or another interface, the user may select one or more portions of the boundary (634) and drag them across the display until positioned at the accurate location (636).

Returning to FIG. 4, where no user adjustment (308) is needed, the system may identify (314) an image from a set of images (e.g., such as a sequence of images captured during video capture by the endoscope) that is captured during a maximally relaxed state (e.g., where the nasal valve has the maximum cross-sectional area, as shown in FIG. 1B). This relaxed state image may be identified or selected based upon the cross-sectional opening having a maximal area, based upon a manual input by a user tagging or freezing the video image at the desired image frame, based upon an audio signal captured by an audio capture device of the endoscope (212) (e.g., based upon a lack of noise, such as during moment at the end of an exhalation, just prior to an inhalation), or based upon other factors. The system may then determine (316) the cross sectional area of the nasal valve opening within the relaxed state image. This determination (316) does not require a definite scale, and so may be calculated in pixels of the image for example.

The system may also identify (318) an image from a set of images that is captured during a high pressure state, such as during a forceful inhalation. As with the relaxed state image, this image may be identified or selected based up on a calculated minimum area of the cross-sectional opening, based upon a user input tagging the image, based upon a captured audio signal indicating forceful inhalation, or based upon other factors. The system may then determine (320) the cross sectional area of the inhalation state image in pixels or other units of measurement.

Next, the system may determine (322) whether there is a significant difference in the area of the nasal valve opening between the relaxed state image and the inhalation state image using the calculated areas of the boundaries for those openings. As an example, the system may be configured with a threshold for indicating whether such difference is significant, and such a threshold may be static, or may be dynamically determined based upon various other factors (e.g., patient age, other health conditions of the patient, a particular procedure or potential diagnosis that the patient is inquiring about, etc.).

Where the difference is significant (322), the system may notify the user (324) that an obstruction of the nasal valve opening is detected via a software interface of the imaging device (218) or another device, and may provide further information such as a percentage change in the area of the opening between inhalation and relaxed states, additional images or video sequences showing the change, which may include boundary overlays, and other information. Where no significant difference is detected (322), the system may notify (326) the user that there is not an obstruction and may provide similar information (e.g., images, video sequences, overlays, percentage difference, etc.). The system may also notify (328) the user of a historical comparison between the current measurement and one or more past measurements for that patient. This may include providing comparison images and measurements comparing a present measurement to a past measurement, which may show advancement of the nasal valve collapse, or may show a pre-procedure/post-procedure comparison to highlight improvement in the airway.

During the steps of FIG. 4, the system may also provide various information related to the nasal valve collapse identification to the imaging server (220), the HIS (222), or both, or to other third party systems or servers. As an example, partial user input (304), user adjustments (308), and other user feedback may be provided to the imaging server (220) and used to refine and improve algorithms, datasets, training data, neural networks, or other object recognition processes so that anatomical boundaries may be identified more readily and accurately in future images that have similar characteristics. As another example, information provided during notification (324, 326) of whether or not a significant obstruction exists may also be provided to the HIS (222) and associated with the patient to create records usable for subsequent treatment plans, diagnosis plans, or other processes where objective measurement and verification of nasal collapse may be useful.

Figure 5:
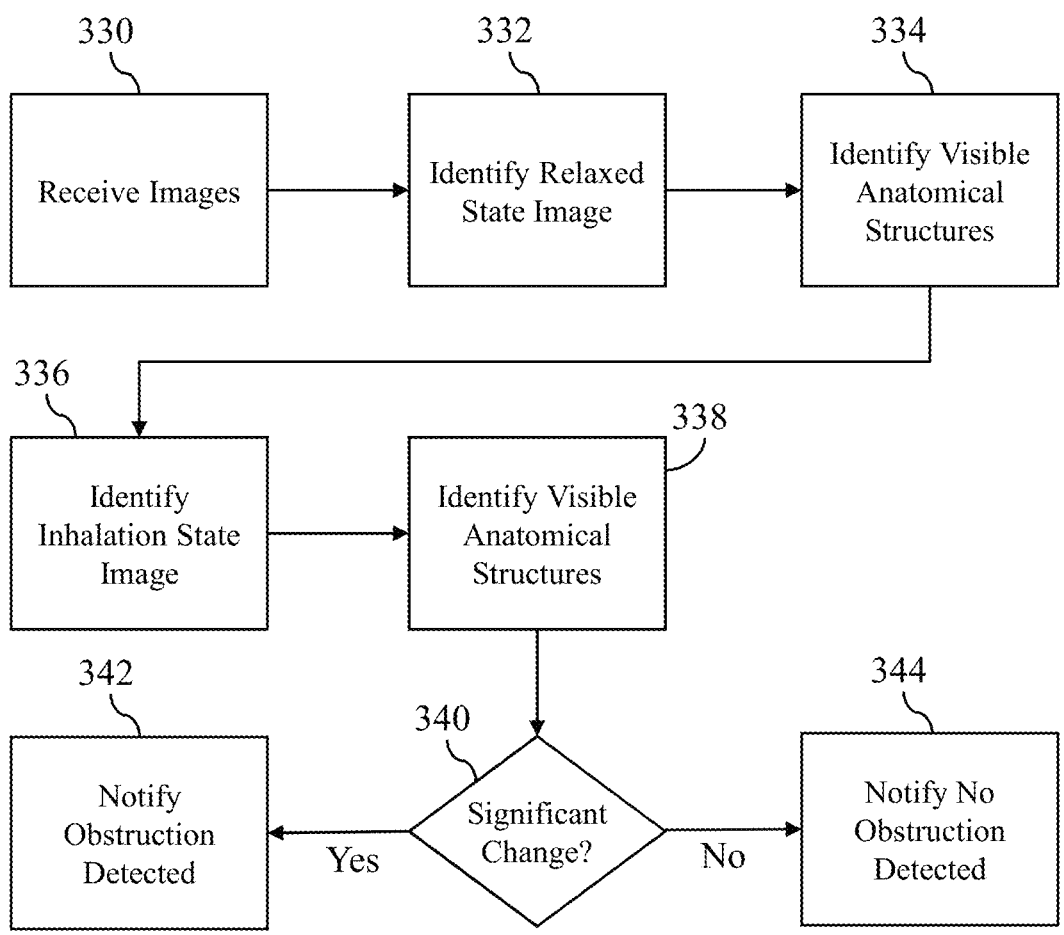
FIG. 5 is a flowchart of an alternate exemplary set of steps that may be performed with the system of FIG. 3 to identify nasal valve obstruction.

FIG. 5 is a flowchart of an alternate exemplary set of steps that may be performed with a system such as that of FIG. 3 to identify nasal valve obstruction. These steps may be performed separately from, or in conjunction with steps such as those of FIG. 4. As images of the nasal canal are received (330), the system may identify (332) a relaxed state image, as has been previously described. The system may then identify (334) anatomical structures that are visible in the image, other than the general empty space or cross-sectional opening identified in FIG. 4 (e.g., such identification may include identification of the septum, inferior turbinate, or other anatomy, and may include boundary overlay, partial user input, user adjustments, and other steps described in FIG. 4).

The system may then identify (336) an image of a forceful inhalation state, as has been previously described, and may then attempt to identify (338) the same set of previously identified anatomical structures within that image (e.g., where the inferior turbinate was previously identified, it will be subsequently identified in the inhalation state image). The system may then determine a level of obstruction of the airway based upon a significant change (340) in the visible area of other identified anatomy. As an example, this may include determining that the inferior turbinate is fully visible in a relaxed state, and only 30% visible during an inhalation state, or that the septum is fully visible in a relaxed state and entirely obscured by collapsed anatomy during an inhalation state. The significant change may be configured as a threshold value for each identified anatomy. As with prior examples, where a significant visible change exists (340), the system may provide one more notifications indicating the detected obstruction (342), or notifications indicating no detected obstruction (344), as has been previously described in the context of FIG. 4.

It should be understood that the sequences of FIGS. 4 and 5 are exemplary only, and some of the described steps may not be performed, or may be performed in different sequences, or in parallel. As an example, in some implementations the steps of identify (302) and overlaying (306) a visible boundary on the nasal valve opening may be performed numerous times, in real time, on sequences of images captured by the endoscope during video capture, and relaxed state images and inhalation state images may be identified (314, 318) from within that captured and bounded set. Alternately, in some implementations, a number of endoscopic images may be received during video capture and, prior to subsequent processing, the relaxed state image and inhalation state image may be identified (314, 318) from within that set. In such an implementation, identification (302) and bounding (306) of the nasal valve opening may only be performed for those two images, or another subset of captured images, rather than on a real-time sequence of images.

Figure 6A:
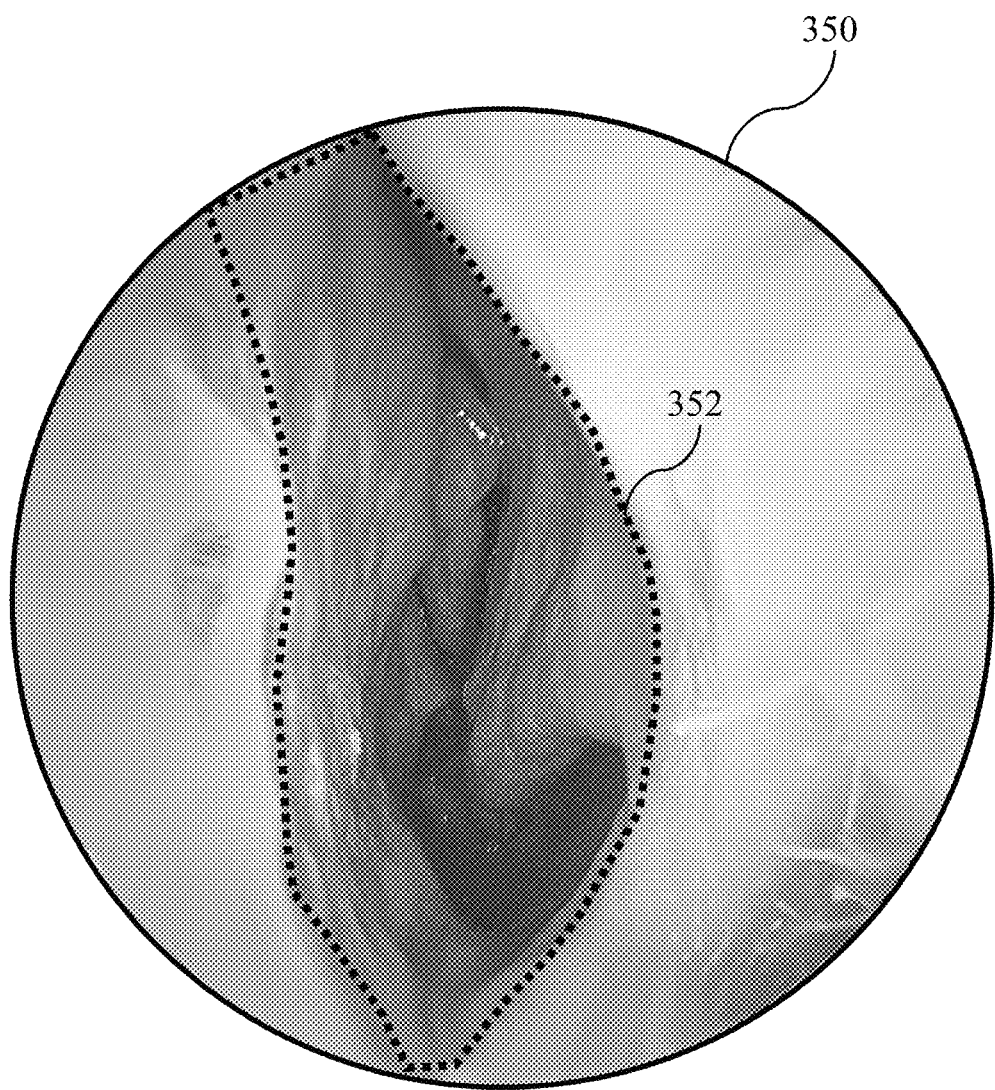
FIG. 6A is a screenshot of an exemplary interface for identifying and viewing an airway at a first step.
Figure 6B:
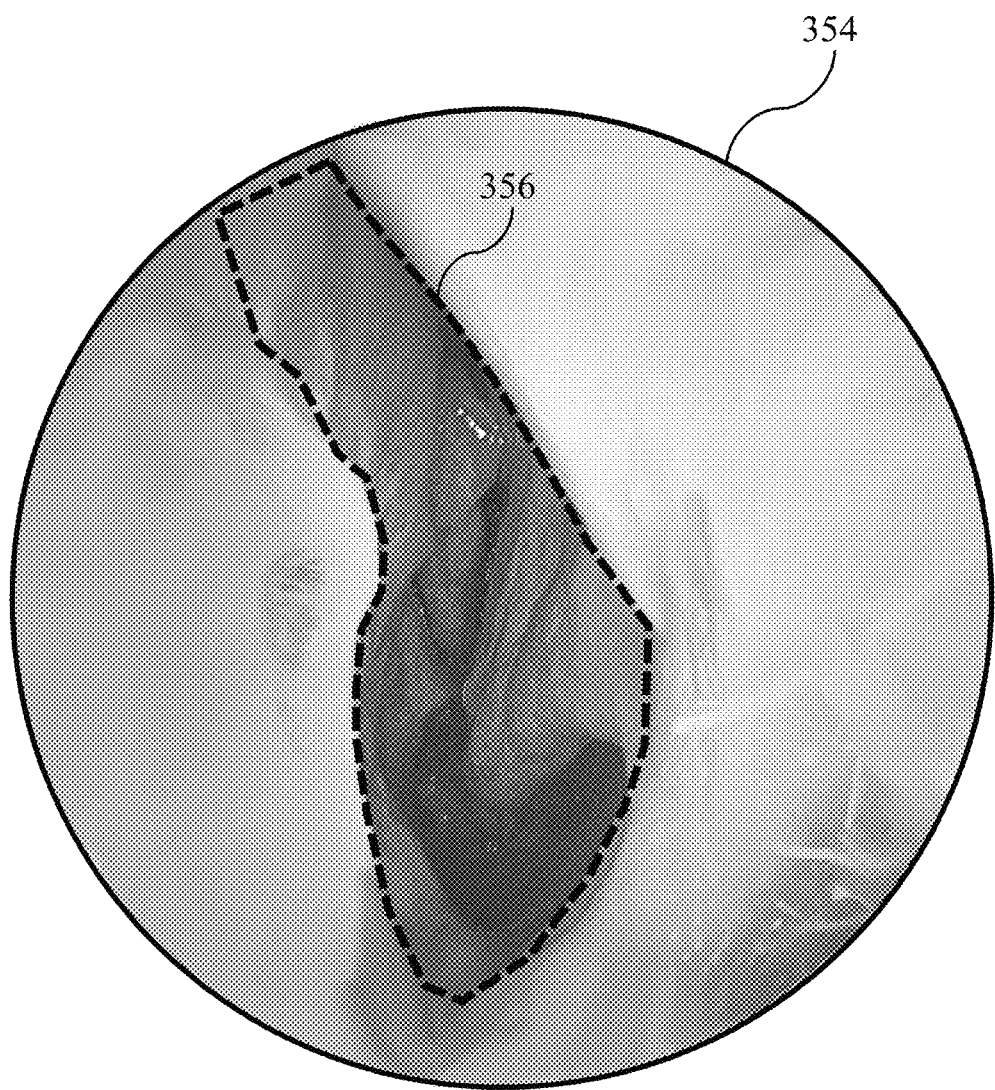
FIG. 6B is a screenshot of the interface of FIG. 6A at a second step.
Figure 6C:
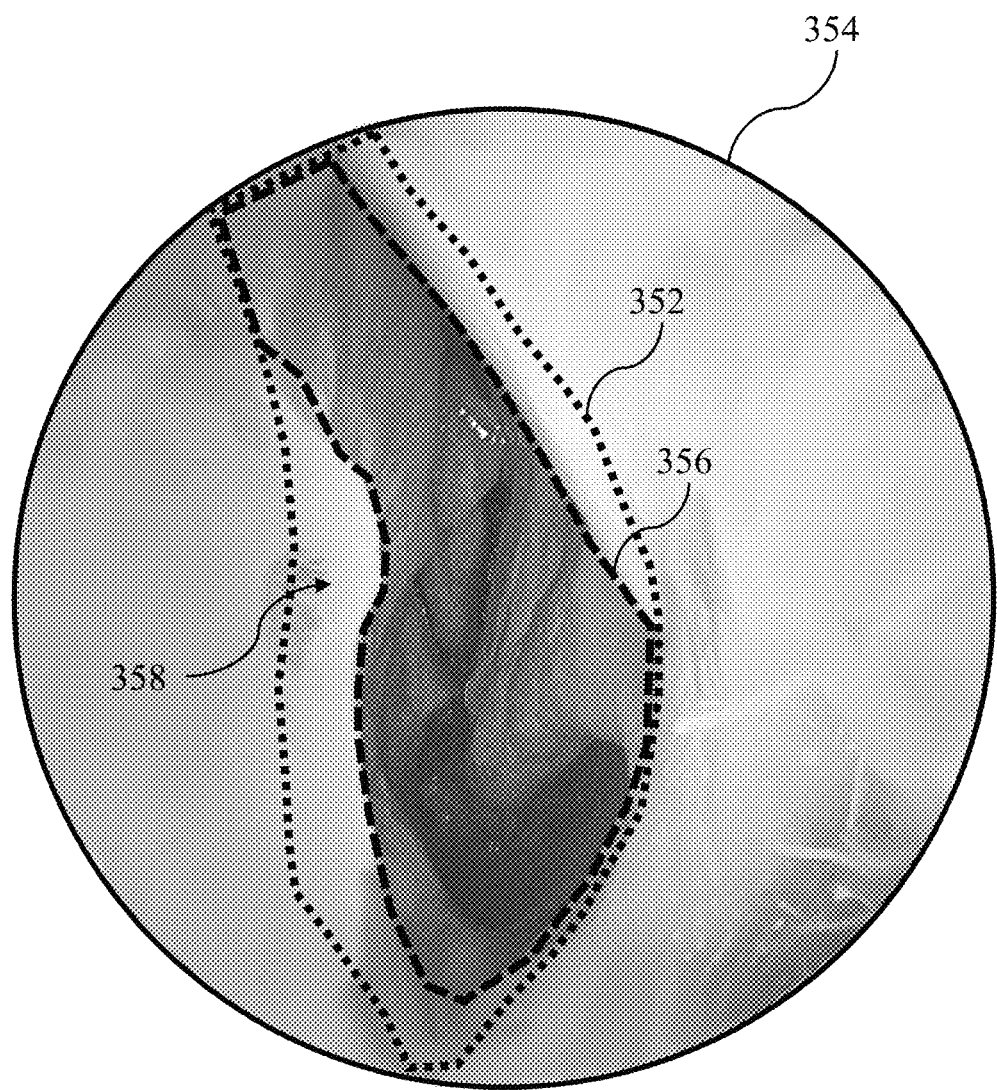
FIG. 6C is a screenshot of the interface of FIG. 6A at a third step.

FIGS. 6A through 6C show screenshots of an interface that may be provided during steps such as those of FIGS. 4 and 5, and are also more generally illustrative of the object detection and comparison process previously described. FIG. 6A shows an image (350) of the nasal canal captured by an endoscope during a relaxed state of the patient, and includes a maximal valve opening boundary (352) indicated by a dotted line. FIG. 6B shows an image (354) of the nasal canal captured by an endoscope during forceful inhalation by the patient, and includes a minimal valve opening boundary (356) indicated by a dashed line. FIG. 6C shows the image (354) of FIG. 6B with each boundary line (352, 356) included, highlighting a number of collapsed areas (358) where anatomy has collapsed into an obstructed the flow of air through the nasal canal. The above images may be displayed to a user of the system during imaging of a patient (e.g., via the imaging device (218) or another device), and may be directly interacted with to provide partial inputs (304), adjust boundaries (308), or report differences in area between maximal and minimal valve openings. The area change can be presented in terms of percentage changes by measuring the pixel area of the images before and after and calculating the percentage difference. Such images and annotations may also be displayed to the patient themselves via any appropriate device, and may be provided to the imaging server (220), HIS (222), or other devices.

Figure 7A:
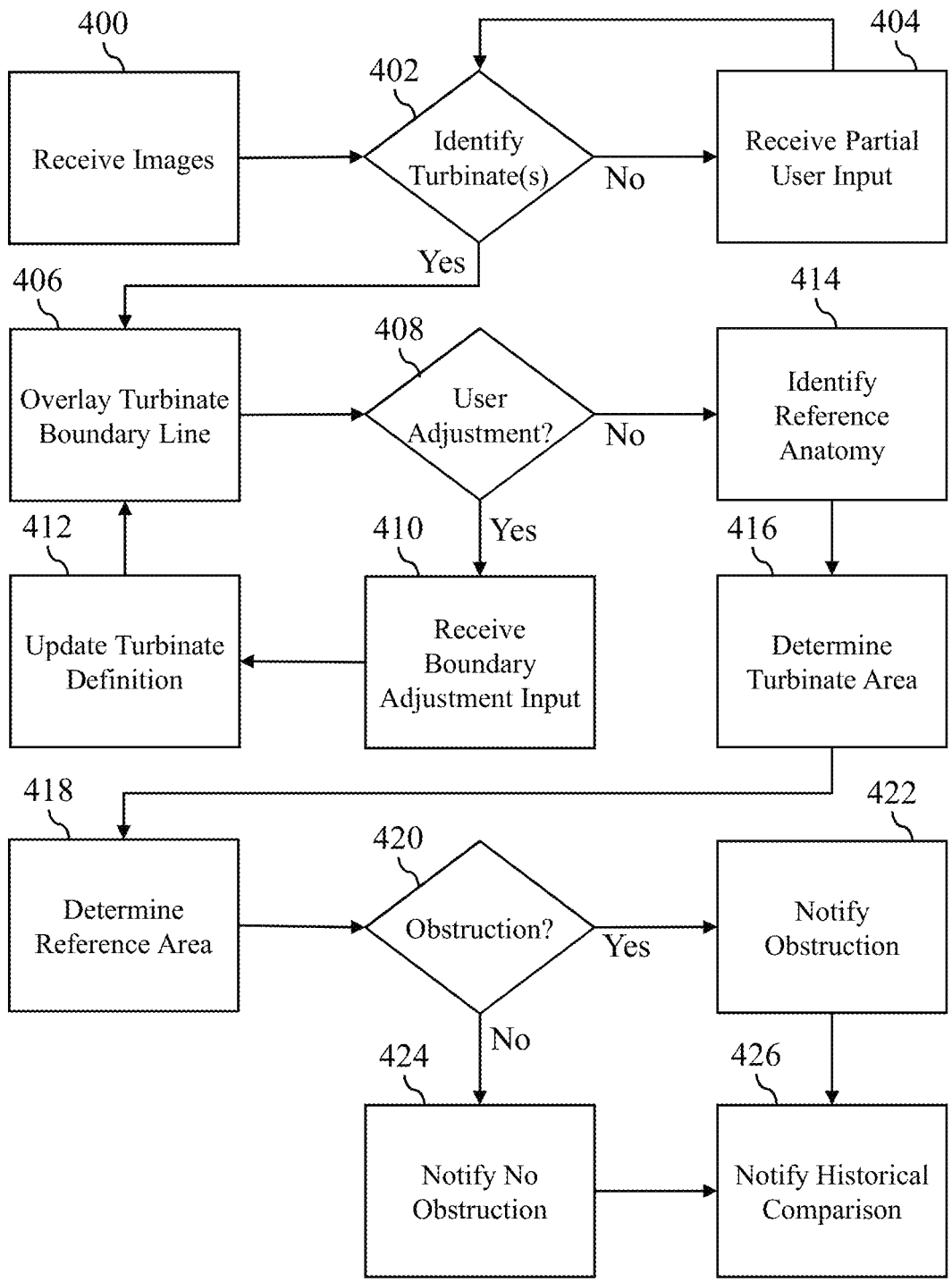
FIG. 7A is a flowchart of an exemplary set of steps that may be performed with the system of FIG. 3 to identify obstruction by the inferior turbinate.

FIG. 7A is a flowchart of an exemplary set of steps that may be performed to identify obstruction of the nasal airway due to inflation or inflammation of the inferior turbinate. The analysis of FIG. 7A shares some similarities with that of FIG. 4, but does not utilize a relaxed state and inhalation state comparison to measure obstruction. As the system receives images (400), a turbinate anatomy such as the inferior turbinate may be identified (402) using the object recognition process, either automatically or based upon received (404) partial inputs identifying the turbinate, as has been previously described. A boundary line may be overlaid (406) upon the turbinate anatomy, and may be adjusted by a user (408) if needed, with any such adjustment being received (410) and used to update (412) the turbinate anatomy boundary line, as has been previously described.

Figure 7B:
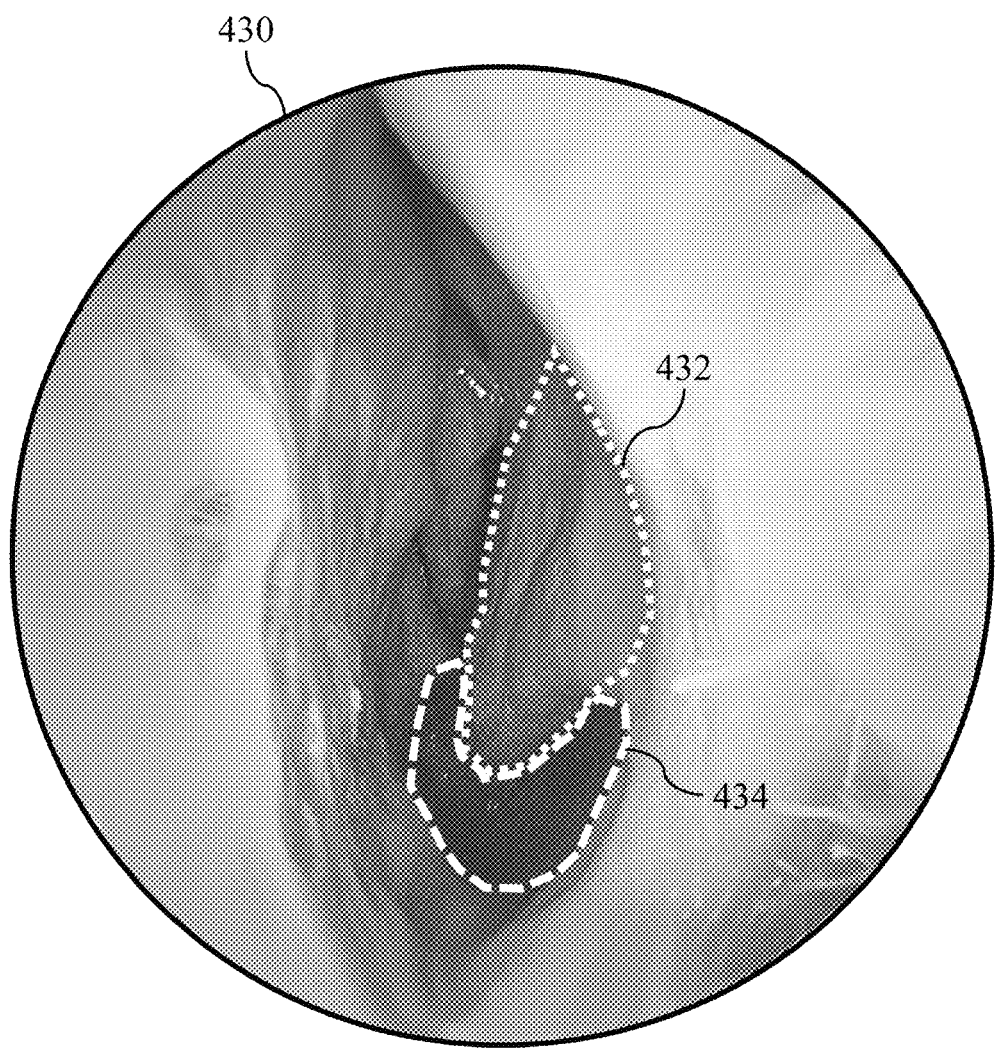
FIG. 7B is a screenshot of an exemplary interface for identifying and viewing the inferior turbinate relative to other anatomy.

Next, the system may identify (414) one or more reference anatomical structures or areas within the image. Reference anatomy may be any other anatomical structure, or discrete area within the image, whose area or position generally corresponds to or suggests the area or size of the turbinate anatomy. FIG. 7B provides one such example, in the form of a screenshot of an interface that may be used during identification of obstruction by the turbinate. An endoscopic image (430) is shown, with a boundary line (432) surrounding the inferior turbinate, and a boundary line (434) surrounding the empty space that surrounds the lower tip of inferior turbinate.

Next, the system may determine the area (416) of the turbinate by, for example, calculating the area of pixels within the boundary line (432) of the turbinate, and may also determine (418) the area of the reference anatomy by, for example, calculating the area of pixels within the boundary line (434) of the empty space. The system may then determine (420) whether the inferior turbinate is obstructing the nasal canal by comparing the areas of the turbinate anatomy and the reference anatomy. This comparison may be driven by a configured set of comparison values between the turbinate anatomy and various reference anatomies, and the comparison may be performed using one or more reference anatomies. As an example with reference to FIG. 7B, the system may be configured to identify a turbinate obstruction where the area of the turbinate boundary (432) is more than twice the area of the empty space boundary (434). As with prior screenshot examples, the interface of FIG. 7B may be displayed to a user during identification of the inferior turbinate, may receive partial user inputs and user adjustments, and may be displayed during notification of obstruction and/or transmitted to other devices, as has been previously described.

After determining whether a significant obstruction by the turbinate anatomy exists (420), the system may provide notifications (422) that an obstruction exists, notifications (424) that no obstruction exists, and notifications of one or more historical comparisons (426) of the turbinate anatomy, as has been previously described.

Figure 8A:
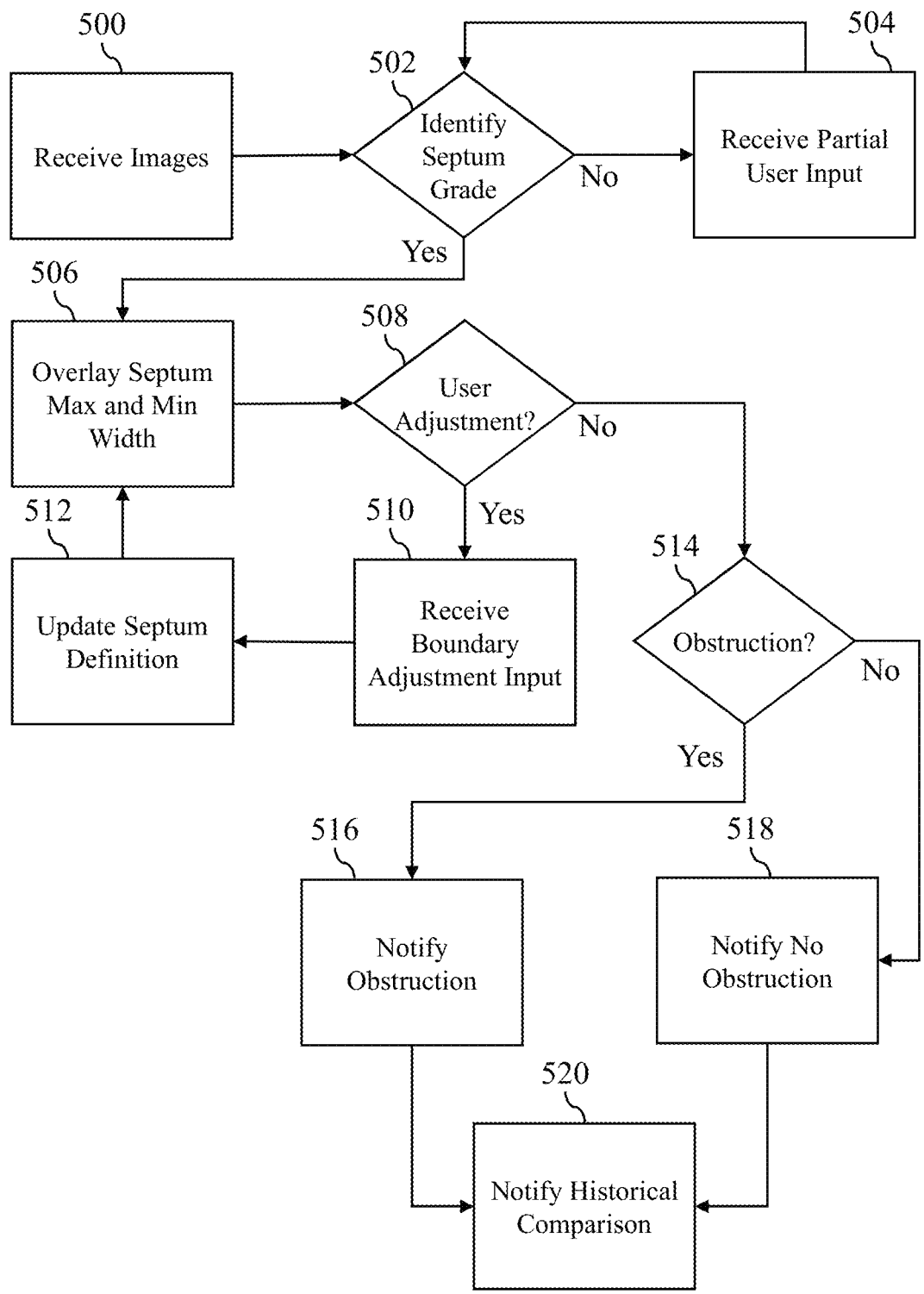
FIG. 8A is a flowchart of an exemplary set of steps that may be performed with the system of FIG. 3 to identify obstruction by the septum.

A system such as that shown in FIG. 3 may be used to identify additional anatomy characteristics using an endoscope. As an example, FIG. 8A is a flowchart of a set of steps that may be performed to identify obstruction of the nasal canal by the septum (e.g., a deviated septum). As with prior examples, the system may receive images (500) of anatomy from the endoscope (212). As images are received (500), the system may identify (502) the grade or slope of the septum within the image. This may include using the object recognition feature to identify the widest empty space of the nasal canal between the septum and the opposing anatomy (e.g., often the inferior turbinate), and identifying the narrowest empty space of the nasal canal between the septum and the opposing anatomy. This may include receiving (504) partial user inputs to aid the system in identifying the narrowest and widest portions of empty space, as has been previously described. Where the septum grade is identifiable (502), the system may overlay (506) borders or other markers indicating the maximum and minimum widths of the empty space left by the septum, which are indicative of the changing grade or slope of the septum. As with prior examples, the user may adjust (508) the automatically identified and overlaid septum grade markings.

Figure 8B:
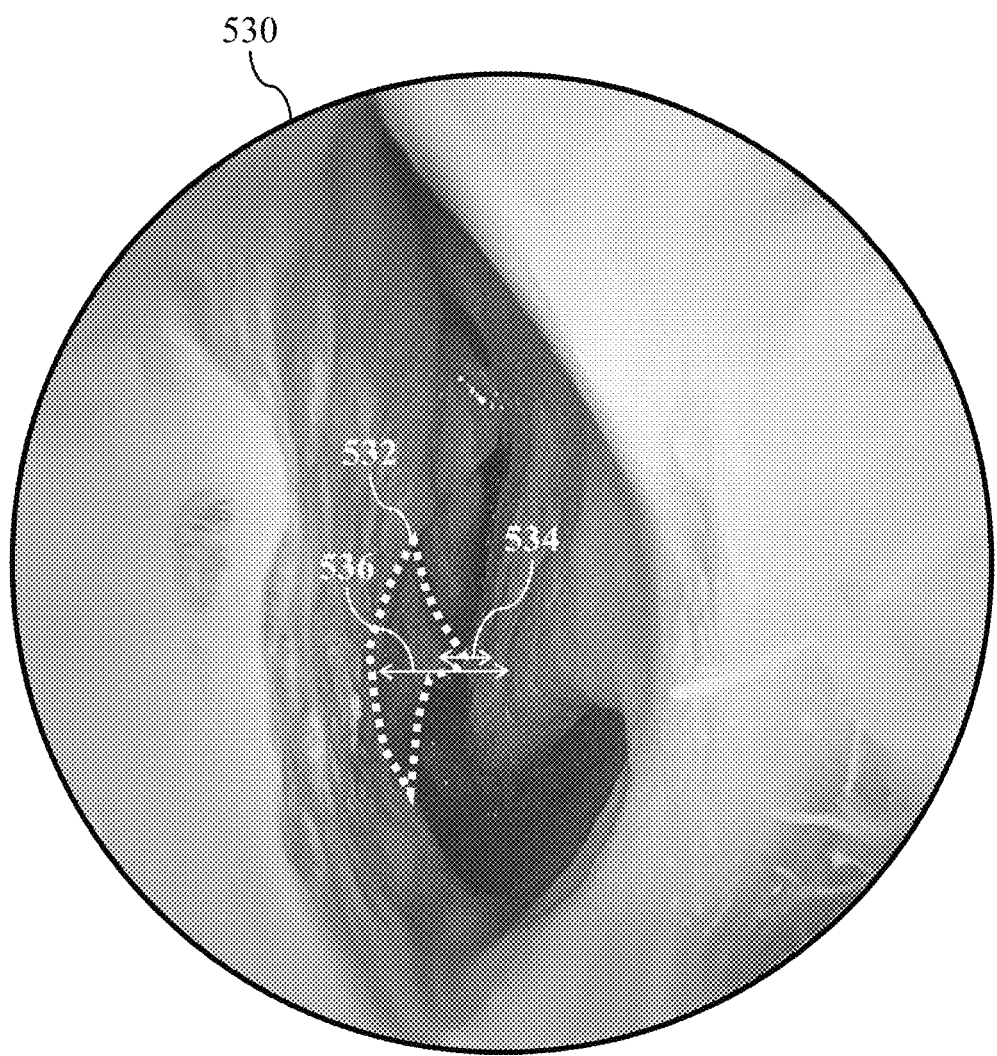
FIG. 8B is a screenshot of an exemplary interface for identifying and viewing obstruction by the septum.

FIG. 8B shows an interface that may be used to aid in identifying (502) the grade of the septum, providing partial user inputs (504), and adjusting (508) an automatically overlaid (506) septum grade. An endoscopic image (530) of the nasal canal anatomy is shown, and a border (532) is overlaid on the septum. The septum itself may be identified as part of determining the septum grade, and may be visually overlaid with a boundary to visually illustrate and/or provide an additional visible reference to aid in identifying the minimum and maximum width of the nasal canal related to the septum. The image (530) also includes a maximum width indicator (536) and a minimum width indicator (534) that run between a portion of the septum on the left side of the image (530), and an opposing portion of anatomy on the right side of the image (530). The indicator lines (534, 536) may be overlaid automatically based upon object recognition of the septum, and may also be based upon an estimation of depth, or a measurement of depth, as will be described in more detail below.

Once the septum grade has been identified, the system may determine whether the septum is obstructing (514) the nasal canal based at least in part upon the identified grade. Septum grades indicative of an obstruction (514) may include those having a sharp or sudden change in grade between the maximum and minimum width, as well as those including a gradual change in grade. The significance of the change in grade may be configured as a threshold or other evaluation metric, such as determining an obstruction (514) when the difference (e.g., in pixels or another unit of measurement) between the minimum and maximum gap is 50% or greater (e.g., where the maximum width is 100 px, and the minimum width is 50 px or less). As with prior examples, the system may then notify (516) whether an obstruction exists, notify (518) that no obstruction exists, or may notify (520) of a historical comparison to a prior septum evaluation in order to show a natural change in the state of the septum, or a pre-procedure to post-procedure comparison. The interface and information of FIG. 8B may be displayed to a user during imaging and analysis, may be displayed to a patient post-procedure to illustrate the analysis, or may be otherwise provided to the imaging server (220), HIS (222), or other devices as has been described.

Figure 9A:
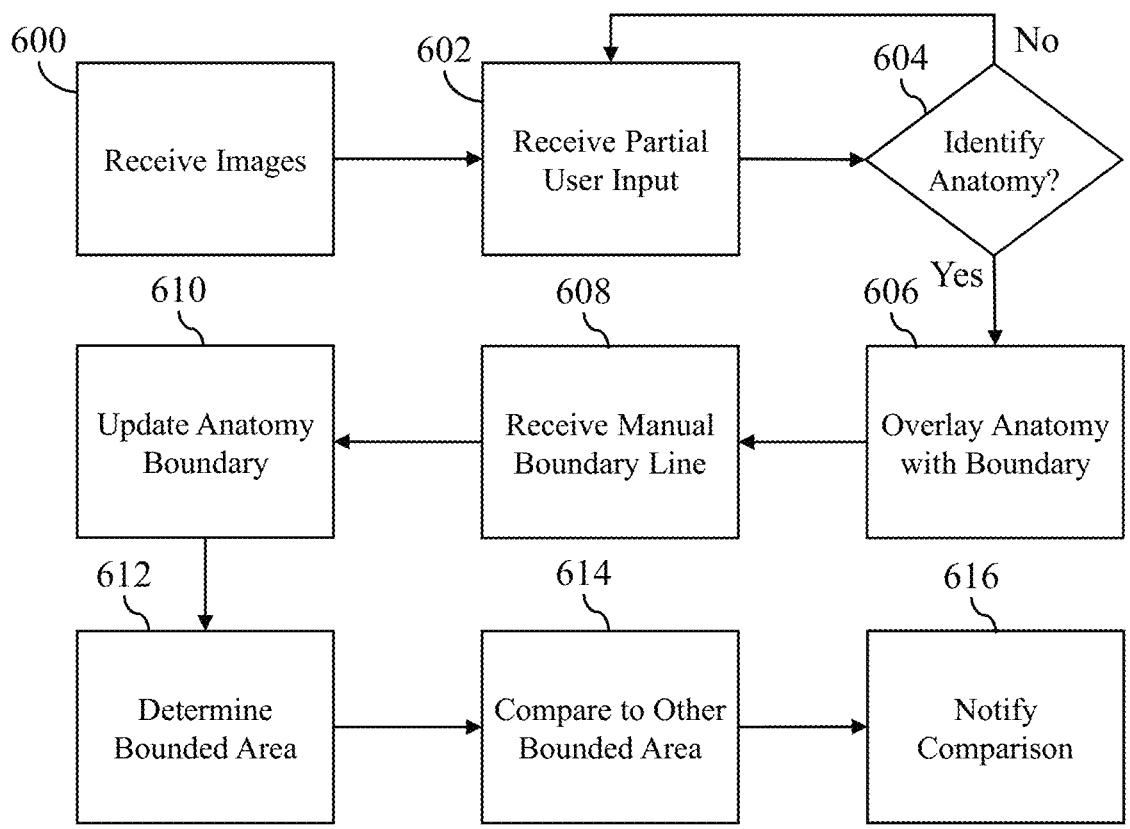
FIG. 9A is a flowchart of an exemplary set of steps that may be performed with the system of FIG. 3 to identify and define manual boundaries for selected anatomy.

The system may also be usable by a practitioner to make custom arbitrary measurements of nasal anatomy based upon endoscopic images. As an example, FIG. 9A shows a set of steps that may be performed to identify and define manual boundaries for selected anatomy, which may be usable to evaluate discrete anatomy, or to compare the sizes of different anatomies. As with other examples, images may be received (600) from an endoscope. While in the manual measurement and comparison mode, the system may not automatically identify and overlay boundaries on anatomy, and instead may receive (602) partial user inputs and attempt to identify (604) the anatomy that the user is drawing a boundary for based upon the received (602) partial inputs. In some implementations, this may include receiving partial inputs (602) and providing them as inputs to an object recognition process in order to guess at which anatomy the user is selecting (e.g., septum, inferior turbinate, empty space, nasal valve opening, etc.). When the anatomy is identified (604), the system may overlay (606) a boundary on the anatomy.

Figure 9B:
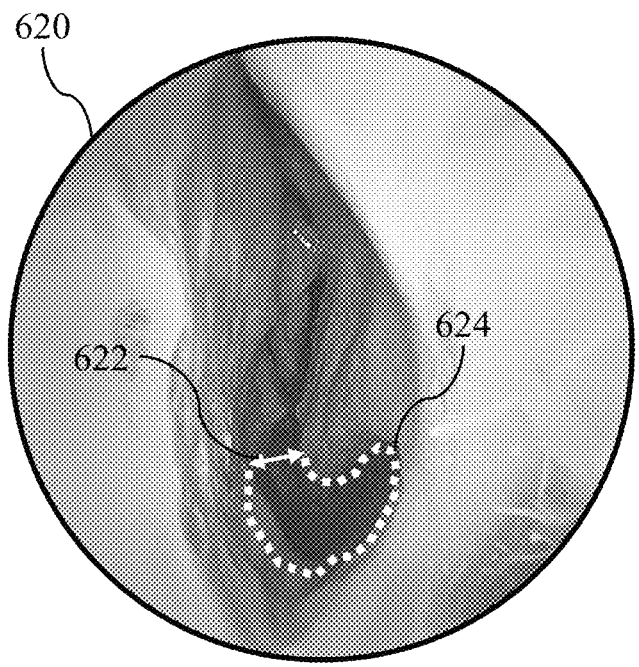
FIG. 9B is a screenshot of an exemplary interface for identifying and defining manual boundaries for selected anatomy.
Figure 14A:
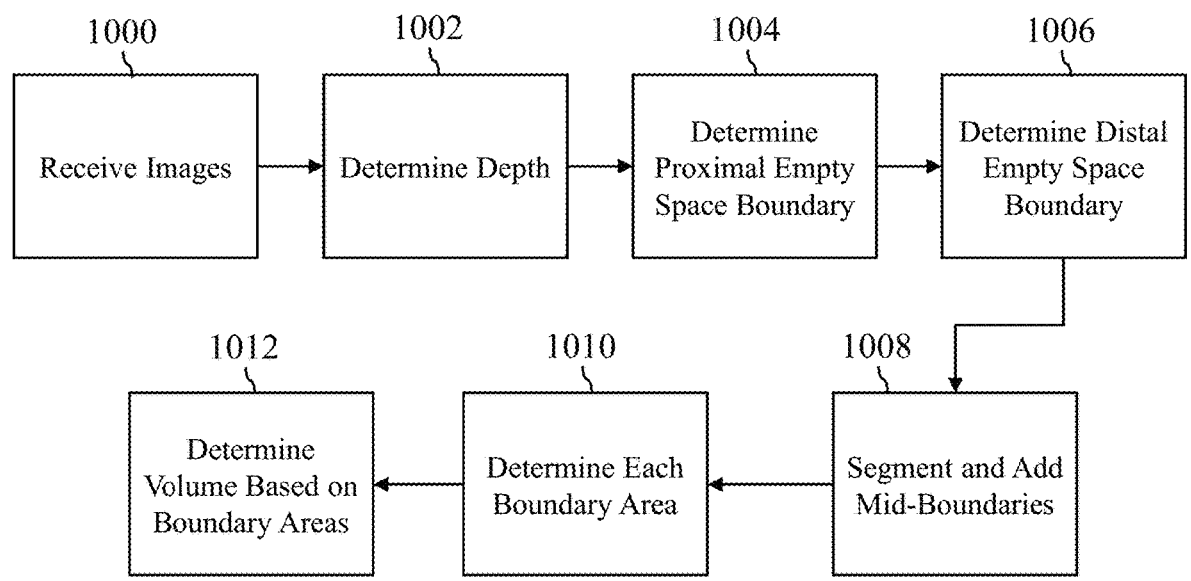
FIG. 14A is a flowchart of an exemplary set of steps that may be performed with the system of FIG. 3 to determine the volume of selected anatomy.
Figure 14B:
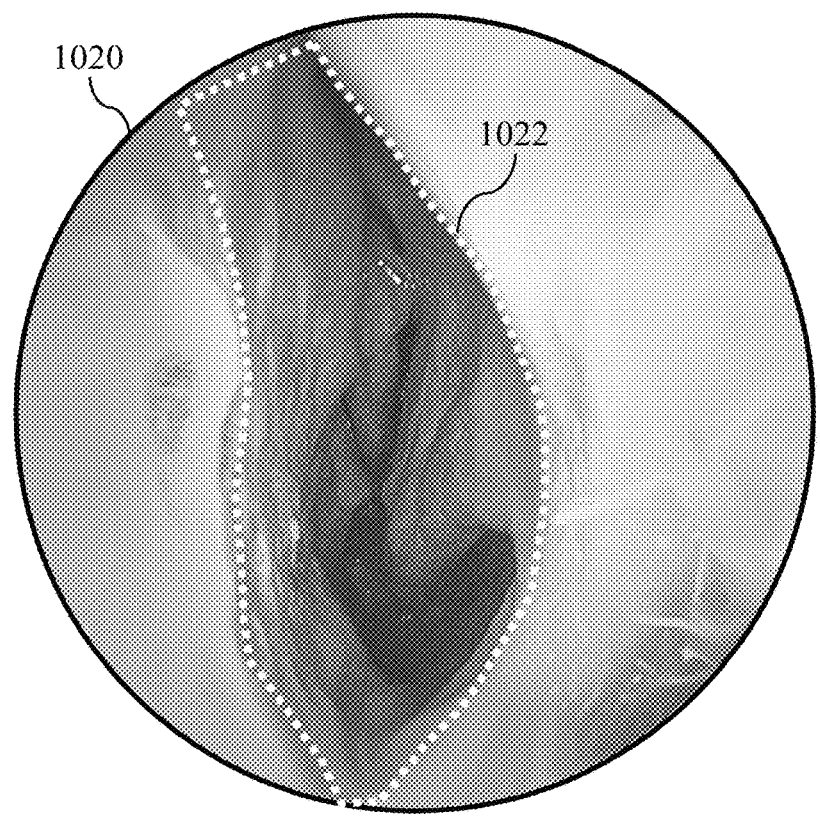
FIG. 14B is a screenshot of an exemplary interface for viewing the volume of selected anatomy at a first step.
Figure 14C:
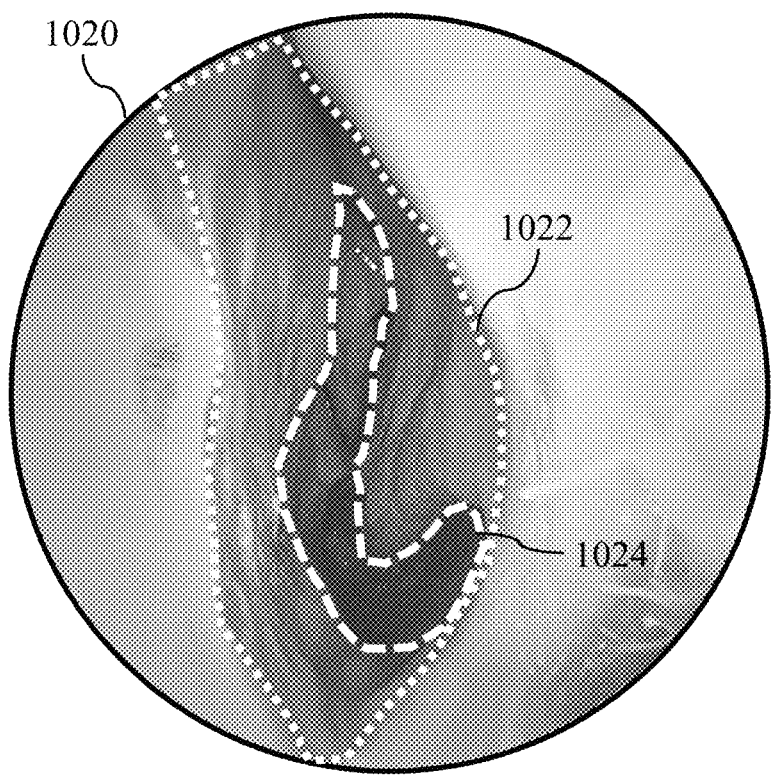
FIG. 14C is a screenshot of the interface of FIG. 14B at a second step.
Figure 14D:
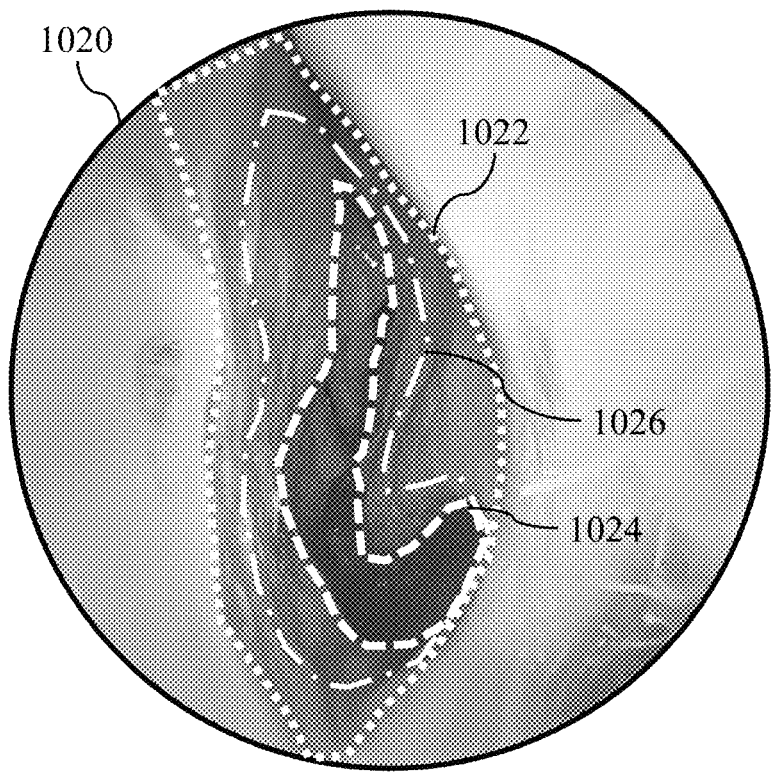
FIG. 14D is a screenshot of the interface of FIG. 14B at a third step.

The system may also receive (608) a manual boundary line from the user, such as by receiving user inputs via the touchscreen display that connect one side of the overlaid boundary (606) with an opposite side, and the system may update (610) the anatomy boundary line and re-display the image with an updated boundary overlay. FIG. 9B shows an example of an interface that may be displayed and used to aid in receiving (602) partial user inputs, identify (604) anatomy, and receive (608) the manual boundary line from the user. An endoscopic image (620) is shown which includes a partial boundary line (624) surrounding empty space just below the inferior turbinate. A manual boundary line (622) is shown, which has been drawn by a user via a touchscreen display, and which limits the boundary line (624) to only the empty space below the inferior turbinate, instead of extending and filling the empty space to the left and above the inferior turbinate (e.g., FIG. 14D shows an example of what a boundary line (1024) for a similar unbounded empty space).

Once the manually bounded area has been determined and updated (610), the system may determine (612) the area within the boundary (e.g., in pixels or another measurement), and may also compare (614) the bounded area to another bounded area that has been previously selected and defined. As an example, this may include where a user selects and/or manually applies a boundary to the empty space, and to another anatomy such as the inferior turbinate (e.g., FIG. 7B illustrates an endoscopic image in a similar state). The system may then notify (616) the user of the size of any bounded area, and/or provide other comparison data. As an example, this might include displaying the area (e.g., in pixels or another measurement) of each bounded area, and displaying comparisons between each bounded area, such as indicating that the bounded area (624) is about 50% of the area of the inferior turbinate. As with prior examples, the interface of FIG. 9B may be shown to a practitioner or patient, and the image or information may also be provided to the imaging server (220), HIS (222), or other devices, as has been described.

Figure 11:
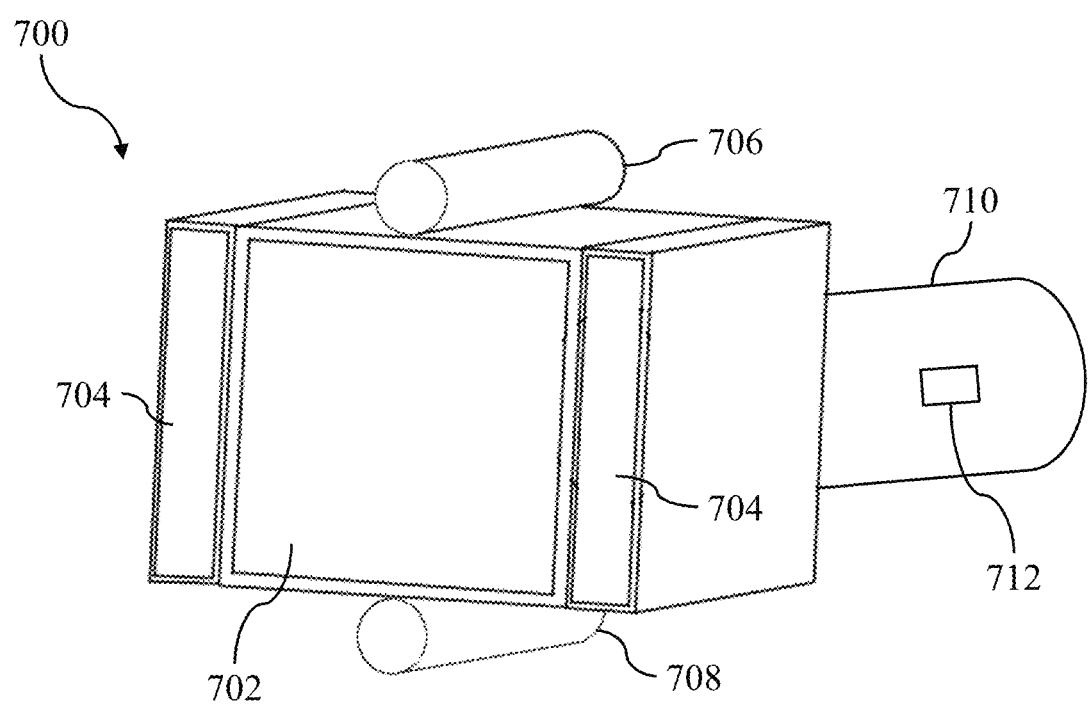
FIG. 11 is a perspective view of an endoscope usable with the system of FIG. 3.

As has been described, an advantageous aspect of the disclosed technology is the use of an endoscope to provide high quality, actionable imaging and analysis related to ENT and other conditions without the cost and complexity of CT, MRI, and other imaging systems. FIG. 11 shows a perspective view of an endoscope usable to provide the disclosed features. The endoscope (700) may be positioned at a distal end of a flexible endoscope line or rigid shaft (710), and may be sized to fit within the nasal canal to varying depths in order to allow endoscopic imaging of the internal anatomy. In some implementations, the endoscope (700) may include a cover material or attachment that covers the edges of the endoscope (700) to aid in insertion and extraction from the nasal canal, such as a soft rubber or plastic cover that includes rounded edges to prevent catching or snagging on nasal anatomy during use.

The endoscope (700) includes an imaging sensor (702) configured to capture sequences of images or video, and transmit captured images or video to a recipient such as the control (216), the imaging device (218), or the imaging server (220) via a data connection within the shaft (710). The imaging sensor (702) may be a single image sensor capable of capturing two dimensional images of anatomy, or may include two or more image sensors offset from each other and/or with non-parallel optical axes to allow for three dimensional imaging of anatomy. One or more lights (704) may be included on the endoscope (700), and may be positioned to the side of and/or behind the imaging sensor (702) to illuminate the target anatomy. The lights (704) may be, for example, LED illuminators operable to emit light at various intensities and colors.

The endoscope (700) may also include one or more spotting devices (706, 708) which may be mounted at various positions on the endoscope. A spotting device (706) may be, for example, a laser light projector, or a patterned light projector capable of projecting a reference light onto the target anatomy. The system may be configured to identify (e.g., using an object recognition process) the presence of a projected reference light within captured images, and to determine additional characteristics of the image based on the reference light. As an example, where the spotting device (706) is a laser light projector, the system may be configured to identify the presence of a red laser dot within a captured image and, based on the diameter or shape of the red laser dot, determine the distance between the imaging sensor (702) and the anatomical surface on which the red laser dot is projected. This may provide a range or depth rating, which may be usable during the disclosed imaging techniques to provide a reference scale for area measurements, such as converting pixels of a bounded area to an area measurement in centimeters. As another example, the spotting device (706) may be a patterned light projector (e.g., such as an LED that projects through a grid or mask) that projects a checkered or lined pattern onto a target surface. The system may use the projected pattern to identify depth and surface topography at various positions within the image, as the pattern will predictably change depending upon the surface that it is projected on (e.g., a square section of light will be distorted into a rectangle or other shape if projected onto a surface that is not entirely perpendicular to the projector).

The endoscope (700) may also include one or more additional sensors (712) that may be mounted on the shaft (710) or other portions of the endoscope (700). Additional sensors (712) may include, for example, accelerometers, gyroscopes, audio sensors (e.g., to capture sounds relating to inhalation and exhalation, and aid in selecting relaxed and inhalation state images), airflow sensors, pressure sensors, and other sensors. Various sensors may be used to assist or enhance some or all of the disclosed features.

As an example, data from accelerometers and gyroscopic sensors may be used to aid in positioning the endoscope (700) and capturing images, and for example may provide warnings to users when motion of the endoscope is detected during imaging. This may be useful for disclosed techniques which include comparisons between sequences of images (e.g., such as the steps of FIGS. 4 and 5), since movements of the imaging sensor (702) between comparison images may complicate the comparison process. In some implementations, the system may use feedback from an accelerometer to aid in image stabilization between captured images. As an example, in such implementations the system may be configured to, between concurrent images, detect a change in the perspective of the imaging sensor (702) as a result of movement, and may be configured to correct images prior to comparison or analysis to maintain a consistent perspective through small changes (e.g., where a first image is captured, and then the imaging sensor (702) is withdrawn slightly from the nasal cavity, the system may be configured to ignore the outside edge of the subsequent image which was not included in the prior image). In such implementations, feedback from an accelerometer or gyroscope may be used to more accurately aid in image stabilization and comparison.

As another example, airflow sensors and/or pressure sensors may be included on the endoscope (700) and configured to measure the flow of air around the endoscope (700) and/or the pressure within the nasal cavity. Some conventional approaches to diagnosing nasal valve collapse and other ENT conditions utilize airflow and pressure measurements to determine whether nasal valve collapse is occurring, where a pressure during inhalation above a certain threshold indicates nasal valve collapse. In implementations that include a pressure and/or airflow sensor on the endoscope (700), pressure based measurements relating to nasal valve collapse may also be captured at the same time that imaging is being performed, with the combined results being displayed to a user of the system as will be described in more detail below.

Figure 12A:
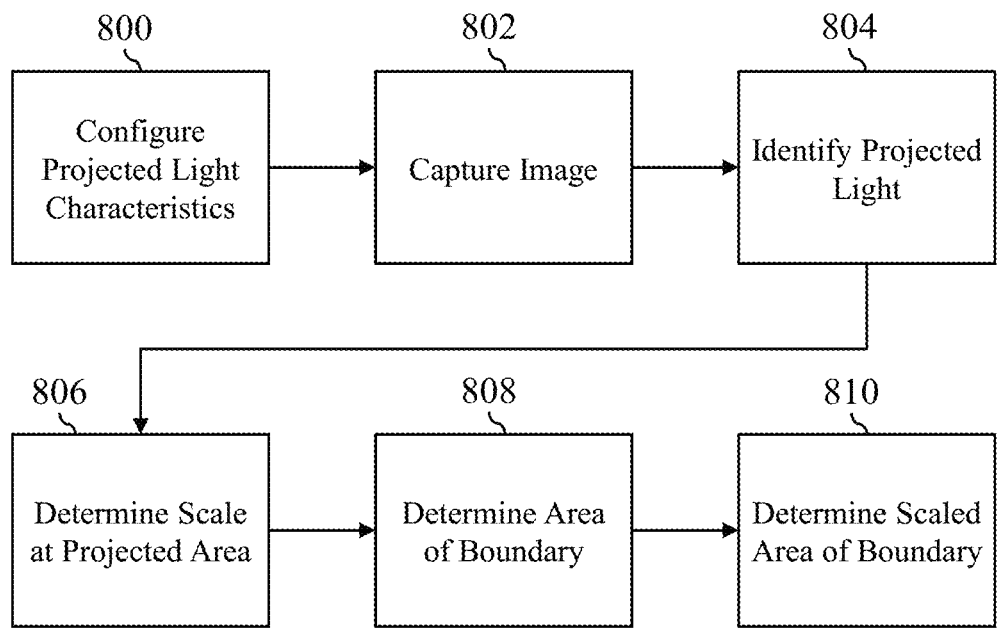
FIG. 12A is a flowchart of an exemplary set of steps that may be performed with the system of FIG. 3 to determine the area of selected anatomy.

The endoscope (700) is show including a spotting device (706) mounted near the imaging sensor (702) opposite another spotting device (708). In implementations with such a configuration, a dual spotting light, such as a laser light, may be projected onto the target anatomy to aid in providing scale to captured images. As an example, FIG. 12A shows a set of steps that may be performed to determine the scaled area of selected anatomy. Steps such as those shown in FIG. 12A may be performed with any other steps that include designating bounded areas within an endoscopic image, and determining the area within the boundary in pixels, for example. As has been described, the system may be configured (800) with information on characteristics of the projected light. Such configurations will vary by implementation, but may include a description of the pixel-diameter of the projected dot at various distances (e.g., at a 1 inch projection distance, the resulting laser dot will be 20 pixels wide, which corresponds to 1 millimeter, when captured by the image sensor (702), and so on for each of a variety of projection distances), or the shape of the projected dot or pattern when projected onto a flat perpendicular surface.

With the dual spotting (706, 708) configuration of the endoscope (700), the configured (800) characteristics may include the offset between the two projected lights (e.g., when projected onto a surface, the distance between the two projected lights will be substantially static and may be, for example, 1 millimeter). When projected onto a surface at any range, the static offset distance may be used to provide a scale reference for the target surface (e.g., while the laser dots may appear smaller and closer together when projected onto a distance surface, the offset between dots may be still be determined as 1 millimeter).

Figure 12B:
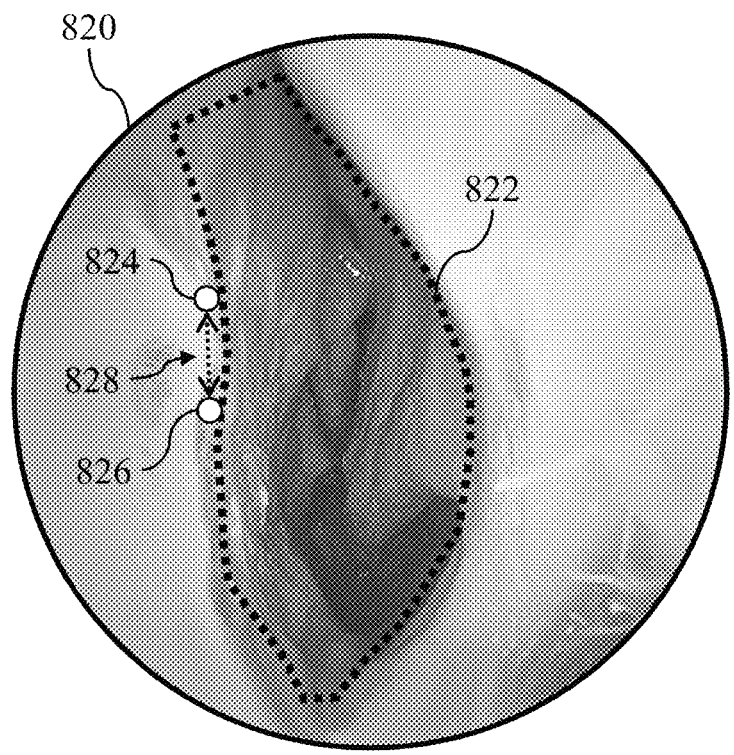
FIG. 12B is a screenshot of an exemplary interface for providing and determining the area of selected anatomy.

During imaging of anatomy, the system may capture (802) sequences of images or video, and may identify (804) the projected light within the images using an object recognition process. The system may then determine (806) the scale of the projected area based upon the appearance of the projected light at that area and the configured (800) characteristics. Where the area that the spotting light is projected at corresponds to a particular anatomy or boundary area, the system may then determine (808) the area of that boundary, as has been previously described, and then may determine (810) the scaled area of that boundary by converting between a calculated pixel measurement and a scaled measurement (e.g., where 20 px corresponds to 1 millimeter, a calculated boundary area of 40,000 px$^2$ may be determined to be 100 mm$^2$). FIG. 12B provides an example of an interface usable to align a pair of spotting lights (824, 826) with a bounded area in order to determine the scaled area within the boundary. An endoscopic image (820) is shown that includes a bounded area (822) corresponding to the proximal opening of the nasal valve, as may be determined and overlaid during steps such as those of FIG. 4. By positioning the endoscope (700) to substantially align the spotting lights (824, 826) with a border of the bounded area (822), the system may use the configured offset between spotting lights (822) to determine the scaled length of that section of border, which may then be extended and applied to the entire bounded area (822) to determine its perimeter, area, or other scaled physical characteristics. The pattern of the light also similarly can be used to determine the scaled factor and determine any of the above parameters in any units as required by the user. Knowing the scale factor, can be used to translate a picture dimension in pixels to units such as meters, inches etc. since the distance between the lights is known on the scope allowing to accurately determine the shrinking factor of the image.

Figure 13A:
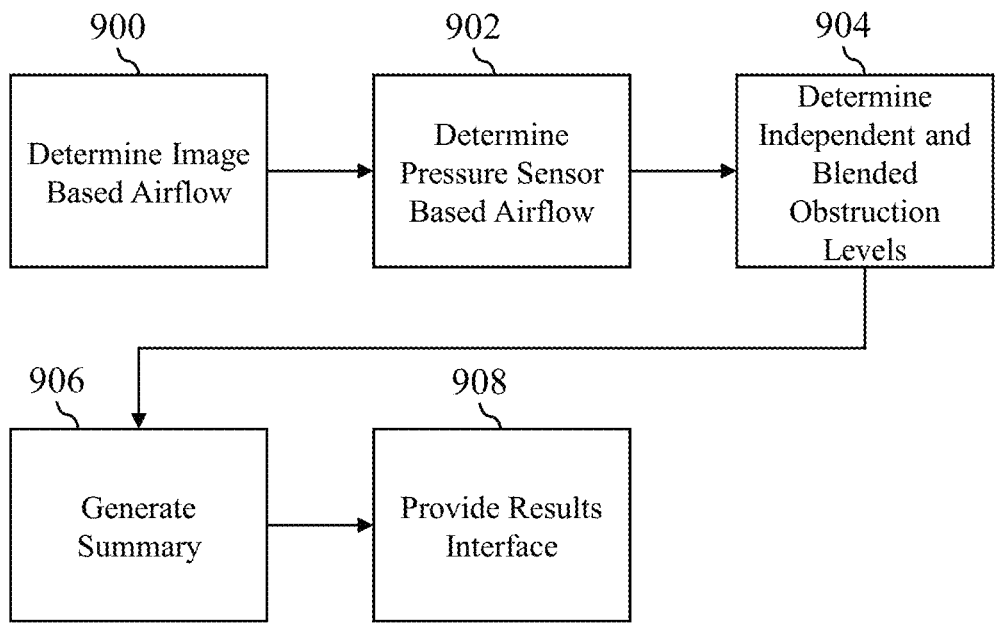
FIG. 13A is a flowchart of an exemplary set of steps that may be performed with the system of FIG. 3 to provide image and sensor based airflow measurements.

As has been described, some implementations of the endoscope (700) may include an airflow and/or pressure sensor (712) usable to measure and provide additional metrics related to nasal valve collapse and other ENT conditions. FIG. 13A shows a set of steps that may be performed provide both image and sensor based airflow measurements. The system may determine (900) an image based airflow measurement by performing steps such as those of FIG. 4, and may also receive airflow and pressure measurements usable to determine (902) a pressure based airflow measurement by calculating the pressure within the nasal canal during a certain airflow. The system may then determine (904) separate obstruction levels based on those metrics, as well as blended obstruction levels that combine aspects of those metrics. The system may then generate (906) a summary using the separate and/or blended obstruction levels, and may provide (908) that summary via an interface to a practitioner and/or patient, or provide the summary to the HIS (222) or another device, as has been described.

Figure 13B:
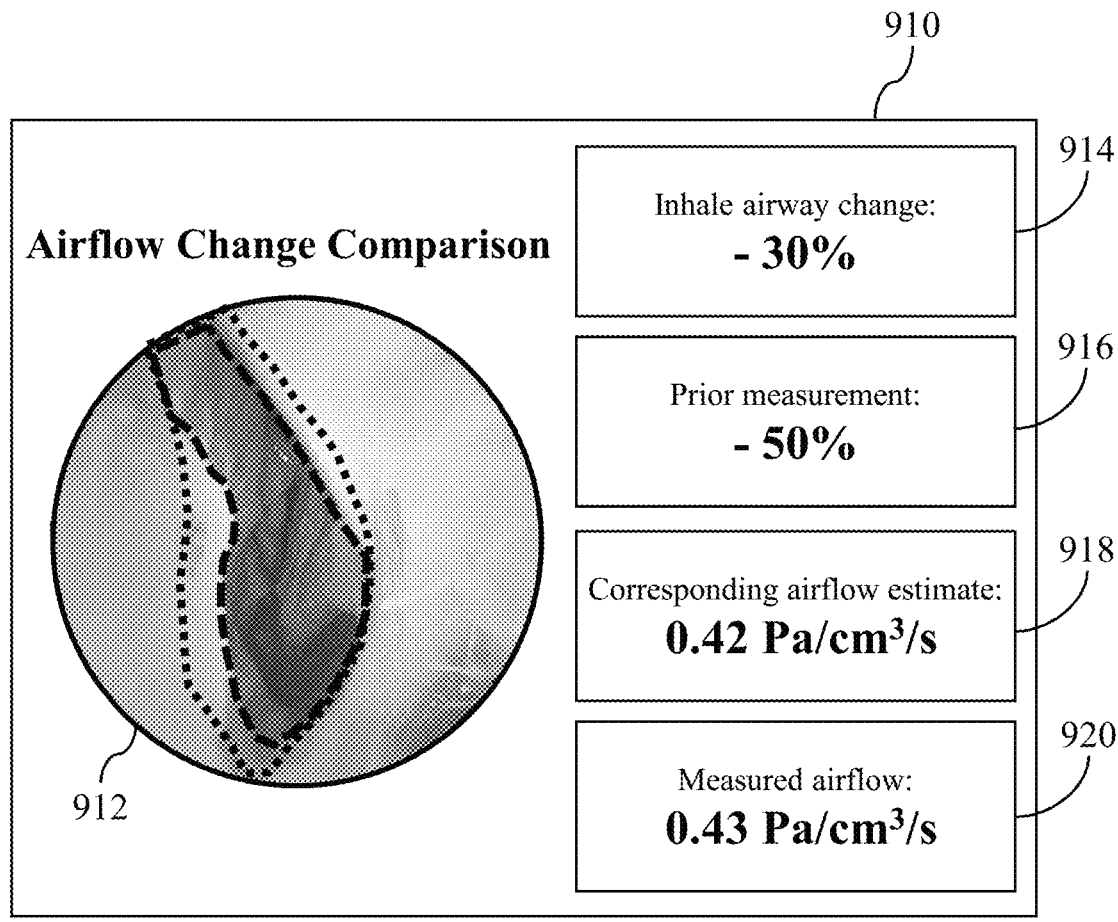
FIG. 13B is a screenshot of an exemplary interface for viewing image and sensor based airflow measurements.

FIG. 13B shows a screenshot of an interface (910) for viewing image and sensor based airflow measurements such as may be provided (908) during the steps of FIG. 13A. The interface (910) includes an endoscopic image (912) such as that shown in FIG. 6C, which includes boundary lines showing the maximum size of the nasal valve opening during a relaxed state, and the minimum size of the nasal valve opening during forceful inhalation. The interface also includes an airway change (914) which describes the change in calculated area between the maximum and minimum airway openings, and a historical comparison (916) showing the results of a prior measurement (e.g., a prior measurement may have shown a 50% reduction in the airway during inhalation, while the current post-procedure comparison is 30%). The interface (910) also includes an estimated airflow (918) that is calculated based only upon the image analysis of the airway, which may be calculated using a lookup table that relates various changes in the area of the airway to corresponding pressures, for example. The interface (910) also includes an actual measured airflow, based upon data measured (902) from the airflow and/or pressure sensor. In this manner, the interface (910) provides several comparable metrics for determining airflow and identifying the presence of ENT characteristics such as nasal valve collapse, which may advantageously be gathered and determined simultaneously using the endoscope (700).

The systems and techniques described herein may also be implemented to provide volume measurements of imaged anatomy. As an example, FIG. 14A shows a set of steps that may be performed to determine the volume of selected anatomical structures or areas. As images are received (1000), the system may determine (1002) a depth or distance from the endoscope (e.g., from the imaging sensor (702), a distance measuring sensor to determine the depth at one or multiple points or other forms of contour anatomical sensing technologies). A determination of depth (1002) may be made using 3D imaging techniques, such as an imaging sensor (702) that includes multiple offset imagers, or a depth finding feature using projected laser light, projected patterns, or other optical depth indicators, as has been previously described. The determination of depth (1002) may also be made without 3D cameras or optical range finders using the object recognition process, which may analyze the image and determine the depth of different areas based upon visual characteristics such as colors, shapes and positions of anatomical structures, and other information.

The system may then determine (1004) a boundary for a proximal empty space or anatomical structure, and determine (1006) a boundary for a distal empty space or anatomical structure using one or both of object recognition data and depth data. FIG. 14B is a screenshot of an interface for determining and viewing volume of a selected portion of the image (e.g., an empty space or anatomical structure). An endoscopic image (1020) is shown, over which a proximal boundary line (1022) is overlaid. The proximal boundary line (1022) may be determined as previously described, and may include a combination of partial user input, object recognition, and manual user adjustment. FIG. 14C shows the image (1020) with a distal boundary line (1024) overlaid, which may be determined as previously described.

The system may then determine (1008) one or more mid-boundaries of the anatomical structure or space that are present between the proximal boundary and distal boundary which, in effect, segments the two-dimensional image into a number of layers that may be interpreted as three-dimensional space. A higher number of mid-boundaries (e.g., corresponding to different layers) will provide a more accurate measurement of volume. FIG. 14D shows the image (1020) with the proximal (1022) and distal boundary lines (1024), and also includes a mid-boundary line (1026). As with prior examples, each boundary may be determined automatically, or based upon partial user inputs and user adjustments, as has been described. With at least two, but ideally three or more bounded areas, the system may then determine (1010) the areas (e.g., in pixels, or in a scaled measurements, as has been described) for each two dimensional boundary, and then determine (1012) a three dimensional volume based on the multiple two-dimensional areas. As one example, the system may determine (1012) a volume by associating a depth with each segment or bounded area. With reference to FIG. 14D, each bounded area may have a measured or estimated depth of 10 millimeters. The proximal boundary (1022) may have an area of 800 mm$^2$, the mid-boundary (1026) may have an area of 600 mm$^2$, and the distal boundary (1024) may have an area of 300 mm$^2$. In the above example, the system may then determine the volume of the empty space to be the sum of 8000 mm$^3$, 6000 mm$^3$, and 3000 mm$^3$ (e.g., the sum of the calculated volume of each segment with an estimated depth of 10 mm). As can be seen, with the presence of additional mid-boundaries, the depth of each may be reduced (e.g., from 10 mm to 5 mm, 2 mm, or fractions of a millimeter), allowing for "higher resolution" and more accurate measurements of volume.

As has been previously described, some level of pre-processing of captured images and video may be performed to aid in identification of certain anatomical structures and areas. As an example, with reference to FIG. 6A, it can be seen that deeper areas within the nasal canal and distal empty areas of the nasal canal are darker, and less illuminated than proximal areas where the light from the endoscope is most visible. As a result, where the anatomical area in question is deep within the nasal canal, it may be advantageous both for the user, as well as for an object recognition process, to adjust the image prior to display and/or analysis in order to further differentiate proximal and distal anatomy based upon their color and/or brightness. This may allow the user to more accurately provide partial user inputs, as the boundary lines of the selected anatomical structure may be more clearly defined post-processing, and in turn allow the object recognition process to receive higher quality partial user inputs, and to make higher quality comparisons to its own dataset.

Figure 15A:
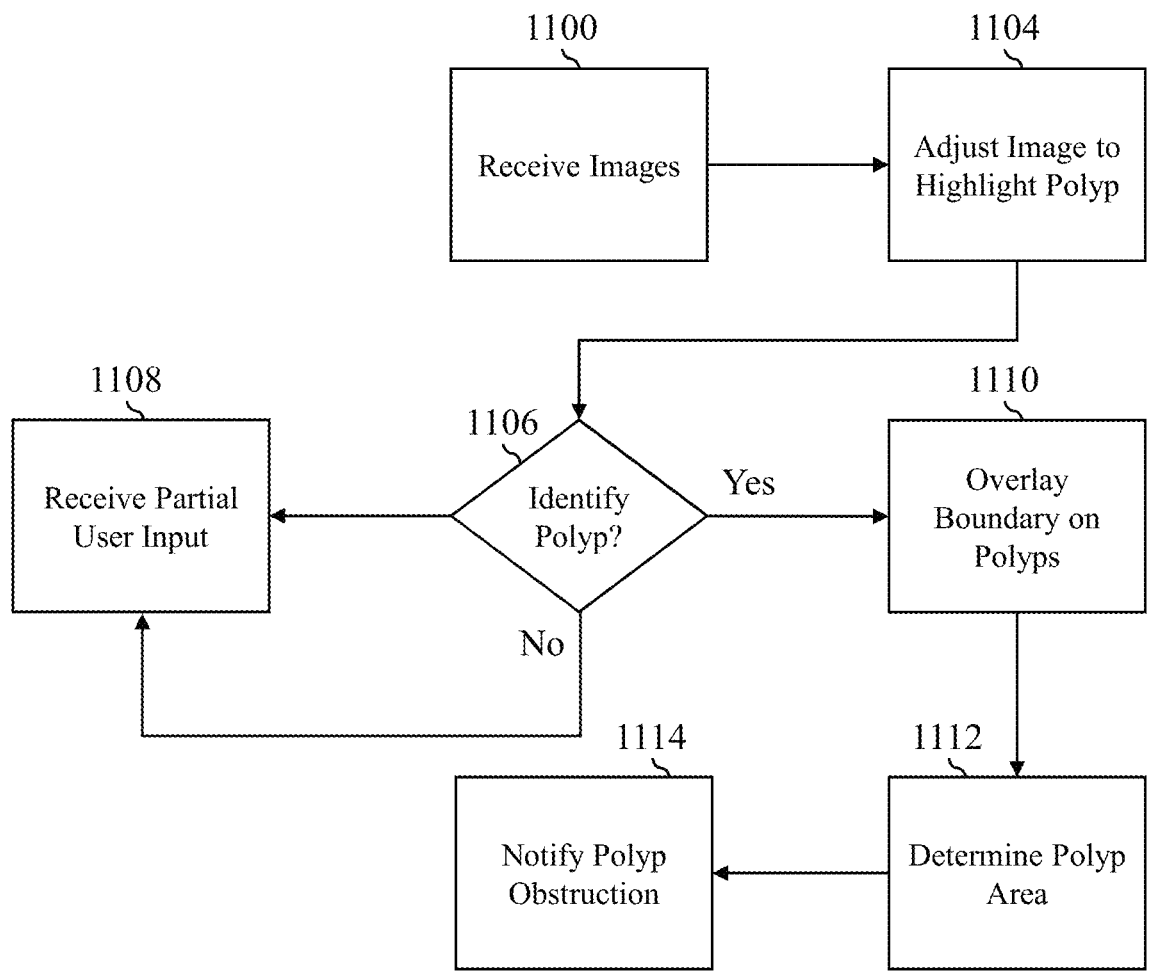
FIG. 15A is a flowchart of an exemplary set of steps that may be performed with the system of FIG. 3 to identify and view polyps.

The above is especially true for some ENT conditions that are associated with highly visible and distinguishable color or visible presence as compared to surrounding tissues, with one such example being nasal polyps. Nasal polyps may occur at various areas within the nasal canal, and will typically be much lighter in color as compared to surrounding tissues. FIG. 15A shows a set of steps that may be performed to identify and view polyps based upon imaging with an endoscope. As images are received (1100), the images may be adjusted (1104) to highlight portions within the image that may be nasal polyps, and the system may attempt to identify (1106) the polyps using an object recognition process, which may also include receiving (1108) partial user inputs defining the boundary of the polyp (e.g., via a touchscreen input, or otherwise), as has been previously described. Once identified (1106), the system may overlay (1110) a boundary on one or more polyps within the image, determine (1112) the area and/or volume of the one or more polyps (e.g., such as by determining the two dimensional pixel area or scaled area, or determining the three-dimensional volume of multiple segments in pixel or other scaled measurement), and notify (1114) the user of the results of such analysis, as has been previously described.

Figure 15B:
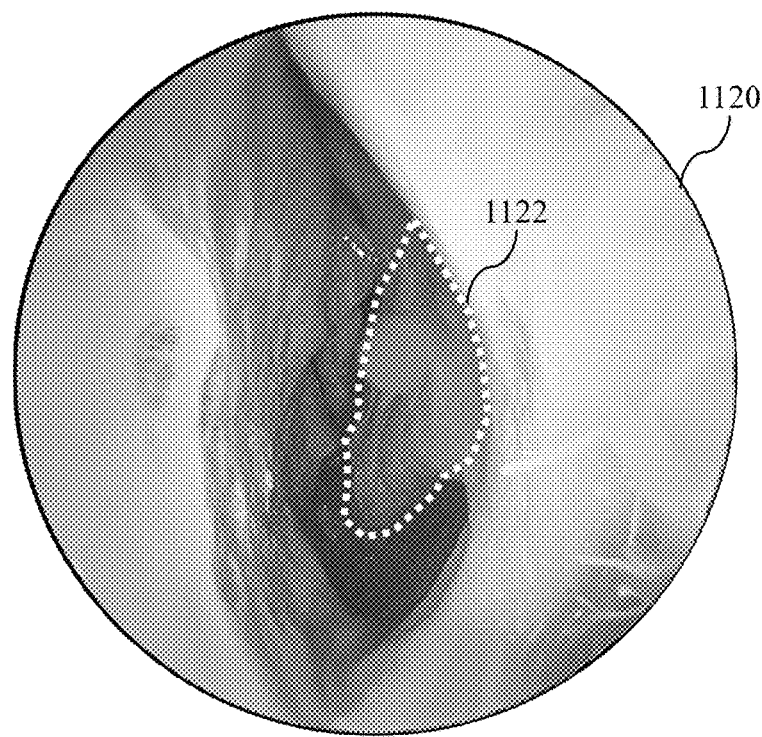
FIG. 15B is a screenshot of an exemplary interface for identifying and viewing polyps.
Figure 15C:
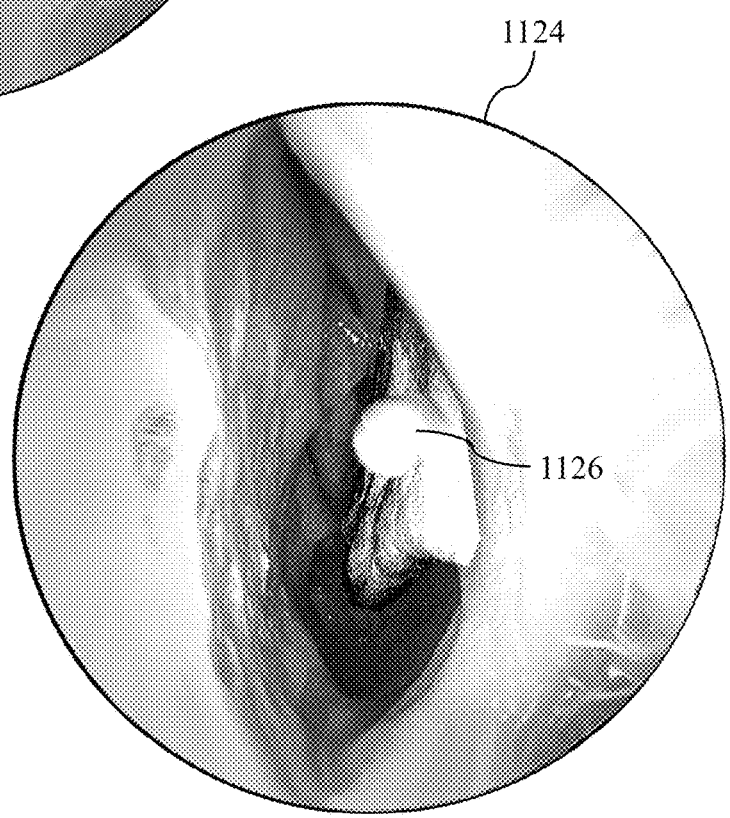
FIG. 15C is a screenshot of the interface of FIG. 15B at a subsequent step of identifying and viewing polyps.

As an example of the above, FIG. 15B a screenshot of an interface usable to identify polyps. An endoscopic image (1120) is included, and a boundary line (1122) is present on the inferior turbinate. While the boundary line (1122) is not required, a particular area of the image may be selected by the user, or identified by the system, as an area where polyps occur, and the image adjustment (1104) and poly identification may be confined to that area, with empty space and other sections being largely excluded. FIG. 15C shows an adjusted image (1124) that has been modified to highlight the presence of a polyp (1126) on the inferior turbinate. Using the adjusted image (1124), a user may begin to draw a boundary line around the polyp (1126), which is now more visually distinguishable from health portions of the inferior turbinate, and the system may identify (1106) the polyp using an object recognition process based in part upon the received (1108) partial user input.

Figure 16A:
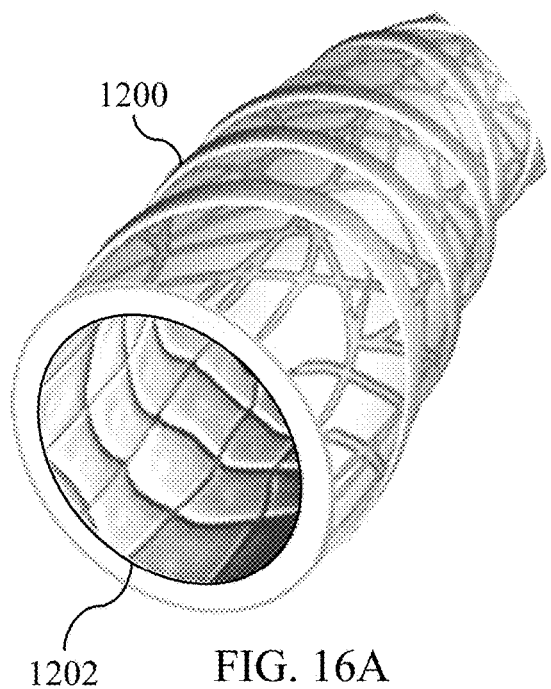
FIG. 16A is a schematic diagram showing an internal airway of a bronchial tube.
Figure 16B:
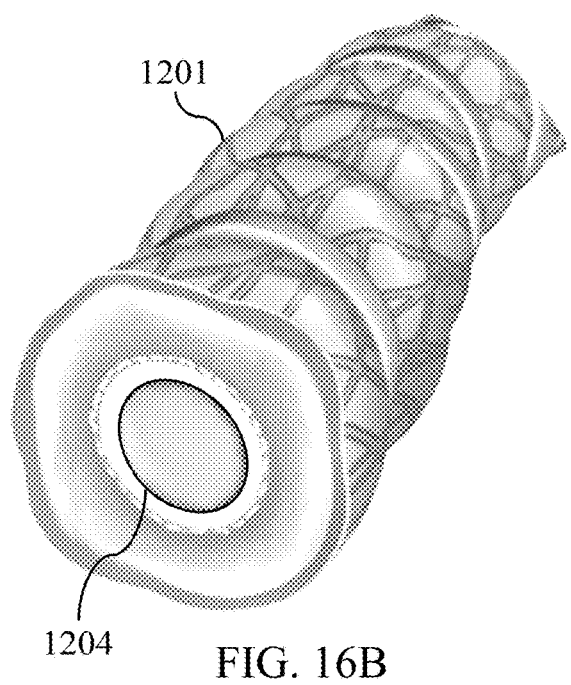
FIG. 16B is a schematic diagram showing an internal airway of a bronchial tube with inflammation.
Figure 16C:
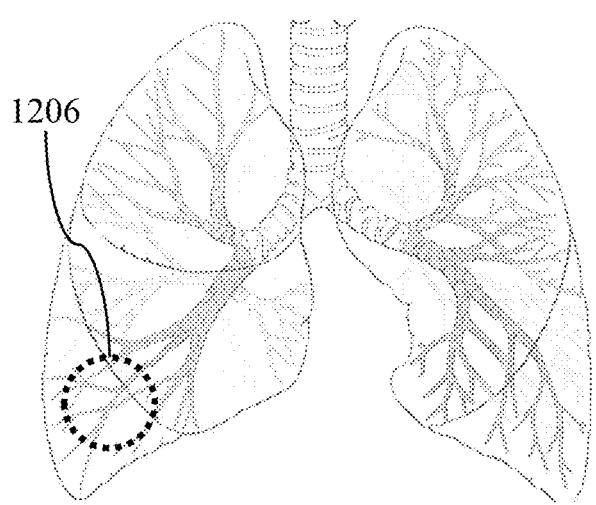
FIG. 16C is a schematic diagram showing a position within the lungs where inflammation of a bronchial tube may occur.

While much of this disclosure has been in the context of ENT procedures and uses, it should be understood that many of the disclosed features, such as fully or partially automated identification of certain anatomy (302), receiving (304) and using partial user input to aid in identification, overlaying (306) and adjusting (308) visual boundaries on graphical interfaces depicting endoscopic images of anatomy, and others. As an example, some implementations of the disclosed technology may be configured to aid in the identification and analysis of bronchial tube inflammation such as may be caused by chronic bronchitis. FIGS. 16A through 16B show schematic diagrams that illustrate a healthy bronchial tube (1200), an inflamed bronchial tube (1201), and a location (1206) in the lungs where bronchial inflammation may be identified by the system. In particular, the disclosed endoscope and system may be used to identify and provide information on the level of bronchial inflammation present based upon comparisons between the contours (1202, 1204) at multiple points in the airway.

Figure 17A:
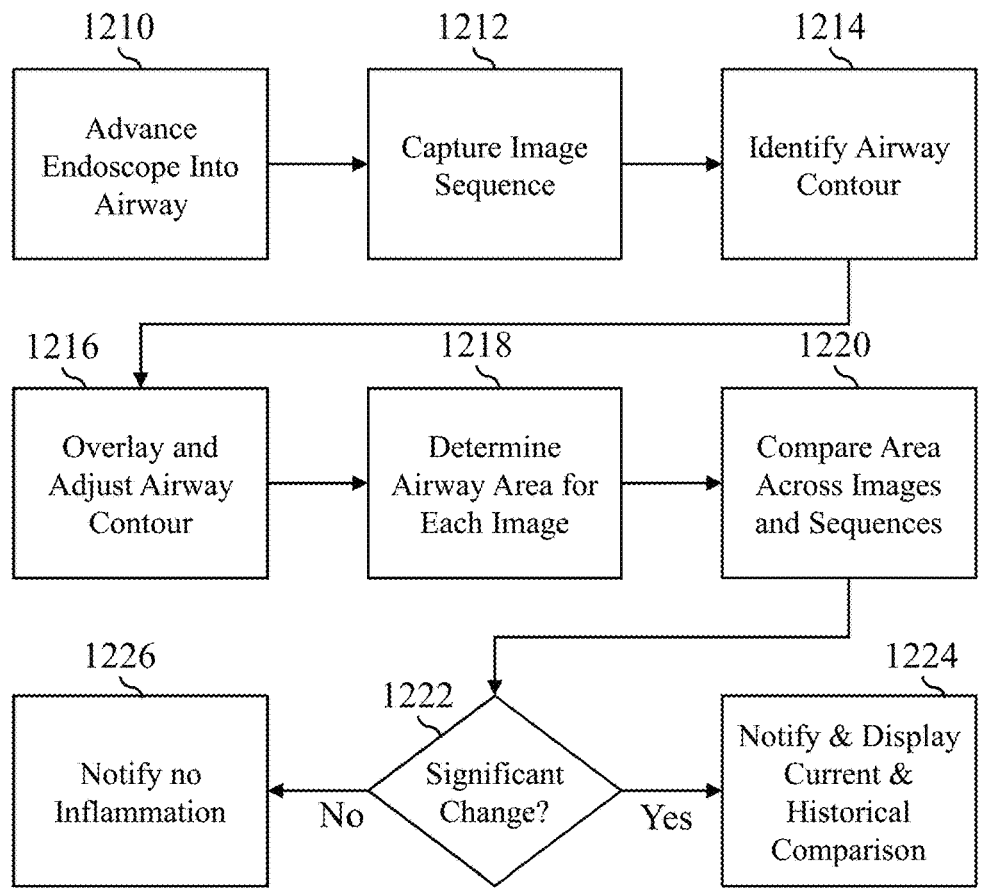
FIG. 17A is a flowchart of an exemplary set of steps that may be performed with the system of FIG. 3 to identify inflammation of a bronchial tube.

As an example, FIG. 17A shows a set of steps that may be performed to identify inflammation of a bronchial tube. An endoscope may be advanced (1210) along the bronchial tube while a sequence of images is captured (1212). Advancement (1210) of the endoscope may be aided by guidance provided via the imaging device (218) or another display, which may use feedback from an accelerometer or other sensor within the endoscope (212) to provide instructions to a user for controlling the speed and extent of advancement (1210). As an example, the software may display messages to the user indicating that the endoscope (212) should be advanced or retracted, or that the speed of advancement (1210) of the endoscope (212) should be increased, decreased, or maintained (e.g., if captured images are blurry or unfocused, instructions may be provided to slow down to improve image quality, if captured images are focused and high quality instructions may be provided to speed up to improve procedure time and patient comfort). Information from an accelerometer may also be used to provide reference points between images of the sequence, indicating the change in position along the airway between each image.

Figure 17B:
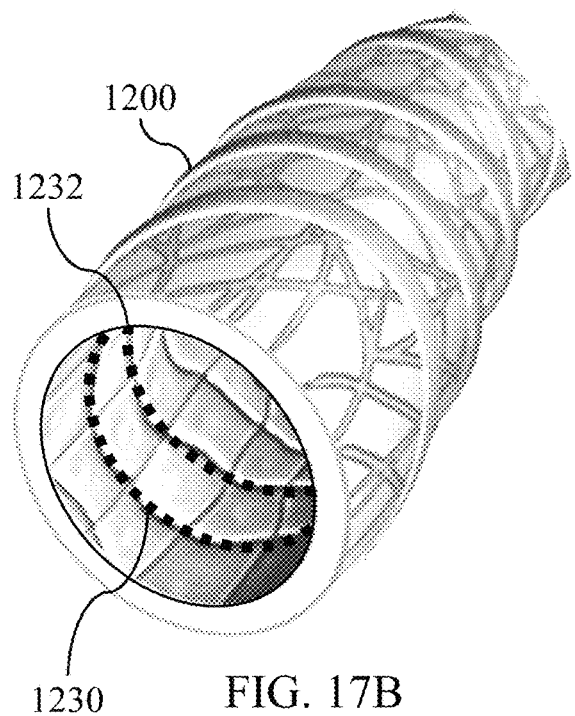
FIG. 17B is a screenshot of an exemplary interface for identifying inflammation of a bronchial tube.

For each of the captured (1212) images, the system may identify (1214) the two dimensional contour of the airway at multiple points, and overlay (1216) and allow adjustments to a visual boundary along the identified (1214) contour. As with prior examples, this may include fully or partially automated identification of the anatomy using an image recognition process, partial user inputs, and user adjustments, as has been previously described. The system may then determine (1218) the area of the airway for each image of the sequence based on the bounded area, in pixels or another unit of measurement, and may compare (1220) the area of the airway across multiple images of the sequence to determine whether significant changes (1222) in the area of the airway occur. As with prior examples, a significant change (1222) may be determined based upon a configured threshold of change from one image of the sequence relative to another. Comparison (1220) of the images may occur strictly based upon image sequence (e.g., compare each image to the immediately subsequent image, or compare an average area of 10 images to the next 10 images of the sequence, etc.), or may also be based information from an accelerometer or other position sensor (e.g., compare images that are separated by 1 millimeter of advancement of the endoscope).

Where a significant change exists (1222), the system notify (1224) the user of the change and display images and information describing current and historical comparisons of the airway, as has been previously described. This may include overlaid images showing the change in area of the airway between current images, or between a current image and a historic image, may include information describing the percentage in decrease of area of the airway per 1 millimeter of advancement, or may include information describing the average area of the airway compared to that of a healthy airway, for example. Where no significant change (1222) is detected, the system may notify (1226) the user that no inflammation is detected, and may provide visual images, comparative images, and other comparative information, as has been described. As with prior examples, in each case images and information may be displayed via the imaging device (218), provided to the imaging server (220), and provided to the HIS (222). FIG. 17B is a screenshot of an interface that may be displayed while identifying inflammation of a bronchial tube, and shows an image of the tube (1200) and overlaid boundaries (1230, 1232) indicating the contour of the tube (1200) at various points, with each bounded area being usable by the system to determine a cross sectional area at that point of the tube. The interface of FIG. 17B may be displayed as endoscopic images of the bronchial tube with included overlaid boundaries, or may be displayed as a rendered three dimensional model or simulation of the bronchial tube that is created by combining the sequence of images, and may be interacted with by a user to provide partial user inputs to aid in identification of contours, or to adjust overlaid boundaries, as has been described.

Figure 18A:
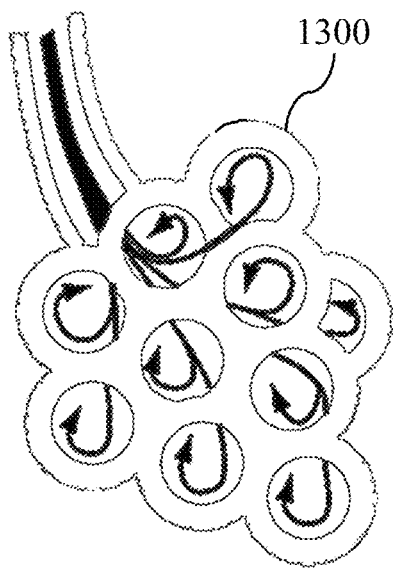
FIG. 18A is a schematic diagram showing a healthy lung alveoli.
Figure 18B:
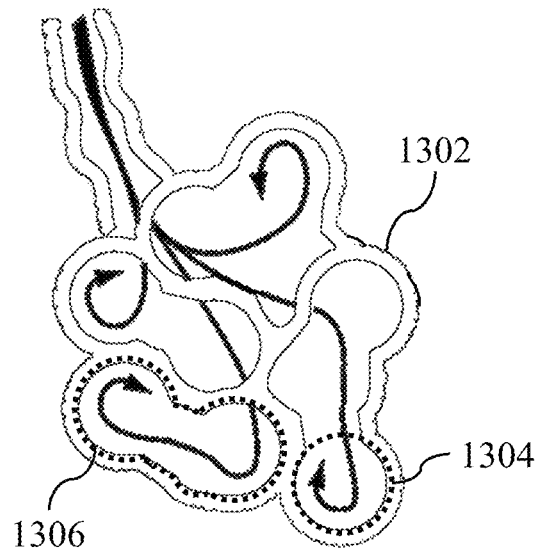
FIG. 18B is a schematic diagram showing a diseased lung alveoli.

As another example of a feature or mode that the system can operate in, some implementations of the system may be usable to aid in identifying and analyzing diseased lung alveoli. FIG. 18A illustrates an example of healthy alveoli (1300), while FIG. 18B illustrates an example diseased alveoli (1302), from a perspective such as may be captured by an endoscope of the disclosed system. As can be seen in FIG. 18B, the empty space within alveoli is expected to have a roughly circular shape (1304), but within diseased alveoli the empty space can instead be an irregular shape (1306).

Figure 18C:
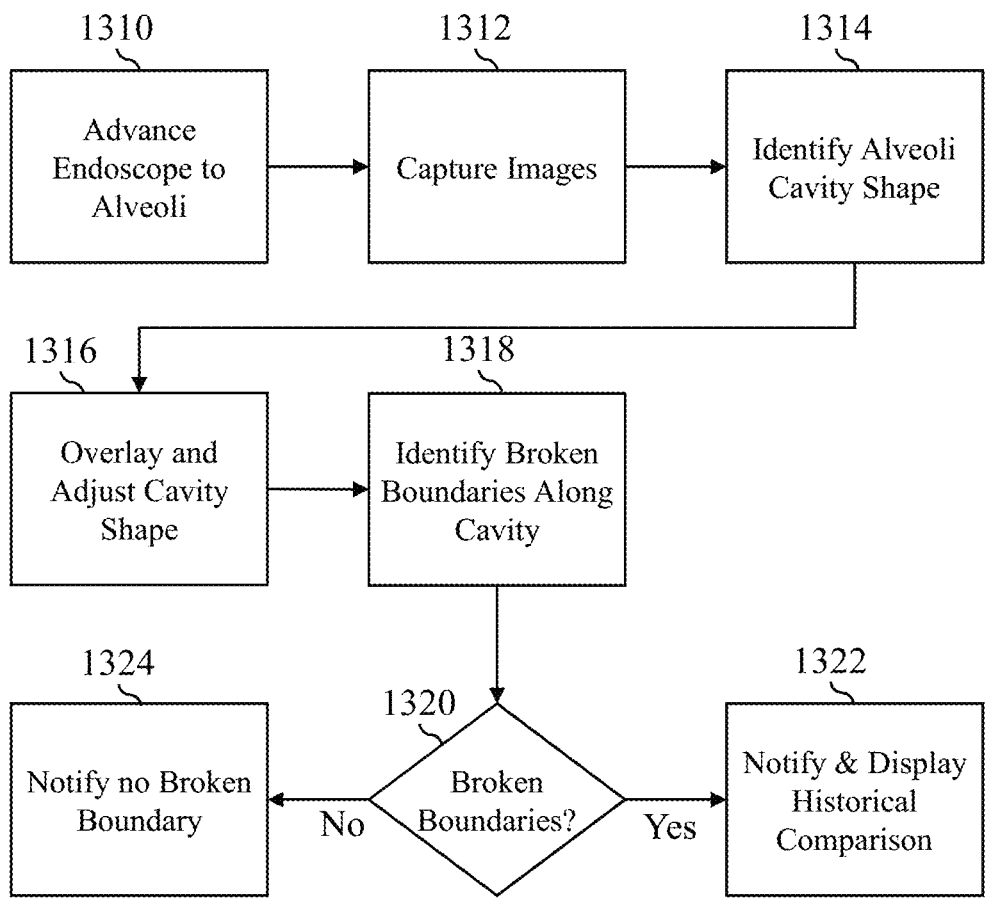
FIG. 18C a flowchart of an exemplary set of steps that may be performed with the system of FIG. 3 to identify diseased lung alveoli.

FIG. 18C shows a set of steps that may be performed to identify diseased lung alveoli based upon imaging such as that depicted in FIGS. 18A and 18B. The endoscope may be advanced (1310) to the alveoli, and images may be captured (1312). The system may identify (1314) the alveoli cavity shape or empty space, and may overlay (1316) and allow adjustment to a visual boundary around the empty space of each alveoli, which may include identification by an object recognition process, receiving partial user inputs to aid in identification, and manual user adjustments to automatically overlaid boundaries, as has been previously described. The system may then automatically identify (1318) broken boundaries within the identified cavities by analyzing the bounded area to determine whether its shape is within a configured threshold of similarity to an expected shape (e.g., such as the bounded area 1304), or whether the shape of bounded area is irregular (e.g., such as the irregular bounded area (1306)). Where broken boundaries are present (1320), the system may notify (1322) the user via the imaging device (218) or another device and display current images and overlaid boundaries that are broken, comparative historical images, and other information. Where no broken boundaries exist (1320), the system may notify (1324) the user that no broken boundaries exist, and display images and information illustrating the healthy alveoli and/or any alveoli that are irregular but still below the threshold of being considered broken boundaries. As with prior examples, images and information may be provided to the image device (218), imaging server (220), or HIS (222), as has been previously described.

Figure 19A:
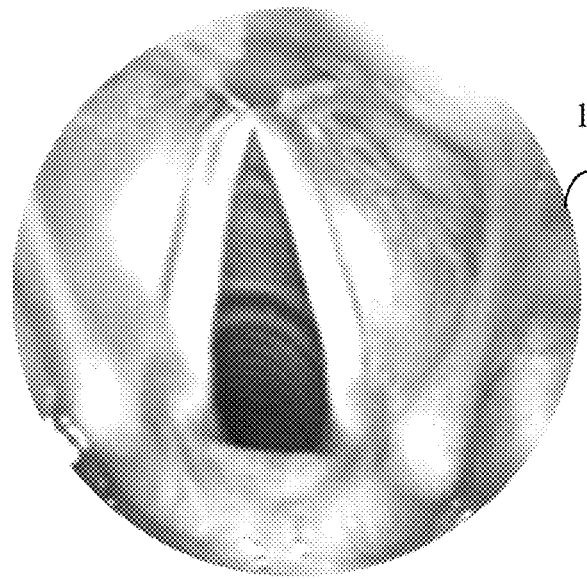
FIG. 19A is an endoscopic image of a healthy trachea.
Figure 19B:
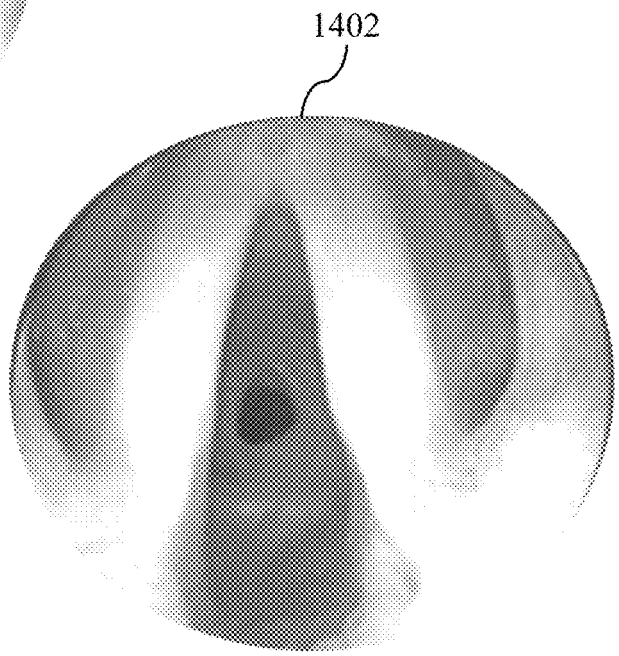
FIG. 19B is an endoscopic image of a trachea with stenosis.
Figure 19C:
FIG. 19C is an endoscopic image of a trachea after a procedure to correct stenosis.

As another example of a feature or mode that the system can operate in, some implementations of the system may be usable to aid in identifying and analyzing the presence of tracheal stenosis prior to and after a procedure to correct the tracheal stenosis. Tracheal stenosis is a condition that describes narrowing of the trachea due to scar tissue or other malformed tissue. FIG. 19A is an endoscopic image of a healthy trachea (1400), while FIG. 19B shows a trachea with stenosis (1402), and FIG. 19C shows an image of a trachea (1404) after a procedure to repair tracheal stenosis.

Figure 20A:
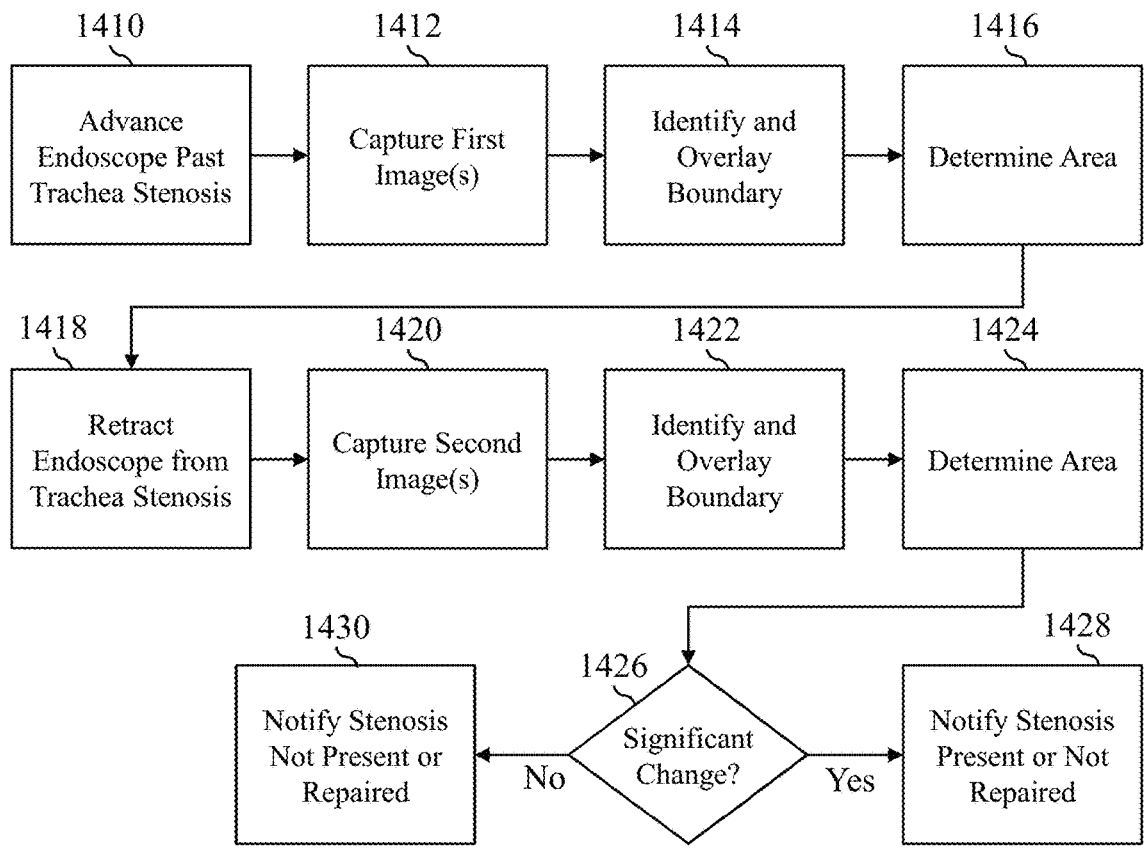
FIG. 20A is a flowchart of an exemplary set of steps that may be performed with the system of FIG. 3 to identify stenosis and evaluate the results of a procedure to repair stenosis.

FIG. 20A shows a set of steps that may be performed to identify stenosis and evaluate the results of a procedure to repair stenosis. The system may guide the user, via the software interface, to advance (1410) the endoscope past the tracheal stenosis (e.g., guidance may include instructions to advance the endoscope until the stenosis is detected by an object recognition process, and then to continue advancing the endoscope until the stenosis is no longer detected, and such guidance may also be based upon accelerometer or other sensor data to guide the direction and speed of movement, as has been previously described).

A first image or set of images may then be captured (1412) by the endoscope, and the system may identify (1414) and overlay visual boundaries over the contours of the trachea opening past the stenosis. As with prior examples, identification (1414) of the contour of the trachea may be performed using an object recognition process, partial user inputs to aid in identifying the contour, and manual user adjustments to an automatically applied boundary, as has been previously described. The system may then determine (1416) the area of the airway in pixels or another unit of measurement.

The system may then guide the user, via the software interface, to retract (1418) the endoscope from the trachea to a point prior to the trachea stenosis, and may capture (1420) a second image or set of images. The system may identify (1422) and overlay a visual boundary on the contour of the trachea prior to the stenosis, which may include identification by an object recognition process, partial user inputs to aid in identification, and manual user adjustments to the boundary, as has been previously described. The system may then determine (1424) the area of the airway prior to the stenosis in pixels or another unit of measurement.

The system may then compare the areas of the airway prior to, and immediately after the stenosis, and where a significant change (1426) exists, may notify (1428) the user that an untreated stenosis is present, or that a stenosis treatment procedure was not successful. A significant change (1426) in the airway may be determined by a configured threshold of change (e.g., a 40% reduction, a 30% reduction, etc.) from the pre-stenosis image to the post-stenosis image. Notification (1428) of the stenosis may include displaying images, image boundaries, current comparative images, historic comparative images, and various comparative information such as relative changes in the airway, as has been previously described. Where no significant change exists (1426), the system may notify (1430) the user that the stenosis is not present, or has been adequately repaired, and may include providing images, comparative images, historical comparative images, and information indicating the relative improvement in airway size post-procedure (e.g., pre-procedure stenosis may have caused a 75% reduction in airway area relative to the healthy trachea portion, while a post-procedure change may be a 10% reduction in airway area, or even an increase in airway area). As with prior examples, images and information may be provided to the image device (218), imaging server (220), or HIS (222), as has been previously described.

Figure 20B:
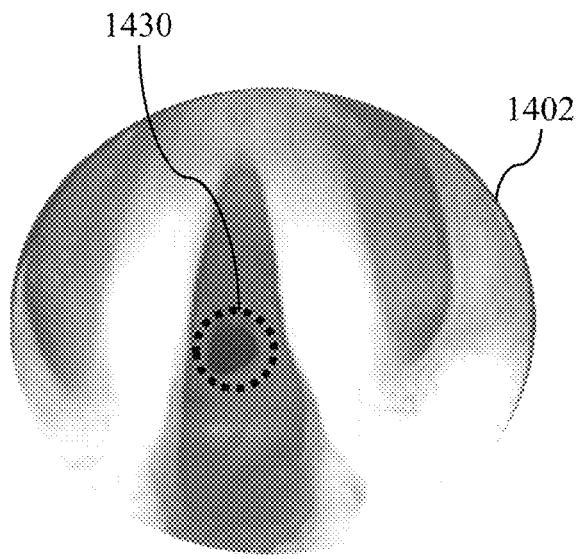
FIG. 20B is a screenshot of an exemplary interface for identifying tracheal stenosis.
Figure 20C:
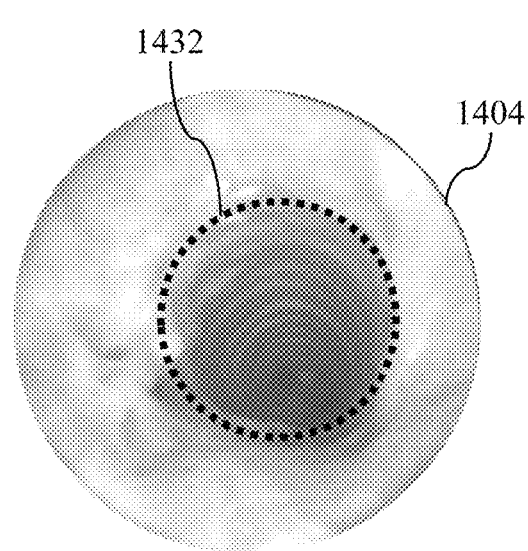
FIG. 20C is a screenshot of an exemplary interface for evaluating the results of a procedure to repair tracheal stenosis.

FIGS. 20B and 20C show screenshots of interfaces that may be used while identifying tracheal stenosis and/or evaluating the success of a stenosis repair procedure. FIG. 20B shows an image (1402) of the trachea just before the stenosis, with an overlaid boundary (1430) showing the identified (1422) and bounded airway through the stenosis. FIG. 20C shows an image (1404) of the trachea following a stenosis repair procedure, but is also illustrative of a healthy section of trachea that may be located just past the stenosis. A boundary (1432) is shown overlaid upon the cross sectional airway of the trachea. Each of the interfaces may be used to aid in identifying (1414, 1422) the respective anatomical boundary, including by receiving partial user inputs and manual adjustments, as has been previously described. As with prior examples, accelerometer data or other sensor data, as well as various range finding data, devices, or techniques may additionally be used with the steps of FIG. 20A to aid in the accurate positioning, and relative comparisons of bounded areas, as will be apparent to one of ordinary skill in the art in light of this disclosure.

Figure 21A:
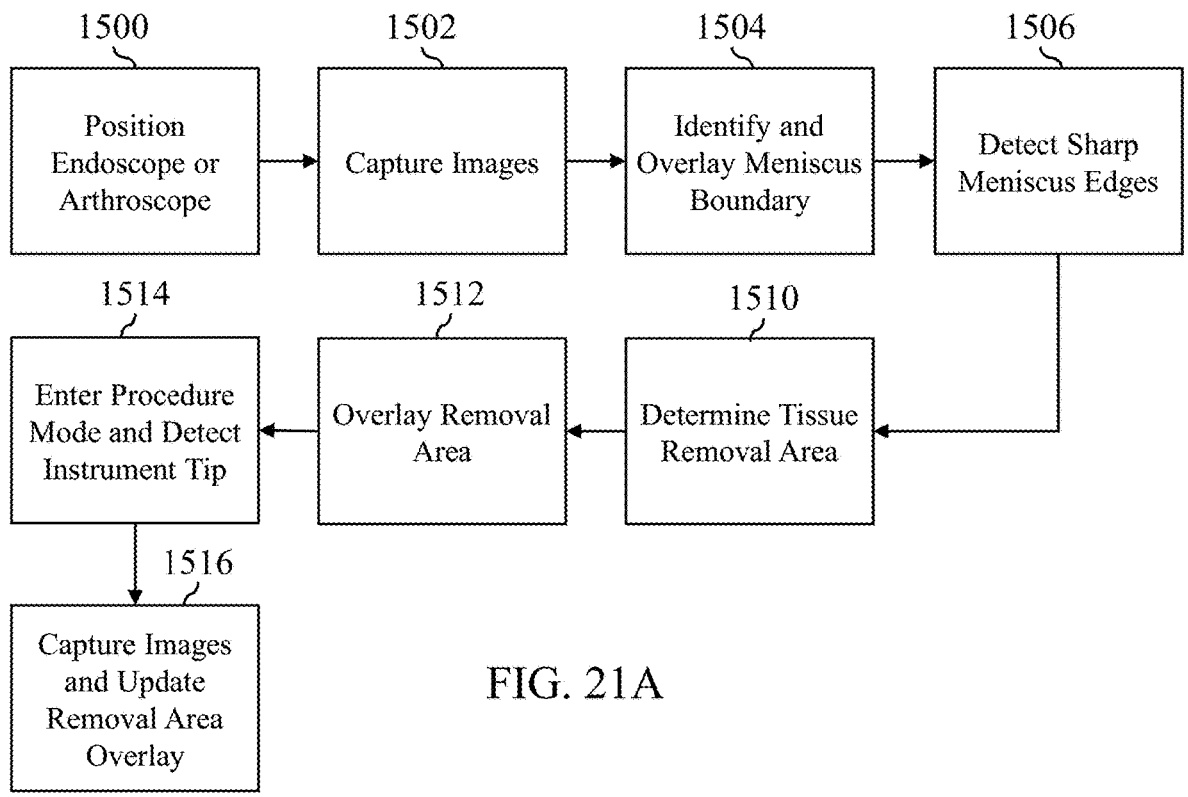
FIG. 21A is a flowchart of an exemplary set of steps that may be performed with the system of FIG. 3 to identify and aid in the removal of damaged portions of a meniscus.
Figure 21B:
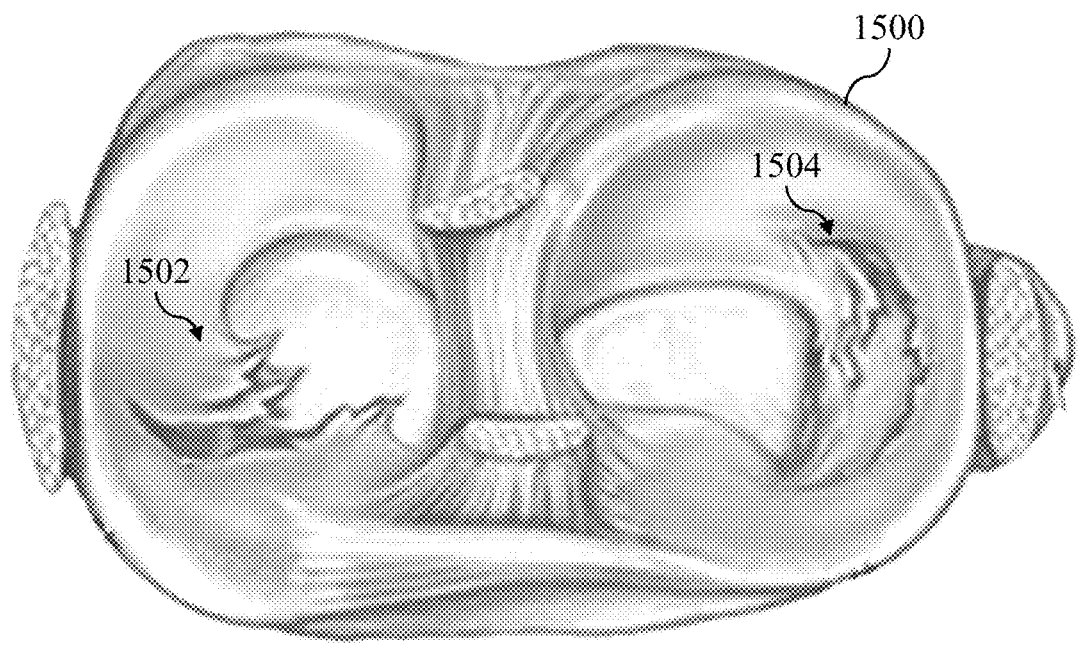
FIG. 21B is a simulated image of a damaged meniscus such as may be captured by an endoscope or arthroscope.

As another example of a feature or mode that the system can operate in, FIG. 21A shows a set of steps that may be performed to identify and aid in the removal of damaged portions of a meniscus, while FIG. 21B shows a diagram of a damaged meniscus (1500), which includes areas of damaged meniscus tissue (1502, 1504) on each side of the knee. Areas of the knee may be imaged using an endoscope or an arthroscope, for example, which may be positioned (1500) at a procedure site. An arthroscope is commonly used during minimally invasive knee procedures, and the steps of FIG. 21A may be advantageously implemented by a software application in communication with the pre-existing arthroscope. Once positioned (1500), images may be captured (1502) and the system may identify (1504) and overlay boundaries on portions of the meniscus, which may include using an object recognition process, receiving partial user input to aid in identifying the meniscus boundary, and receiving user modifications to an automatically applied boundary, as has been previously described.

The system may then analyze the meniscus boundary to detect (1506) any sharp or irregular edges, which may indicate the presence of damaged meniscus tissue. The system may then determine (1510) an area of the image that should be removed during a meniscus repair or removal procedure, and will overlay (1512) a visual indicator over the area to be removed. The visual indicator may be, for example, a boundary line, colored area, patterned area, or other visual indicator that may be overlaid upon the captured image. Determination (1510) of the tissue to be removed may be based upon received user input, or may be automatically determined by an object recognition process configured to identify and mark for removal any pixel of tissue that must be removed in order to leave a smooth edge to the remaining tissue (e.g., if the damaged tissue can be removed and leave a portion of the meniscus that does not include any sharp edges (1506)), or marking the entirety of the tissue of the meniscus for complete removal by marking each pixel identified as tissue.

With removal area overlaid (1512) upon the arthroscopic image, the software may be placed into a procedure mode (1514) in which an instrument tip being used during the procedure may be identified by the object recognition process (e.g., based upon a captured image, or an optical marker on the instrument tip, for example). As damaged tissue is removed, the system may continuously capture (1516) additional images of the procedure site, identify areas of the removal area where tissue has been removed, and overlay an updated removal area. In this manner, as the procedure continues, the overlaid removal area will gradually decrease. Determination of where tissue has been removed may be based upon identification (1504) of meniscus tissue within the image, or may be based upon the movement of the instrument tip, or both.

As an example, as a portion of tissue is removed a subsequent image may be processed by the object recognition process, and an identified portion of meniscus tissue may be compared to a prior identification of a portion of meniscus tissue, with the visual differences causing pixels of the overplayed removal area to disappear. Continuing the example, the position of the instrument tip over the course of a sequence of images may be used to focus the automated identification (1504) of meniscus tissue to those areas, disregarding other areas where the instrument tip has not been detected.

Figure 21C:
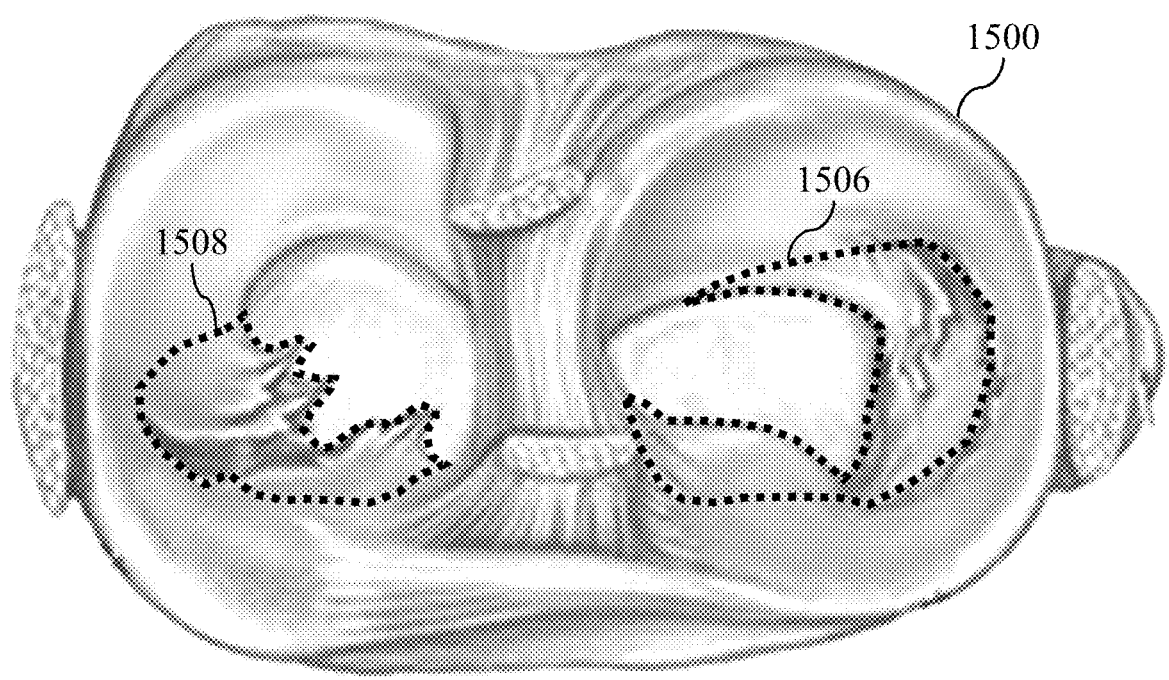
FIG. 21C is a screenshot of an exemplary interface for identifying damaged portions of a meniscus.
Figure 21D:
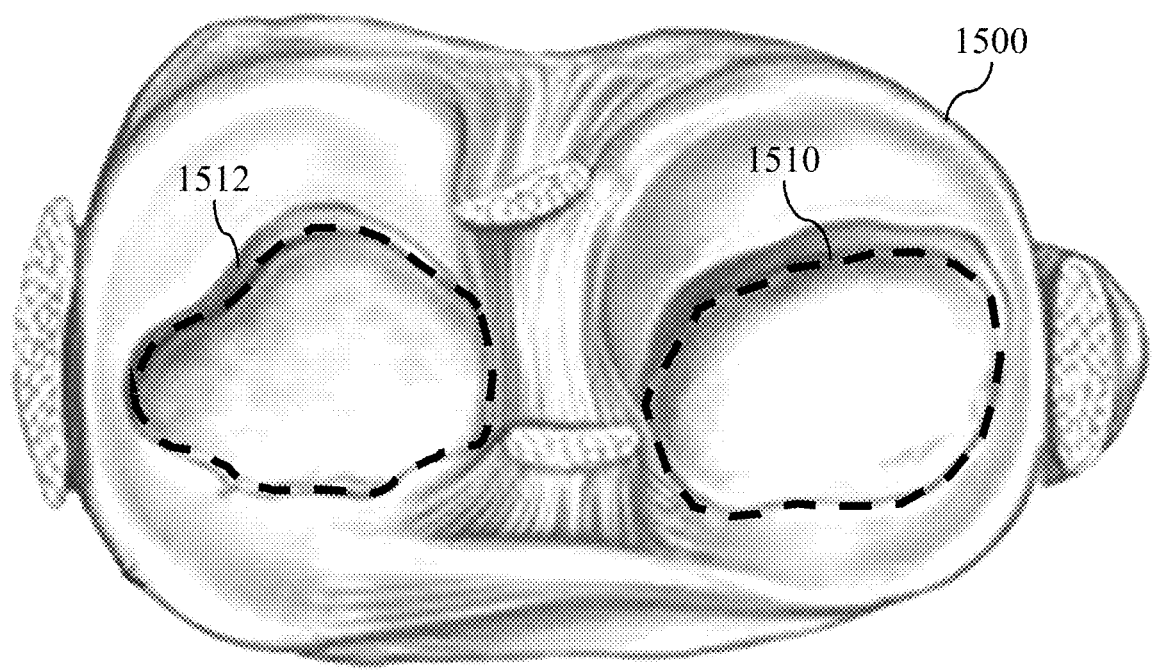
FIG. 21D is a screenshot of an exemplary interface for verifying complete removal of damaged portions of a meniscus.

FIGS. 21C and 21D each show interfaces that may be provided to aid in meniscus procedures. FIG. 21C shows an image of the meniscus, such as may be captured by an arthroscope, prior to removal of any tissue. A first portion of damaged tissue is present on the left of the image and a tissue removal boundary (1508) is overlaid upon the portions of tissue that include jagged edges, and that must be removed to result in a smooth edge. A second portion of damaged tissue is present on the right of the knee, and also includes a removal boundary (1506) indicating tissue that must be removed to leave a smooth edge. FIG. 21D shows the image of the knee after completion of the procedure, and all removal areas have been removed, leaving only a smooth boundary (1510, 1512) with no jagged or sharp edges that has been overlaid upon the remaining structure of the knee. The interface of FIG. 21C may be displayed to a user, and may receive partial user inputs or user modifications to the boundaries (1506, 1508), while the interface of FIG. 21D may be displayed after a procedure to verify completion of the procedure, and the lack of any remaining damaged portions of meniscus tissue.

Figure 22A:
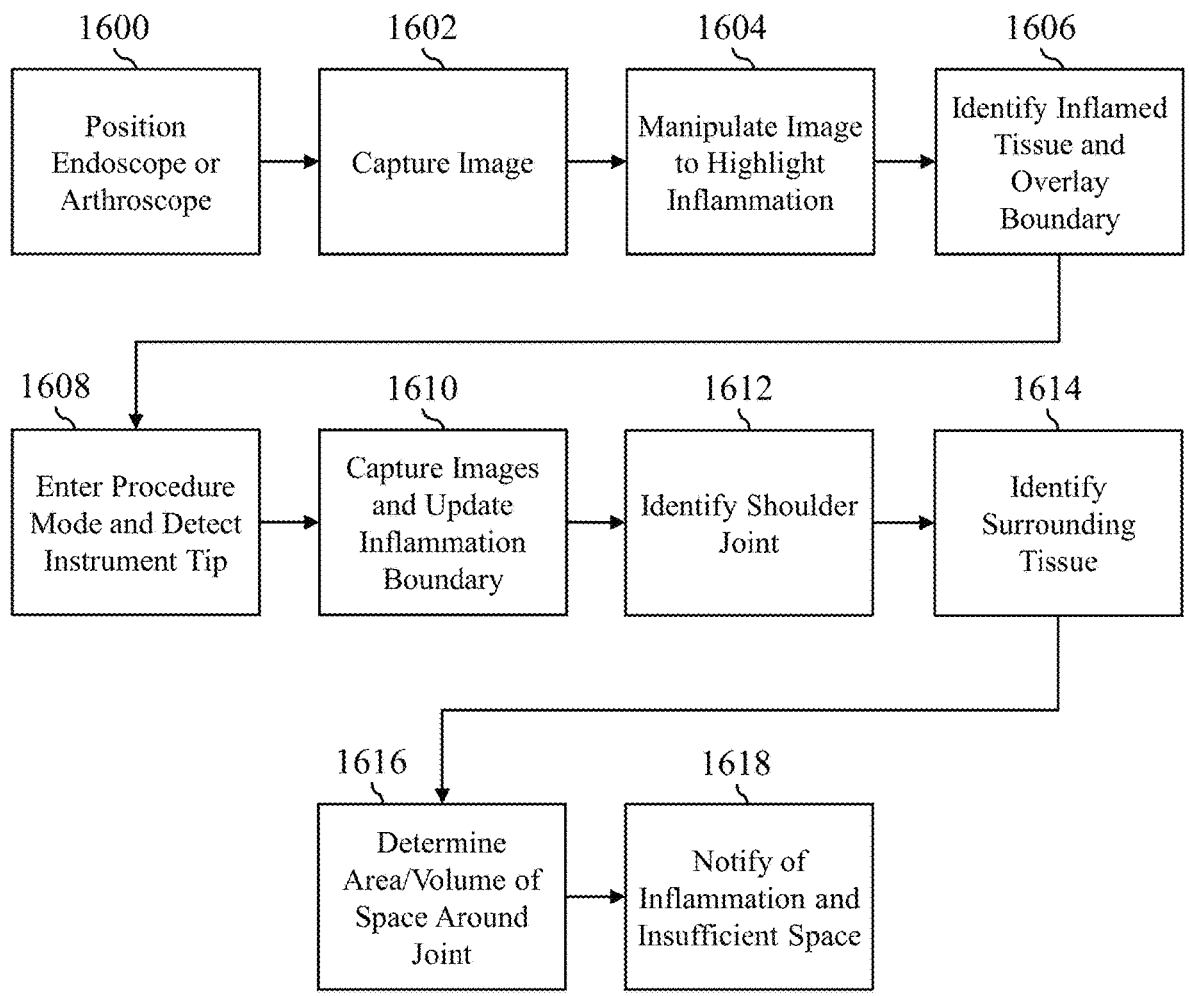
FIG. 22A is a flowchart of an exemplary set of steps that may be performed with the system of FIG. 3 to identify and aid in the removal of damaged portions of a shoulder joint.
Figure 22B:
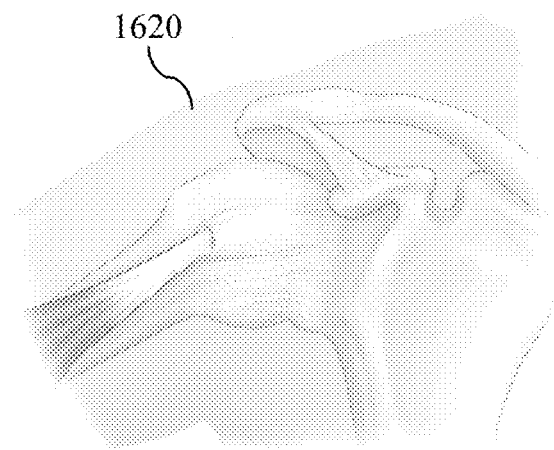
FIG. 22B is a simulated image of a healthy shoulder such as may be captured by an endoscope or arthroscope.
Figure 22C:
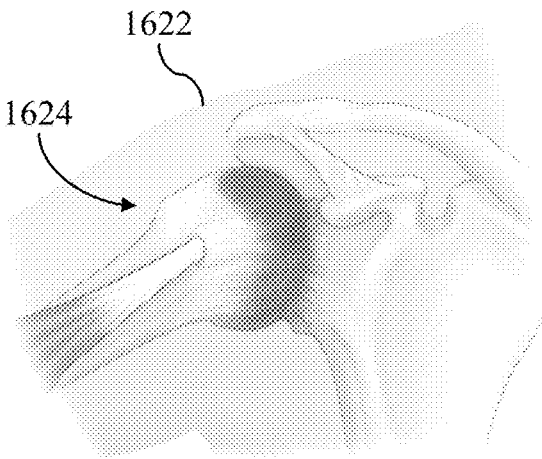
FIG. 22C is a simulated image of an injured shoulder such as may be captured by an endoscope or arthroscope.
Figure 22D:
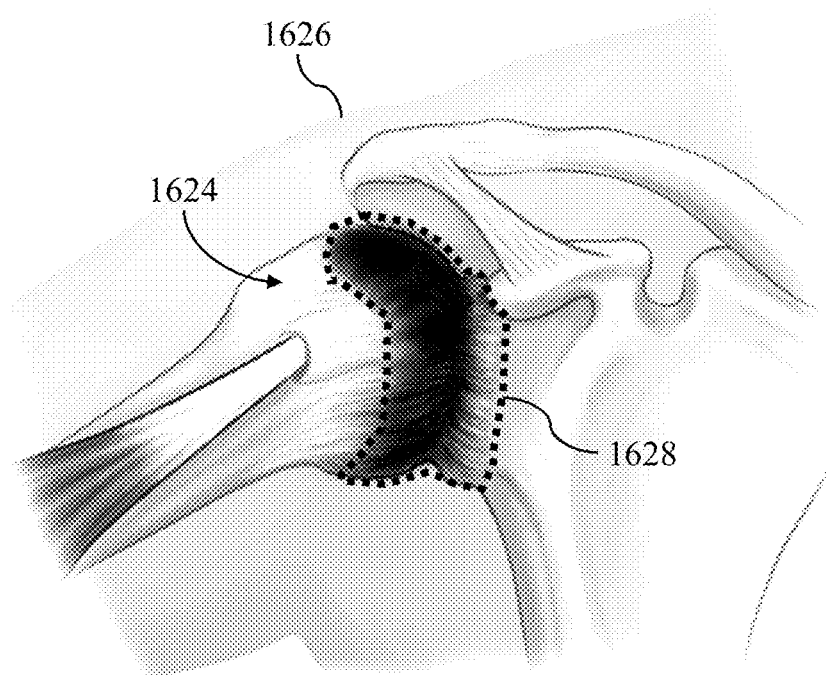
FIG. 22D is a screenshot of an exemplary interface for verifying complete removal of damaged portions of a shoulder joint.

As another example of a feature or mode that the system can operate in, FIG. 22A shows a set of steps that may be performed with the system to identify and aid in the removal of damaged portions of a shoulder joint. FIG. 22B is a diagram illustrating a healthy shoulder joint (1620), while FIG. 22C is a diagram illustrating an inflamed shoulder joint (1622). After positioning (1600) an endoscope or arthroscope at the procedure site, images may be captured (1602) of the procedure site. As images are captured, they may be manipulated (1604) to highlight and create a more distinct contrast between healthy tissue and inflamed or damaged tissue. Image manipulations may include color manipulations to increase the level of red colors and decrease the level of other colors in the image, creating a strong visual contrast that highlights the red and inflamed tissues. As an example, FIG. 22C shows a damaged area (1624) of the shoulder joint, while FIG. 22D shows a modified image (1626) where the inflamed tissue of the damaged area (1624) includes a strong visual contrast to surrounding tissues. The image of FIG. 22D also includes a boundary (1628) overlaid on portions of inflamed tissue.

The boundary (1628) may be overlaid after the system identifies (1606) inflamed tissue using an object recognition process, partial user inputs to aid in identifying the bounded anatomy, and manual user adjustments of an automatically applied boundary, as has been previously described. When the arthroscope is present at the site of the shoulder as part of a procedure, the system may then be placed into a procedure mode (1608) and a surgical instrument tip may be identified and tracked for the remainder of the procedure (e.g., by use of an image recognition process, the presence of an optical marker on the instrument, or both). In procedure mode, captured images (1610) may be continuously analyzed to identify portions of inflamed tissue that have been repaired or removed (e.g., similar to the steps described in the context of FIG. 21A). As one example, inflamed tissue may be highlighted by a boundary (1628), color overlay, or pattern overlay, and as inflamed tissue is removed and healthy tissue is detected, the visual overlay may shrink or otherwise update to reflect the presence of healthy tissue.

While tracking removal of inflamed tissue, the system may also identify (1612) the shoulder joint and identify (1614) the tissues surrounding the shoulder joint, which may include using an object recognition process, partial user inputs to aid in object recognition, or manual user updates to an applied boundary, as has been previously described. The system may then determine (1616) the area, or volume of space between the shoulder joint and the surrounding tissue, and provide a notification (1618) to a user when the determined area or volume is below a configured threshold, or when inflamed tissue is still detected in the image throughout the procedure. Determination of a two dimensional area of space may be based upon pixel measurements of bounded areas within the image, while determinations of volume may be performed as described in the context of FIG. 14A. In this manner, the system may provide a surgeon or other user an updating reference throughout a procedure, which may include visual indications of tissue that should be evaluated for removal, and visual indications and descriptions of whether there is sufficient space between the remaining tissues and the surrounding tissues.

Figure 23:
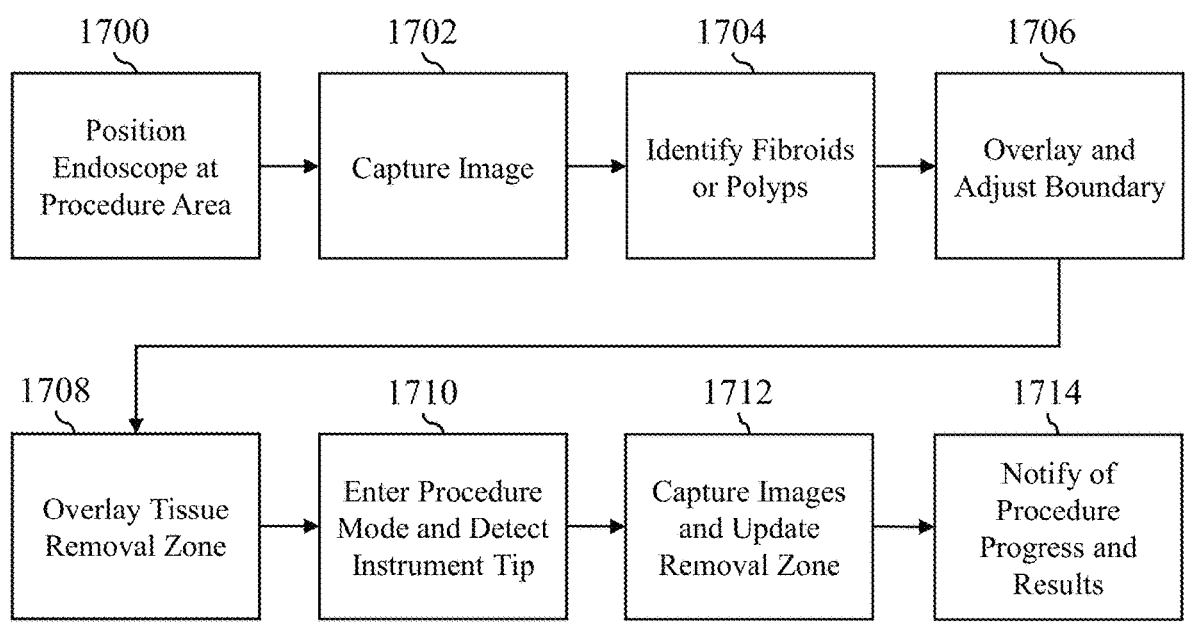
FIG. 23 is a flowchart of an exemplary set of steps that may be performed with the system of FIG. 3 to identify fibroids and polyps during an obstetrics and gynecology procedure.

As another example of a feature or mode that the system can operate in, FIG. 23 shows a set of steps that may be performed to identify fibroids and polyps during an obstetrics and gynecology procedure. An endoscope may be positioned (1700) at the procedure site, and images may be captured (1702). As images are captured, the system may identify (1704) fibroids and/or polyps present in the procedure area, and may overlay (1706) a visual boundary on the identified portions of the image. This may include using an object recognition process, partial user inputs to aid in identifying the particular anatomy, and manual user inputs to adjust an automatically applied boundary. Identification (1704) of the fibroids and/or polyps may be based upon their relative position to other anatomy, based upon a distinct color or surface texture as compared to surrounding anatomy, and based upon the size and shape of the tissue. A tissue removal zone may also be determined and overlaid (1708) upon the image, which may include a visual boundary, color, or pattern over the identified (1704) area.

The system may then be placed into a procedure mode (1710) in which a surgical instrument tip is identified and tracked throughout the procedure area, which may include an object recognition process and/or optical markers positioned on the instrument tip. While in procedure mode, the system may continuously capture images (1712), identify changes in the presence of polyp and fibroid tissue within the image, and update the removal zone to reflect the removal of the abnormal tissue. As with prior examples, this may be based upon object recognition and comparison between images, or based upon the tracked location of the instrument tip, or both. The system may then notify (1714) a user of the procedure progress and results, which may include ongoing updates to the removal area as tissue is removed, or automatic alerts when no more polyp or fibroid tissue is identifiable (1704) within the captured images.

Figure 24:
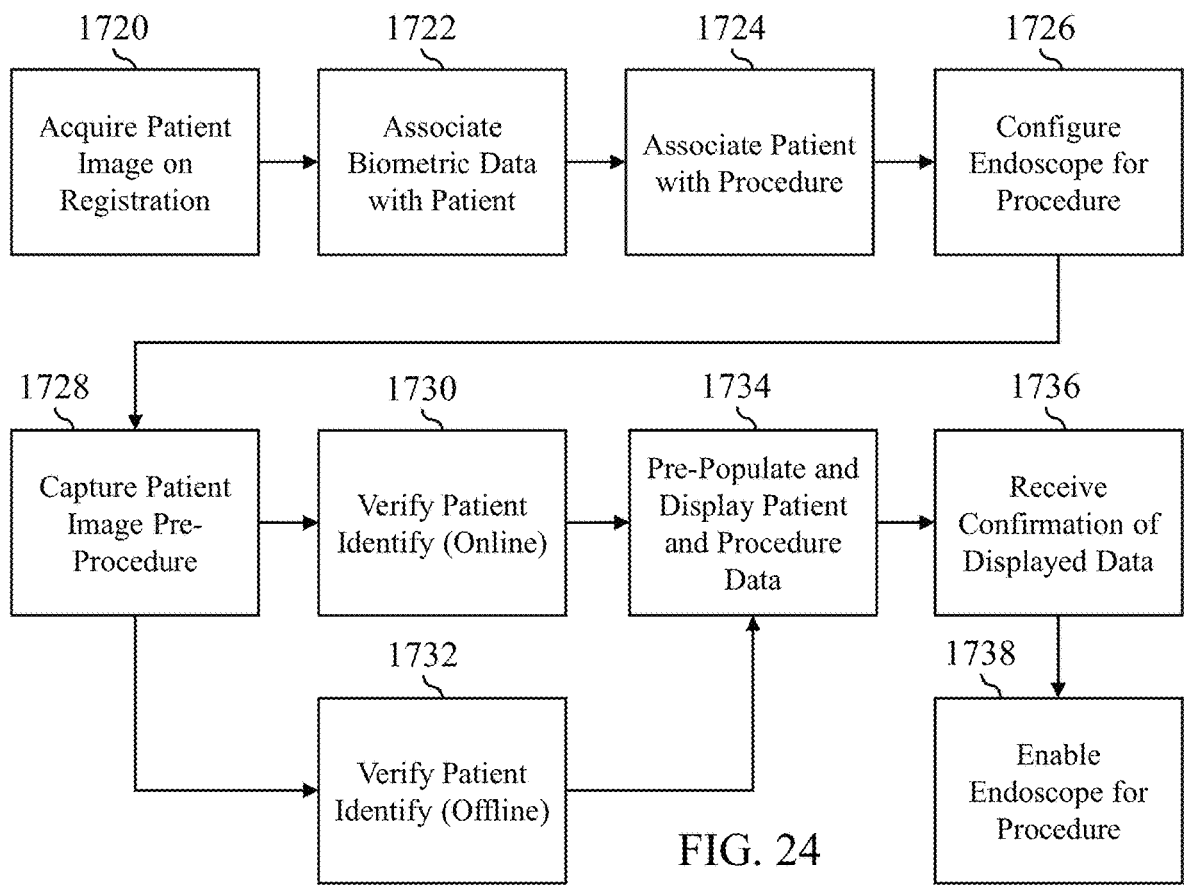
FIG. 24 is a flowchart of an exemplary set of steps that may be performed with the system of FIG. 3 to pre-configure the system for a procedure based on a verification of patient identity.

FIG. 24 is a flowchart of an exemplary set of steps that may be performed with a system such as that of FIG. 3 to pre-configure the system for a procedure based on a verification of patient identity. When a patient is first associated with the system, such as by registration of the patient's information with the HIS (222), an image of the patient is acquired (1720) and a set of biometric data is produced and associated (1722) with the patient registration on the HIS (222), along with other initial patient information such as name, age, contact information, physical characteristics, medical conditions, and other information. The acquired biometric data may be, for example, a facial image, an image of the patient's eye, an image of the patient's palm, an image of one or more fingerprints of the patient, or a combination thereof. Subsequently, when the patient schedules a procedure or other service, the system may associate (1724) the scheduled procedure with the patient's information on the HIS (222).

Prior to the procedure, the imaging device (218) or endoscope control (216) may be configured (1726) for the patient and/or procedure by communicating with the HIS (222) and receiving information related to the patient and the procedure, including the stored biometric data. Information may be received via a wired or wireless connection to the HIS (222) or another device or system, and may be received in in near real-time in response to a request from the imaging device (218) at the time of the procedure, or may be pushed to the imaging device (218) while it is not in use (e.g., overnight, when the imaging device (218) is docked to another device for charging or data exchange, or based on a configured schedule) and then stored on the imaging device (218) for future performance of the procedure.

Private information of the patient may be stored on the imaging device (218) in an encrypted/encoded format so that it is not readily accessible without an encryption key or code. This encryption key or code may be provided by the patient themselves at the time of the procedure in order to enable access to their information, or may be automatically provided based upon a subsequent biometric data captured from the patient that can be verified as a match with the biometric data stored on the imaging device (218). In this manner, the imaging device (218) may be used for various procedures in an "offline" mode where needed patient data is stored on the device in an encrypted format, and where the encryption key is only provided/accessible based upon a successful biometric verification of the corresponding patient.

At the time of the procedure, the procedure staff may use the endoscope (212) to capture current biometric imaging data of the patient (e.g., face, eye, fingerprint, etc.) as a first step of the procedure. The software interface of the imaging device (218) may prompt the user to capture the appropriate biometric data so that the patient identify can be verified before proceeding to subsequent screens or interfaces used during the procedure. The system may then use the current biometric data to verify (1730) the patient identity in an online mode, verify (1732) the patient identify in an offline mode, or both. Online verification (1730) may be performed when connectivity to the imaging server (220) and/or HIS (222) is available, and may include transmitting the current biometric data to a remote server where it can be analyzed and compared to stored biometric data of the patient (e.g., such as that acquired (1720) at registration). Offline verification (1732) may be performed entirely by the imaging device (218) based on previously received and stored biometric data for the patient. Biometric verification may be performed in varying ways, including with the use of facial recognition techniques, image recognition and comparison techniques, and other image analyses, including the use of artificial intelligence techniques in some implementations.

In some implementations, the biometric verification may be based in part upon, or only upon, patient information and currently captured biometric images without the use of previously captured biometric data for a comparison. As an example, a current biometric image of the patient could be analyzed to determine or estimate an age, gender, ethnicity, hair color, eye color, and other characteristics of the patient that may be compared to corresponding information provided by the patient at the time of registration.

Where one or both forms of verification are successful, the imaging device (218) may receive, or may gain access to locally stored, information of the patient. Based on a successful online verification (1730), the HIS (222) may provide patient information, procedure information, and other information to the imaging device (218) or other procedure device. The same may be locally accessible in the event of a successful offline verification (1732). As an example, the output of a successful offline verification process may include a flag or Boolean value indicating success, as well as an encryption key usable to access the corresponding patient information stored on the imaging device (218) in an encrypted format, while an unsuccessful verification process may only output a flag or Boolean value indicating failure, such that the encrypted data also remains inaccessible. Where a patient's identity cannot be successfully verified, it may indicate an error in the patient or procedure data stored by the HIS (222), an error of the medical staff (e.g., wrong patient prepared for procedure, wrong procedure device selected for use in the procedure), or other anomalies that must be manually reviewed and/or addressed before the imaging device (218) is enabled for the procedure.

The system may then pre-populate and display (1734) the verified patient information and procedure information via the imaging device (218). Displayed information may be manually reviewed by the medical staff and/or the patient, and any missing data or erroneous data may be provided or corrected manually if necessary. The system itself may also perform some automated review of this data, such as verifying that the imaging device (218) and endoscope (212) are the proper devices for the current procedure, and are properly configured for performing the current procedure.

After receiving confirmation (1736) of the displayed (1734) data, the system may be enabled (1738) for performance of the procedure, which may include enabling the imaging device (218), control (216), endoscope (212), or other devices and providing the appropriate interfaces and functionalities as have been described above.

Figure 25A:
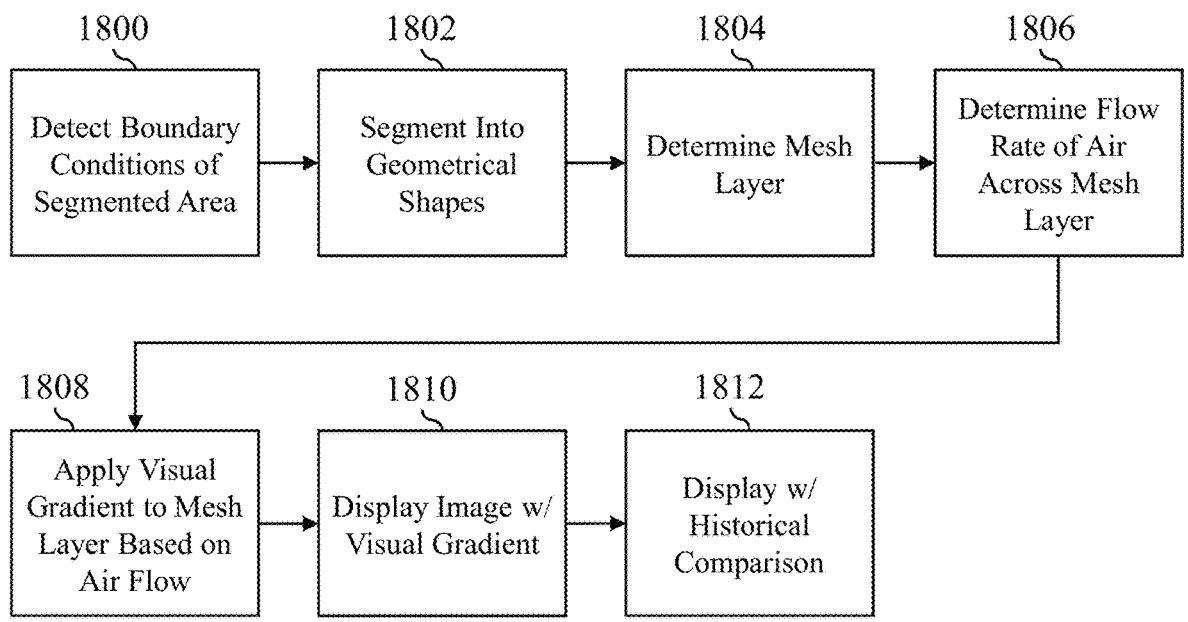
FIG. 25A is a flowchart of an exemplary set of steps that may be performed with the system of FIG. 3 to provide a measurement of airflow through the nasal cavity.

As another example of a feature or mode that the system can operate in, FIG. 25A is a flowchart of an exemplary set of steps that may be performed to provide a measurement of airflow through the nasal cavity. As with prior disclosed features or modes, the steps of FIG. 25A may be performed as a singular or discrete process, or may be performed in parallel with, or in sequence with, other procedures based on the same or subsequently captured images (e.g., a single image or the same set of images of the nasal canal may be analyzed according to the steps of FIGS. 4, 5, 7A, 8A, 25A, and so on after capture). After receiving captured images of the interior of the patient nasal canal (e.g., captured by the endoscope (212) or another device) and segmenting the captured images (e.g., as has been described above in the context of FIG. 4, FIG. 14A, and others), the system (e.g., the imagine device (218), the imaging server (220), or a combination of devices) may analyze the image to detect (1800) the boundary conditions of a segment, and then segment (1802) the bounded area into a set of geometrical shapes (e.g., triangles, squares, other shapes of three sides or more).

The vertices, edges, or other known points of the geometric shapes provide known points that can interpreted (1804) as a multi-point mesh layer overlaid upon the image, which the system can interpret to give an indication of anatomical structures such as the position, depth, size, and shape of anatomical structures present within the image. The system may then determine (1806) the flow rate of air across the mesh layer using one or several methods. As an example, a computational fluid dynamics ("CFD") formula or simulation may be used to predict the flow of air across the entire mesh layer (e.g., for individual pixels, groups of pixels, geometric shapes, or groups of geometric shapes). As another example, airflow across the mesh layer may be estimated based upon the relative distance of any given point or points within the mesh layer to the edges of the segmented area. This method provides a simple yet effective estimate, as magnitude of airflow strongly correlates to a lack of obstruction from the tissues and other anatomy present at the border of the segment.

The system may then apply a visual gradient to the image based on the determined (1806) flow rate of the mesh layer and display (1810) the image with the overlaid visual gradient via the imaging device (218) or another device. The displayed (1810) image provides an effective illustration of airflow based on a single or small number of captured images, and may be readily interpreted and used by medical staff to counsel a patient and/or provide further procedures. The system may also display (1812) one or more historical images and airflow analyses that have been performed for the patient in the same or a separate interface as the current image, which may be useful to illustrate changes in airflow over time (e.g., between examinations, pre- and post-procedure, etc.).

Figure 25B:
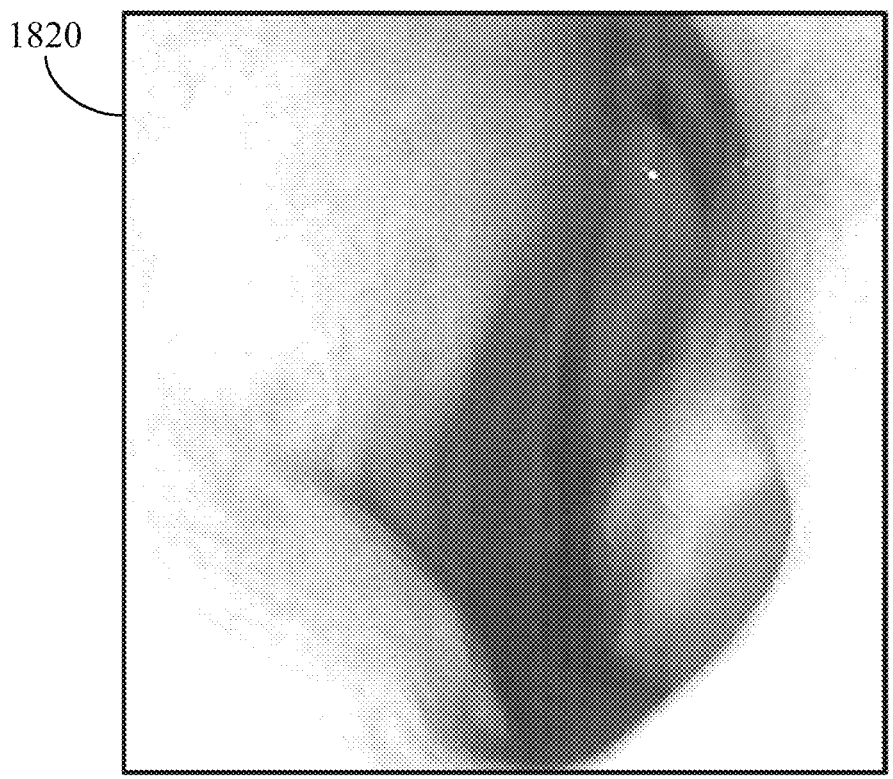
FIG. 25B is a screenshot of an exemplary interface for determining a measurement of airflow at a first step.
Figure 25C:
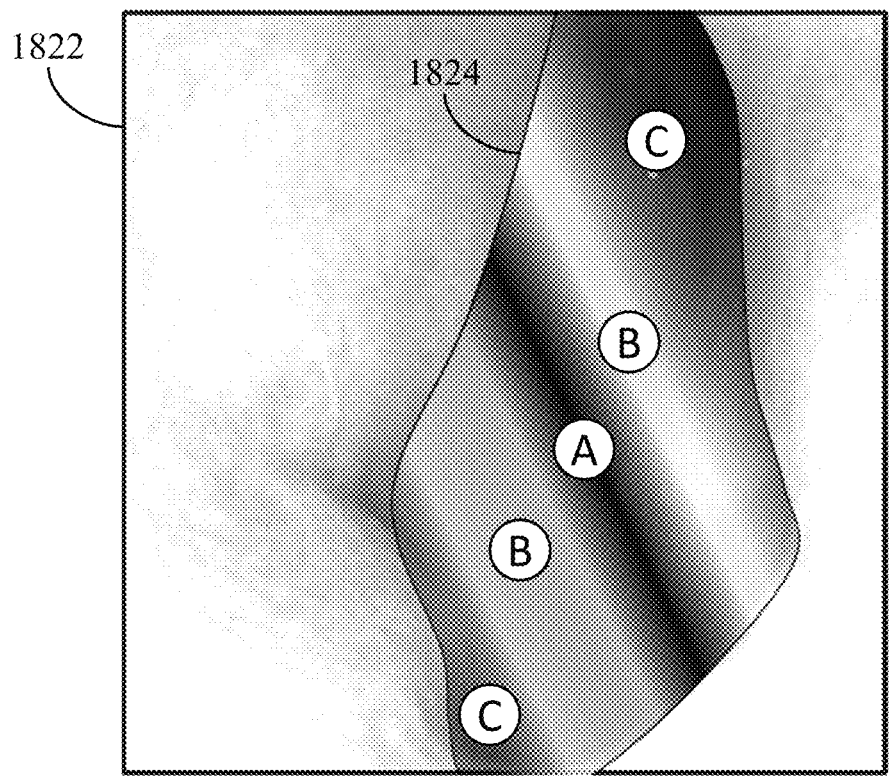
FIG. 25C is a screenshot of the interface of FIG. 25B at a second step.
Figure 25D:
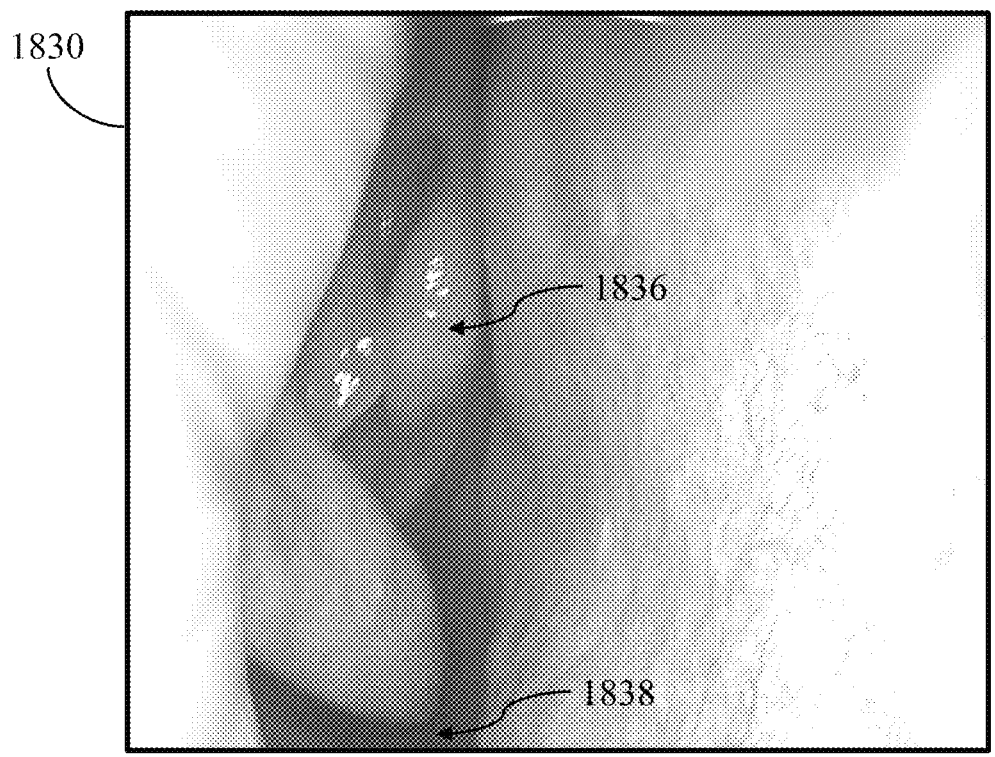
FIG. 25D is a screenshot of another exemplary interface for determining a measurement of airflow at a first step.
Figure 25E:
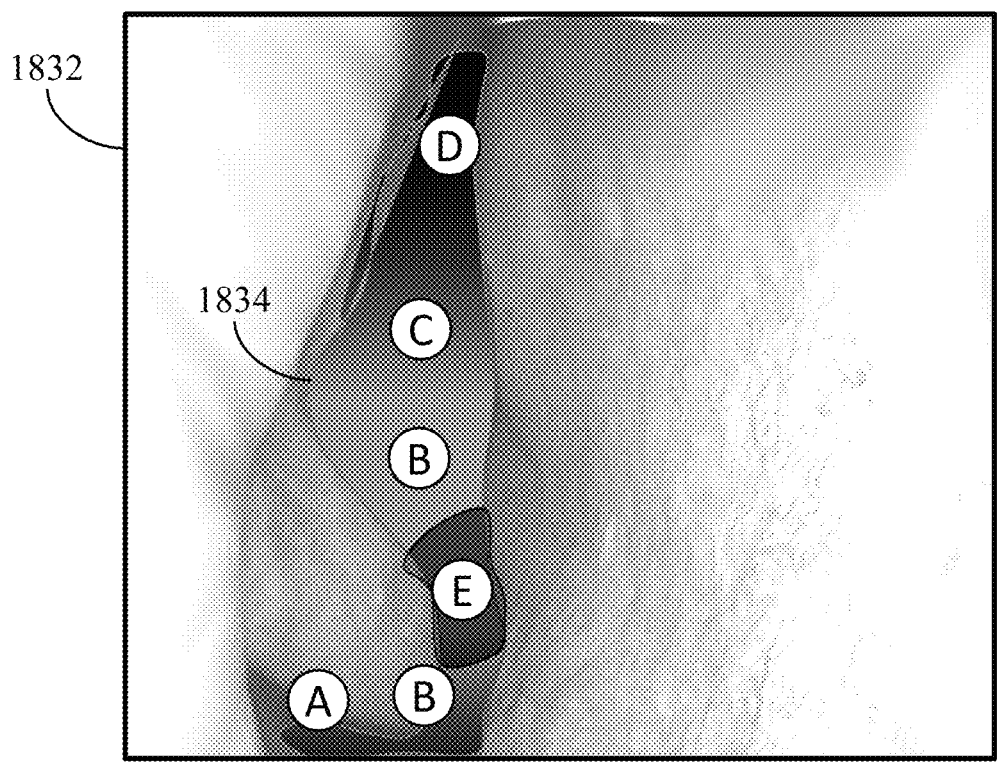
FIG. 25E is a screenshot of the interface of FIG. 25D at a second step.

FIGS. 25B-25E provide examples of interfaces that may be displayed (1810) based on an airflow analysis such as that described above. FIG. 25B shows an image (1820) of a patient nasal canal captured by an endoscope such as the endoscope (212). FIG. 25C shows an image (1822) after application (1808) of a visual gradient (1824) to the image (1820). The image (1822) is similar to what may be produced by a determination (1806) of airflow based on relative distance from segment borders, resulting in a centrally located stripe of high airflow marked as "A". Extending outwards from the A stripe, the airflow gradient blends into two surrounding stripes of moderate airflow marked as "B", which exhibit relatively lower airflow due to their increasing proximity to the outer boundaries of the segment. Extending outward from each B stripe and further towards the distal edges of the nasal canal are two stripes of low airflow marked as "C", which exhibit further reduced airflow due to the increasing proximity to portions of the FIG. 25D shows an image (1830) of a patient nasal canal captured by an endoscope such as the endoscope (212). FIG. 25E shows an image (1832) after application (1808) of a visual gradient (1834) to the image (1830). The image (1832) is similar to what may be produced by a termination (1806) of airflow based on a CFD simulation or other airflow simulation or algorithm. In contrast to the gradient (1824) of FIG. 25C, the gradient (1834) has an airflow marked as "B" (e.g., moderate airflow) blending into "C" (e.g., low airflow) at its widest point, as the algorithm accounts for the structures of anatomy (1836), visible in FIG. 25D, at depths other than the current segment (e.g., detectable by interpretation of the mesh layer). At the topmost part of the image (1832) an area marked "D" exhibits very low airflow, due to both being a narrow area and having additional anatomy present at further depths. Moving towards the bottom of the image (1832) from the central B area, an area marked "E" exhibits extremely low airflow, due again to being within a narrow area of the nasal canal and underlying anatomical structures at further depths. Moving further towards the bottom of the image (1832), the bounded segment includes a B area (e.g., moderate airflow) and an "A" area (e.g., high airflow). Each of the A and B area exhibit relatively high airflow despite being at narrow areas of the bounded segment, due primarily to the lack of anatomical structures at proximate depths (1838), as visible in FIG. 25D.

As further example of the disclosed technology, while many of the examples provided here in are described as image analysis, image processing, image modification, and object identification within images based on images captured by an endoscope such as the endoscope (212) of FIG. 3, it should be understood that the same features and concepts may be applied to images having various types and various sources. As an example, some or all of the disclosed steps illustrated in the figures (e.g., those of FIG. 4 and others) may be performed based on images and image data captured by an MRI scan (e.g., a single image slice, or across multiple), CT scan (e.g., a single image slice, or across multiple), endoscopic camera, other optical imaging, and may also be performed based on simulated images of patient anatomy such as may be provided by a 3D patient model or other digital rendering.

The ability to analyze endoscopic images and 3D image data using the same or similar techniques and processed as disclosed herein is advantageous for several reasons. As one example, performing steps such as those illustrated in FIG. 4 to determine obstruction based on an endoscopic image of the nasal valve, and then doing the same for a 3D patient model of the nasal valve that has been modified to approximate the results of a particular procedure for that patient, will provide a credible comparison since the same analysis or tool is being used to provide each different data set.

As further example, the image manipulation, analysis, and object detection features described herein may be used to correlate or register endoscopic images of a particular patient anatomy with pre-procedure 3D image data of the same anatomy. As an example, where a particular patient undergoes a CT scan prior to a nasal valve procedure, the 3D image data of the CT scan may be available for a surgeon to view while preparing for a nasal valve procedure, but may not have value as a navigation tool during the procedure without significant additional equipment and configuration (e.g., typically, an image guided surgery and navigation suite, which may require magnetic field generators, specialized patient chairs or beds, embedded magnetic sensors, and other costly equipment).

However, using the system of FIG. 3, endoscopic images captured by the endoscope (212) may be segmented (e.g., such as illustrated in FIG. 14A-14D) to provide an indication of depth, discrete anatomical structures, or other boundaries to the two dimensional image. Once analyzed and segmented, the augmented two-dimensional image may be more readily correlated to portions of the 3D image data, as the image matching algorithm may compare the two-dimensional image to a two-dimensional image slice from the 3D image data, or may compare the augmented two-dimensional image to three dimensional portions of the 3D image data, or both, in order to match the endoscopic image to a portion of the 3D image or vice versa.

This may be useful to enhance the display or use of an endoscopic image by using correlated 3D image data as an overlay or side-by-side-display, or to refine other aspects of the endoscopic image such as the automated segmentation performed on the endoscopic image (e.g., a first-pass automated segmentation may be performed so that the endoscopic image may be correlated to the 3D image data, and then the first-pass segmentation might be updated based on the 3D image data to improve accuracy of the segmentation). In the opposite scenario, this may be useful to enhance the display or use of 3D image data by adding the segmented endoscope image as an overlay or side-by-side display, or to refine aspects of the 3D image data (e.g., by filling in portions of the 3D image data that are empty, low resolution, or contain other errors or visual artifacts).

Figure 26A:
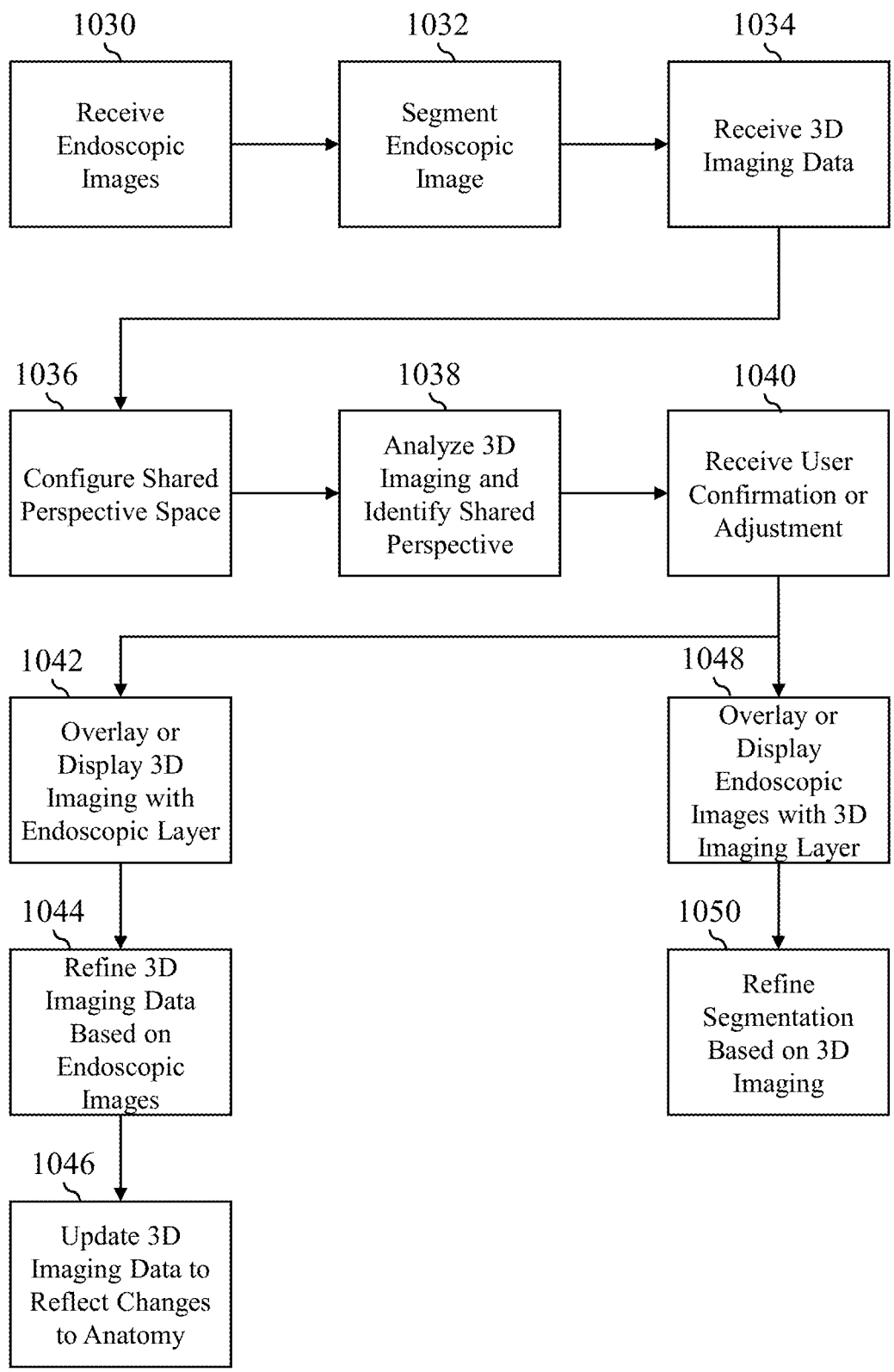
FIG. 26A is a flowchart of an exemplary set of steps that may be performed with the system of FIG. 3 to correlate segmented endoscopic images with corresponding portions of 3D image data.

As further example of the above, FIG. 26A shows an exemplary set of steps that may be performed with the system of FIG. 3 to correlate segmented endoscopic images with corresponding portions of 3D image data. Endoscopic images may be received (1030) and segmented (1032) as has been previously described (e.g., any of the prior techniques for detecting boundary or border areas of the image and associating those boundaries with depth, specific anatomy, or otherwise). The system may also receive (1034) 3D imaging data, such as pre-procedure 3D imaging produced by a CT or MRI scan.

To assist with the correlation and narrow down the search space of the 3D image data, the system may be configured (1036) with one or more parameters that define a shared perspective space. Parameters defining the shared perspective might be based on a particular procedure (e.g., a procedure on the left nasal canal can exclude portions of the 3D image data not visible from the let nasal canal), based on a particular endoscope (e.g., due to limitations on insertion and angling of the endoscope, such as where the endoscope (212) might be positioned at the end of a 2-3 inch long rigid shaft), or based on feedback from position and orientation sensors within the endoscope (212), for example. Defining the shared perspective space might also include configuring the 3D image data slicing and the depth-segmentation of the endoscopic images to have a shared "thickness" (e.g., the simulated layers of the segmented endoscopic image may be configured to have the same depth as the image slices of the 3D image data).

The system may then analyze (1038) and search the 3D imaging data for a portion that matches the segmented endoscope image, which may be referred to as the "shared perspective," or the position and orientation in the 3D imaging data at which an observer would see the same anatomy as depicted in the endoscope image. Searching of the 3D imaging data may be narrowed to a potential shared perspective space based as has been described, and may be searched and compared based on two dimensional image data (e.g., comparing an endoscope image to an image slice of the 3D image data), 3D image data (e.g., comparing an endoscope image with segmentation data to a 3D portion of 3D image data), or both. When a match is found, the system may display (e.g., via the imaging device (218)) the match as a partial translucent overlay, a side by side comparison, or another visual display so that a user may confirm or adjust the match, if needed.

Once any confirmation or adjustment is received (1040), the system may finalize the match, which may include producing additional interfaces showing the matched views as overlays or side-by-side comparisons, and for real-time endoscopic images, may also begin to provide ongoing correlation and display as the perspective of the endoscope changes for subsequent images. Once an initial match is made as described above, subsequent image matching searches may be further confined to a narrower shared perspective space based upon the determined position of a prior match (e.g., each immediately subsequent image will have a very small potential search space, due to limitations on the speed of movement and rotation of the endoscope between images).

Other steps performed by the system after a successful match may include displaying an overlay (1042) or side by side of an endoscopic image layer onto 3D imaging data. The system may also refine (1044) the 3D imaging data based on the corresponding endoscope image and segmentation in order to replace portions of the 3D imaging data that are empty, low resolution, or are obscured by visual artifacts. The system may also update (1046) the 3D image data based on the corresponding endoscope image and segmentation so that the 3D image data reflects recent changes to the anatomy as a result of a procedure or other condition. As an example, where tissue has been removed, modified, or supported by a surgical implant subsequent to creation of the 3D image data, those changes will be visually reflected in the endoscope images and segmentation data, but will not be reflected in the 3D image data. Since the endoscopic image and segmentation data can be correlated to the 3D image data, those subsequent changes to the tissue can be back-filled into the 3D image data so that it represents the patient's current anatomy without requiring additional scanning of the patient.

The system may also overlay (1048) or provide a side-by-side display of the endoscopic images with a 3D image data layer. This may be useful where, during a procedure with the system of FIG. 3, the surgeon may view live endoscopic images of the patient anatomy via the imaging device (218), and may also view corresponding portions of 3D image data as an overlay or side-by-side comparison. As further example, the surgeon may interact with the imaging device (218) to shift the perspective of the 3D image data to see a portion of anatomy that is not present or is visually obstructed in the endoscope image, and when the interaction ends the 3D image data view may snap back to a position that matches the endoscopic view (e.g., this could allow the surgeon to advance further into the nasal canal or rotate to various orientations in order to gain information about their surroundings without moving the endoscope itself).

The system may also refine (1050) the segmentation data associated with the endoscope images based on the 3D imaging data, once a match is achieved. For example, where the endoscope image segmentation is inaccurate or incomplete, such as where a border may not be accurately represented, or the depth of a particular portion of anatomy is not accurately represented, the matching 3D imaging data may be used to overwrite or refactor the segmentation in order to provide a more accurate result.

Figure 26B:
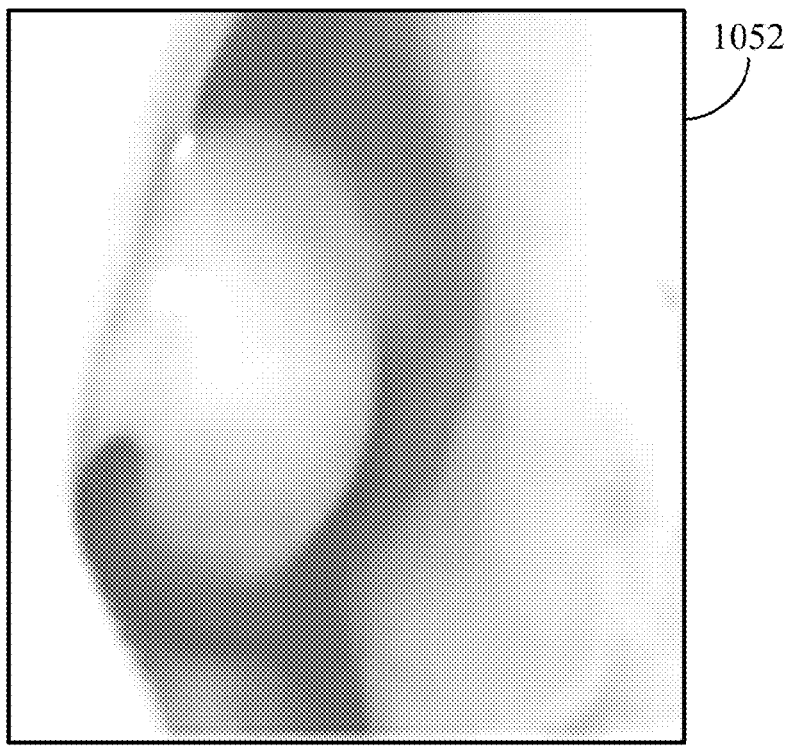
FIG. 26B is a screenshot of an exemplary interface for displaying segmentation of an endoscope image at a first step.
Figure 26C:
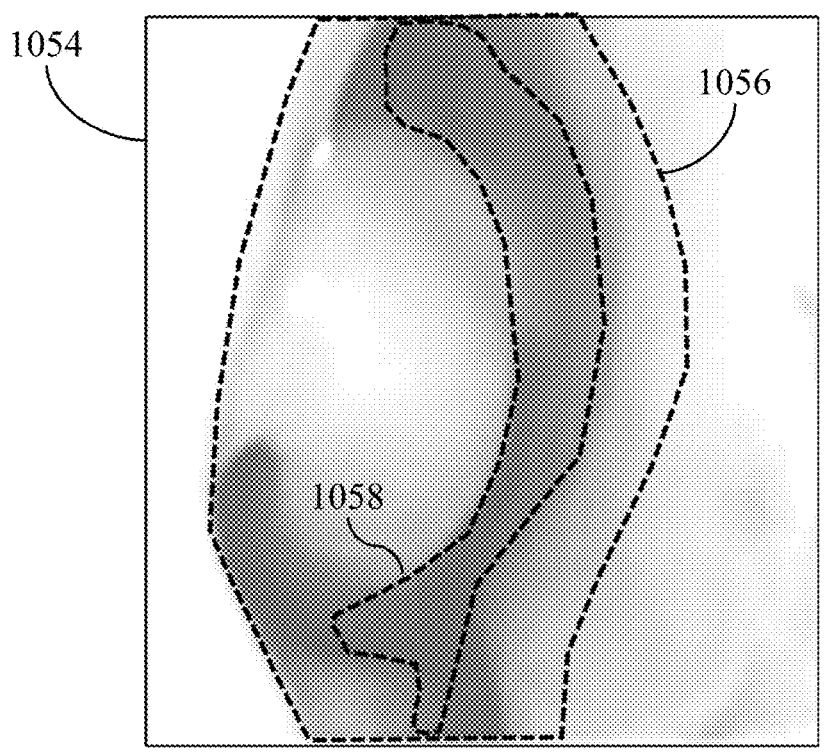
FIG. 26C is a screenshot of the interface of 26B at a second step.
Figure 26D:
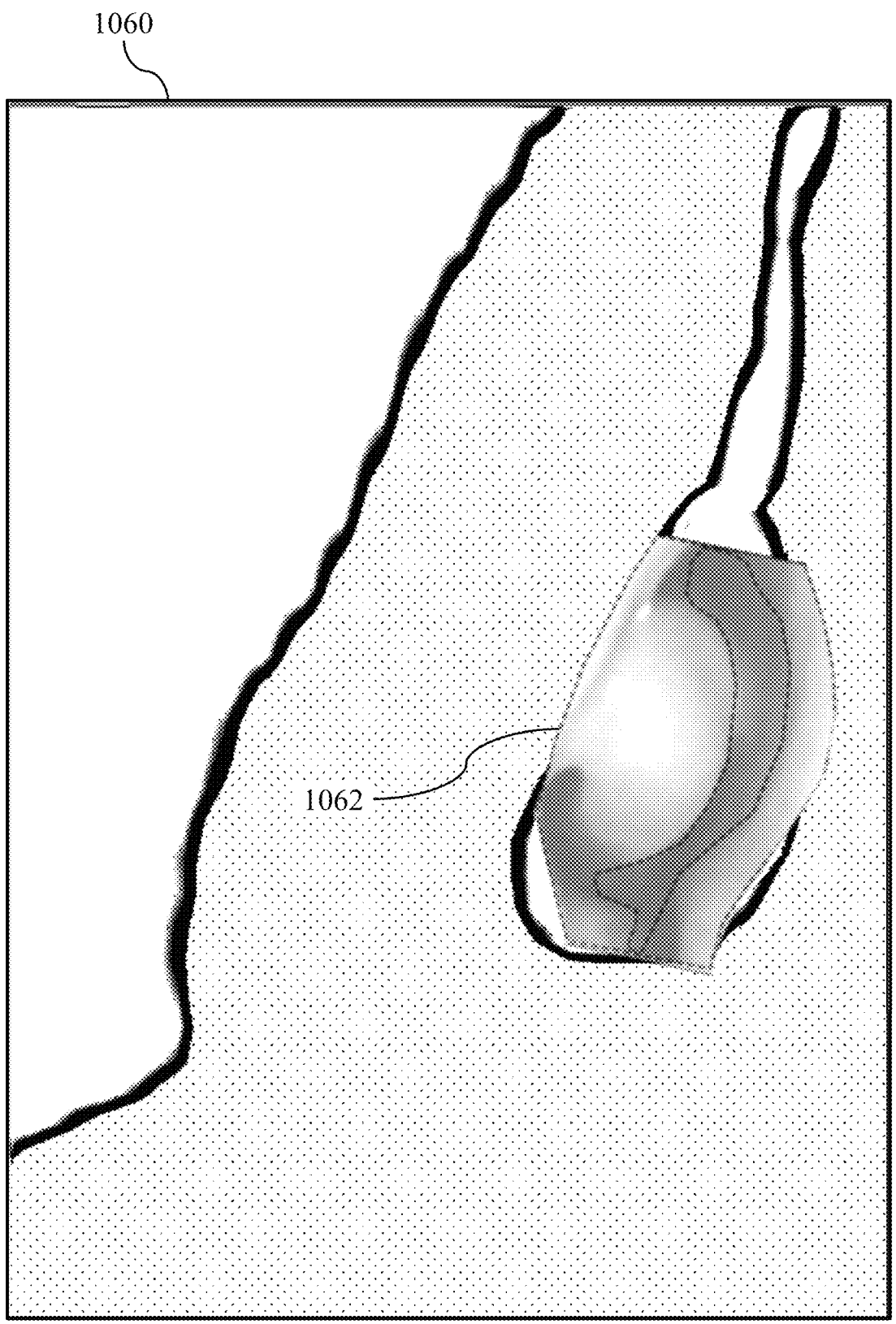
FIG. 26D is a screenshot of an exemplary interface for displaying a hybrid image that combines features of a segmented endoscopic image and 3D image data.

FIGS. 26B-26D show examples of interfaces that may be displayed during the performance of steps such as those illustrated in FIG. 26A. FIG. 26B shows an endoscopic image (1052) of the nasal valve prior to segmentation. FIG. 26C shows an endoscopic image (1054) similar to that shown in FIG. 26B after segmentation, with the segmentation boundaries (1056, 1058) being illustrated as dotted lines. FIG. 26D shows a correlated portion of 3D image data (1060) that has been identified as a match for the endoscopic image (1054), and that includes an overlay of the segmented endoscopic image (1062) at the corresponding location within the 3D image data.

Figure 27:
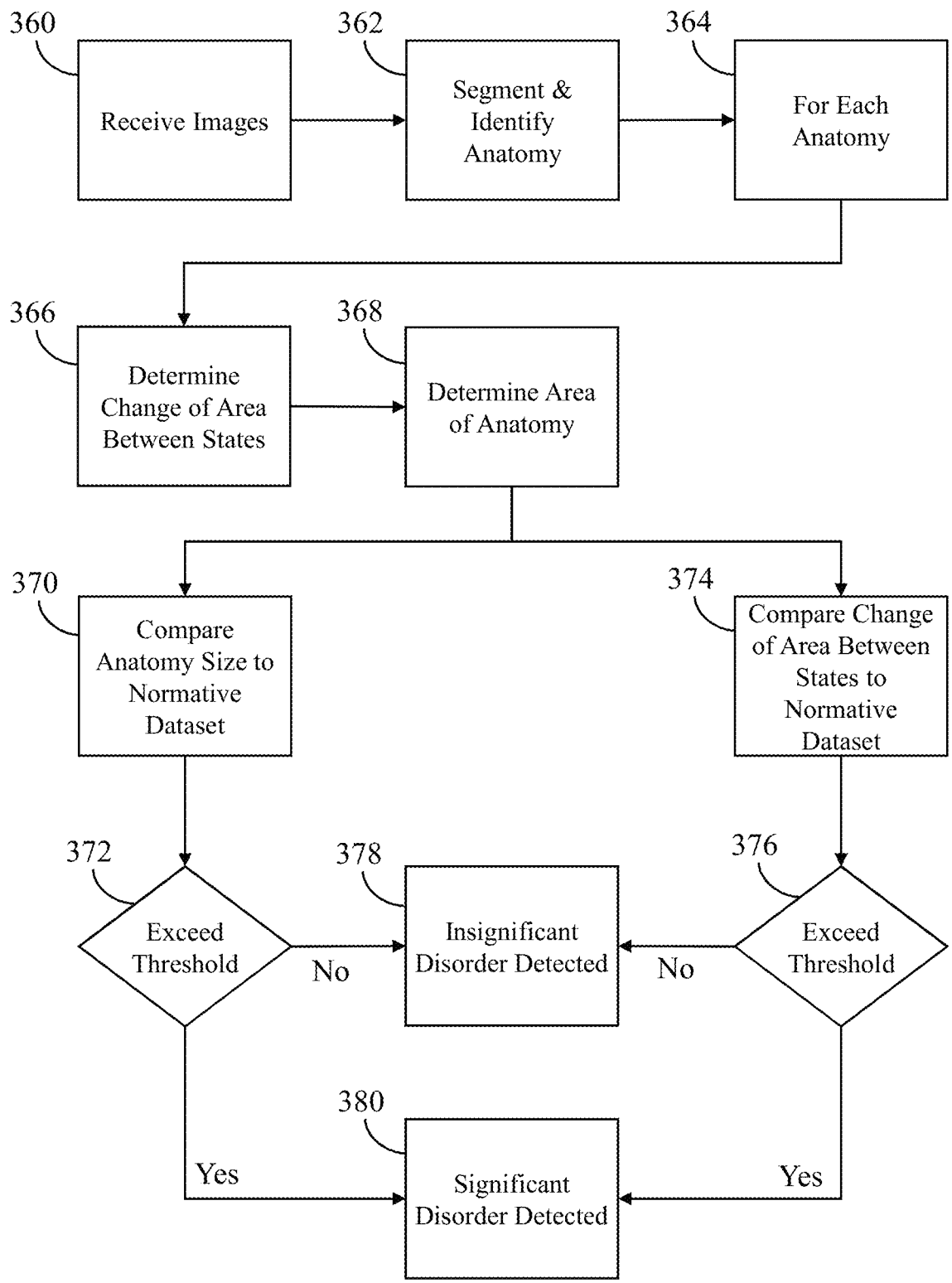
FIG. 27 is a flowchart of an exemplary set of steps that may be performed with the system of FIG. 3 to identify sleep apnea disorder.

While several examples have been provided illustrating the use of the disclosed technology to provide varying analysis of nasal valve obstruction and other conditions, additional examples exist and will be apparent to those skilled in the art in light of this disclosure. As an example, FIG. 27 shows a set of steps that are based in part on the steps of FIG. 4, and that may be performed with the system of FIG. 3 to identify sleep apnea. As with other disclosed features, the system initially receives (360) a set of images of patient anatomy, which may include still images, video sequences, or both. As images are received (360), they may be segmented and depicted anatomy may be automatically identified (362), as has been described above. Segmentation may include depth or volume segmentation, segmentation based on discrete anatomy, or segmentation by detected tissue types, for example. As anatomy is identified (362), the system may prompt the user (e.g., via the imaging device (218)) to capture additional images of particular anatomy until a complete set of images are received (360). The list of required anatomy may be pre-configured, and may include, for example, depictions of anatomical structures such as the soft palate, walls, tongue, and other pre-defined anatomy. As the required anatomy are identified (362) the system may provide an indication to the user that the required anatomy has been imaged. Imaging guidance may also include prompting the user to capture images of the required anatomy during both a relaxed state and an inhalation or other state, as has been previously described.

Once images of the required anatomical structures and their states have been received and identified (362), the system will, for each identified anatomical structure (364) (e.g., separately for the soft palate, lateral walls, and tongue), determine (366) the change in cross sectional area of the airway between the maximal and minimal states, as has been previously described, and determine (368) the cross sectional area of the anatomical structure itself (e.g., excluding the airway and surrounding tissues). The system may then compare (370) the cross sectional area or size of each anatomical structure to a normative anatomical structure size or area dataset and, where the patient anatomy size exceeds (372) the normative data size by a configured threshold, the system may indicate (380) that significant sleep apnea disorder has been detected, and may additionally suggest additional treatment options, provide historical comparisons, and provide other comparisons, as has been previously described. The system may also compare (374) the change in cross sectional area between image states (e.g., between the maximal and minimal airway area) and, where the difference exceeds (376) a configured threshold, may indicate (380) that significant sleep apnea disorder has been detected.

Where either comparison (370, 374) does not exceed a corresponding configured threshold (372, 376), the system may indicate (378) that there is insignificant disorder detected. Varying implementations of the system may perform one or both comparisons (370, 374), and may provide individualized or aggregate indications of whether a disorder exists based thereon. For example, in some implementations the system may separately provide the results of comparisons, indicating that one metric indicates disorder, while a separate metric indicates no significant disorder. As another example, the system may provide a blended or aggregate indication based on both comparisons as well as the extent to which a configured threshold is exceeded (e.g., where one comparison indicates no significant disorder, and the configured threshold for the other comparison is greatly exceeded, the system may indicate a very high likelihood of disorder despite the mixed results).

Figure 28:
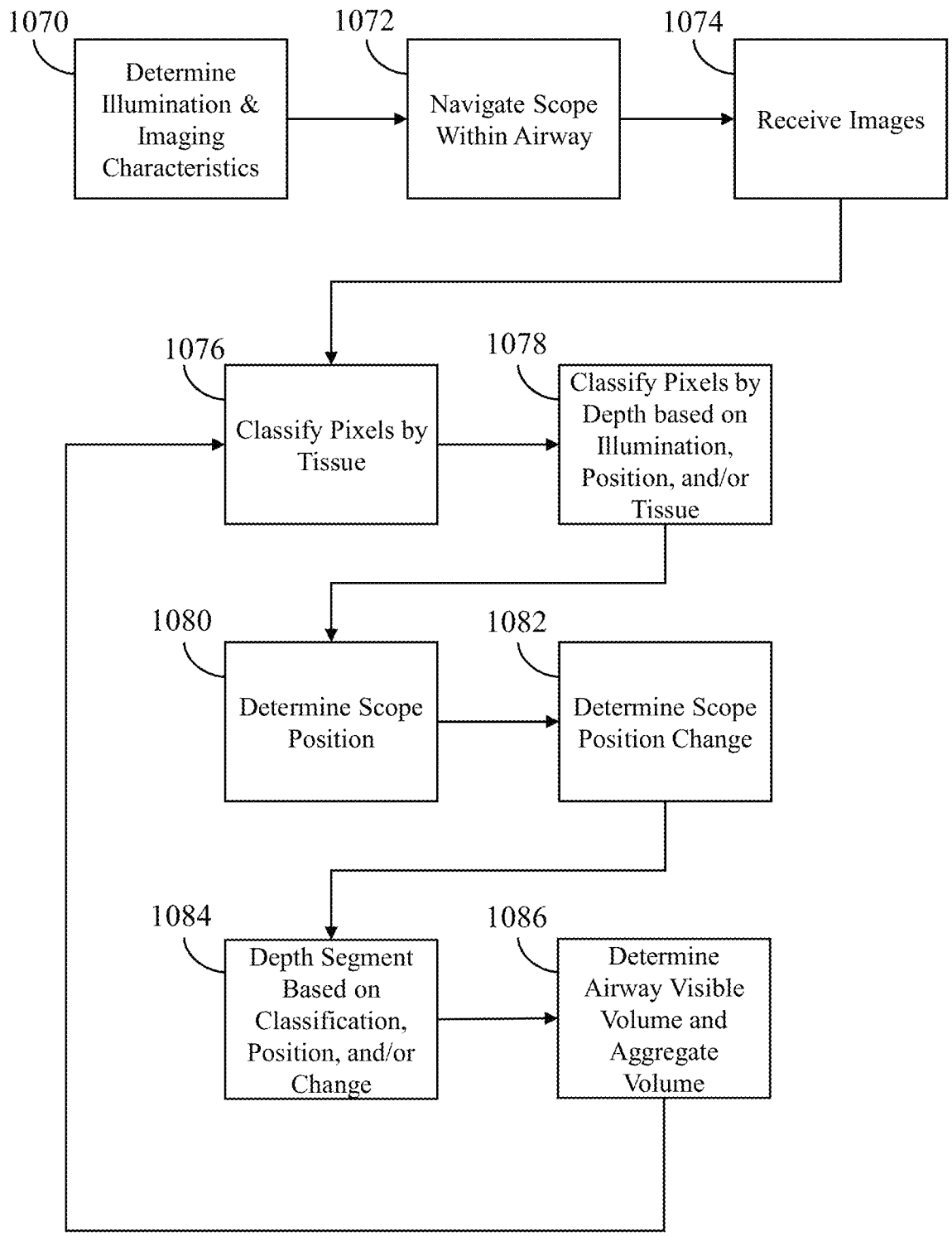
FIG. 28 is a flowchart of an exemplary set of steps that may be performed with the system of FIG. 3 to determine the volume of an airway based upon per-pixel illumination classification.

FIG. 28 shows a set of steps that may be performed with varying implementations of the disclosed technology in order to determine the volume of an imaged airway based upon a per-pixel or per-pixel group classification of illumination. The steps of FIG. 28 may be performed in addition to, or in the alternative to, other disclosed steps and features that provide depth sensing or volumetric analysis (e.g., such as those described in the context of FIGS. 10 through 12B). The system may determine (1070) the illumination and imaging characteristics of the endoscope that is being used (e.g., such as the endoscope (212)). This may include, for example, determining the capabilities of the endoscope's distally mounted LED illuminators and camera based upon the scope's serial number or other identifying information, may include determining user configured settings that influence the operation of the LED illuminator and camera (e.g., by querying a memory of the device where such settings are stored), and/or may include overriding other configurations of the device to cause the LED illuminators and camera to operate at pre-configured settings that are selected for depth and volume analysis. The steps of FIG. 28 may be performed with a camera or a dedicated light sensor, or both, as some of the disclosed steps do not require determination of the actual pixel color, and only require the magnitude of reflected light.

As an example, this may include forcing the LED illuminators to operate at a pre-defined power input or lumen output, forcing certain illuminators within a set to be enabled or disabled (e.g., illuminators having a substantially similar optical axis as the camera may remain enabled, while ambient illuminators may be disabled), forcing the camera to operate at a pre-defined resolution (e.g., a camera capable of 4K imaging may instead be operated at 1080p or lower resolution, in order to reduce the number of pixels requiring subsequent classification while still maintaining adequate precision of results), and/or forcing the camera to operate at a pre-defined framerate or shutter speed (e.g., a camera capable of 120 fps may instead be operated at 30 fps or lower to reduce the number of input images, or may be operated at a reduced shutter speed in order to increase pixel illumination and per-pixel contrast).

A user may then navigate (1072) the endoscope within a patient's airway (e.g., nose, throat) while receiving (1074) video and/or images captured by the scope, as has been previously described. For each received (1074) image, or for certain sequences of received (1074) images, the system may then perform per-image, per-pixel, and/or per-pixel grouping based classifications of depth in order to determine a depicted volume.

Steps performed during this classification may include classifying (1076) each pixel and/or pixel grouping based upon tissue type, which may be performed using an artificial intelligence or machine learning process that has been configured or trained with annotated anatomical images to identify a type of tissue associated with each pixel based upon visual characteristics such as color and position relative to other tissue types. The system may also classify (1078) each pixel and/or pixel grouping by depth based upon the level of illumination and, in some implementations, the tissue type of that pixel or group. For example, given a known illumination source (e.g., one or more LED illuminators with a determined (1070) magnitude of illumination output), specific tissue types known to be present in the nose will have predictable levels of illumination or reflection of projected light at varying distances of projection.

Figure 29A:
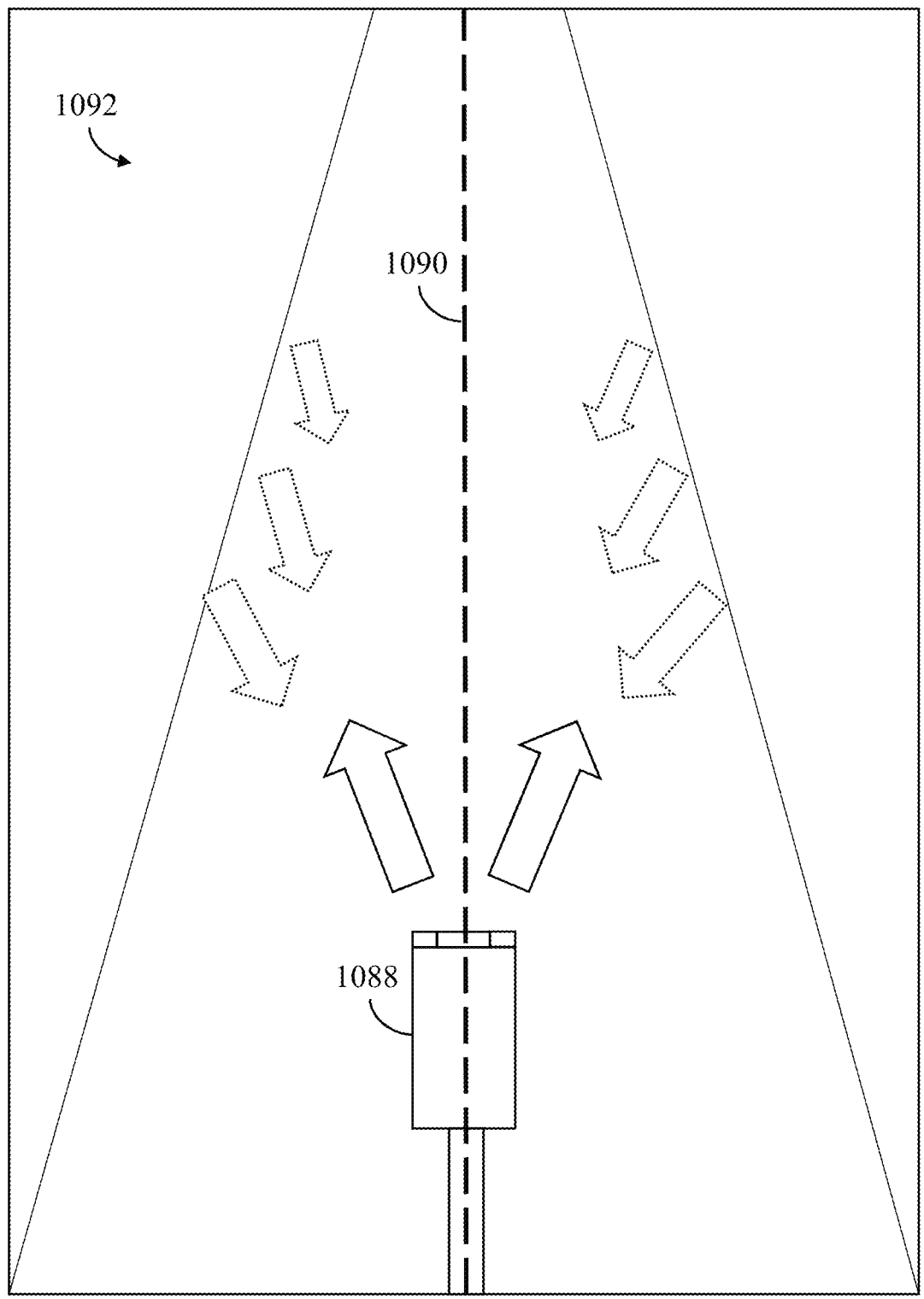
FIG. 29A is a schematic diagram illustrating aspects of illumination based classification of pixels.

As a more specific example, FIG. 29A illustrates the relationship between depth and illumination. An endoscope (1088) having light illuminators and a camera or light sensor is positioned within an airway such as the nasal canal. Anatomical structures (1092) within the airway are similar to the portions of the nasal valve (108, 110) illustrated in FIG. 1C, and decrease in cross sectional area/volume the further they progress into the nasal airway. An optical axis (1090) of the endoscope (1088) is represented as a dashed line, and a pair of solid-line arrows represent the generalized direction in which illuminators of the endoscope (1088) project light during use. A set of dashed-line arrows positioned along the anatomical structures (1092) represent generalized locations from which projected light might reflect, and a generalized direction in which a portion of that light might reflect and be sensed by the camera or light sensor of the endoscope (1088).

In a scenario such as that depicted, the reflective surface of the anatomical structure (1092) will have generally the same tissue composition, resulting in a predictable per-pixel tissue classification of a resulting 2D image. Thus, variances in the sensed reflected light per-pixel will be entirely or substantially due to two factors: (i) offset from the optical axis (1090) of the pixel in question (e.g., where the optical axis is equivalent to the z-axis, both x-axis offset and y-axis offset), and (ii) the depth or distance from the endoscope (1088) and the point on the anatomical structure that the pixel in question corresponds to (e.g., as described by the Inverse Square Law, the magnitude of light reflected from a surface is dependent upon the distance that the light travels before striking the surface).

Figure 29B:
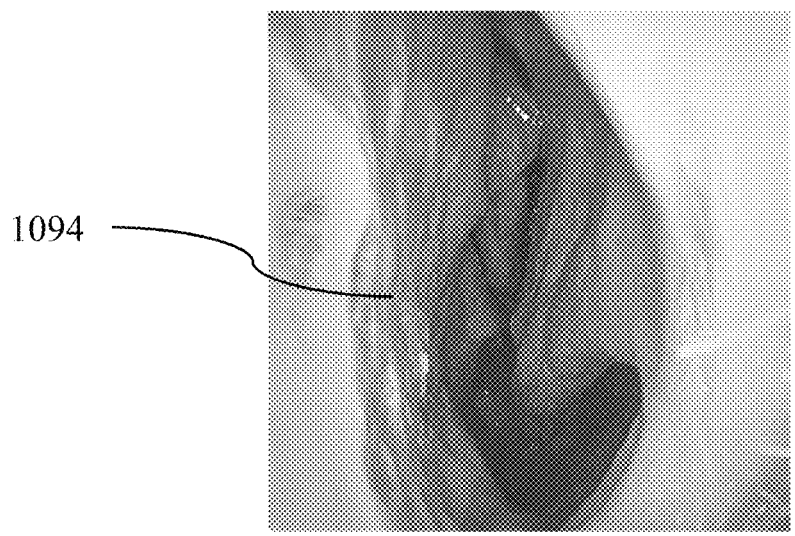
FIG. 29B is a picture of anatomical structures within an airway such as may be captured during the steps of FIG. 28.
Figure 29C:
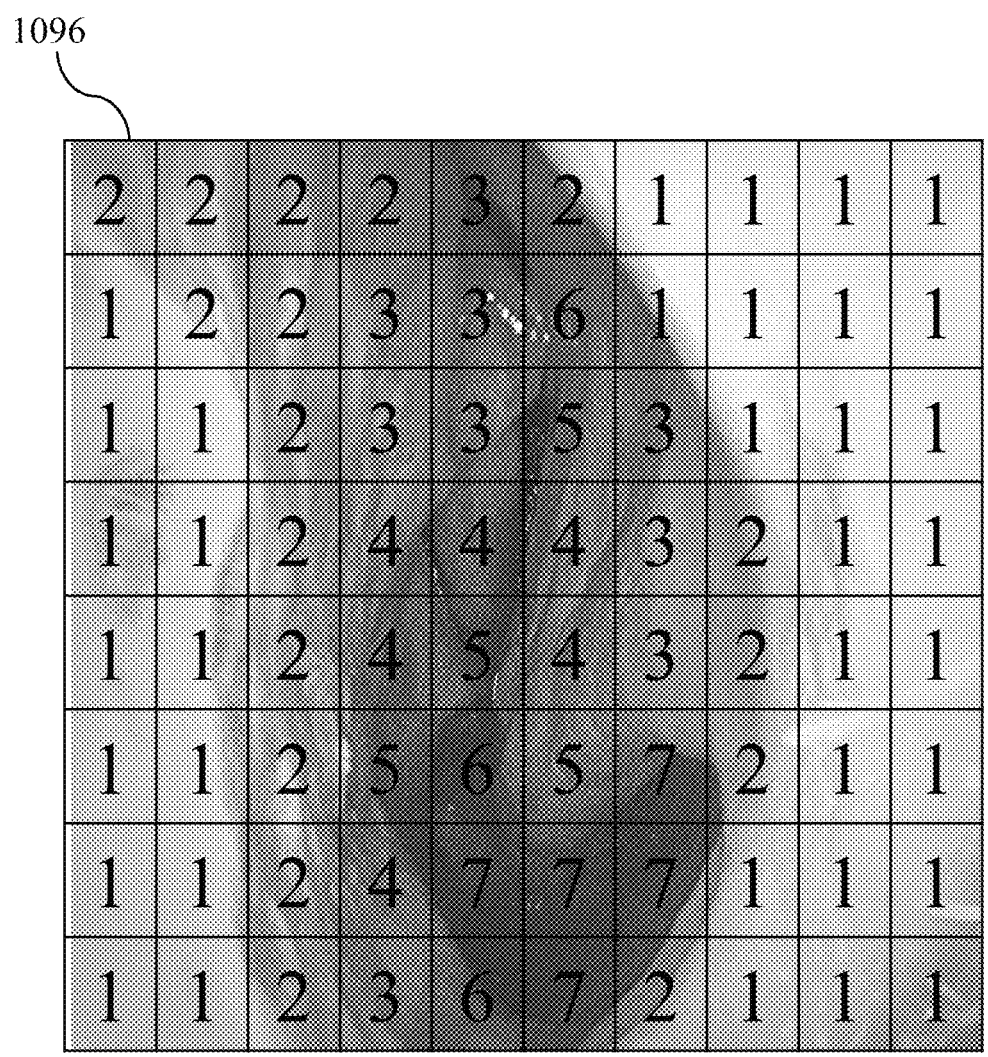
FIG. 29C is a schematic diagram showing the picture of 29B with an overlaid numerical depth map that illustrates the correspondence between brightness and depth.
Figure 29D:
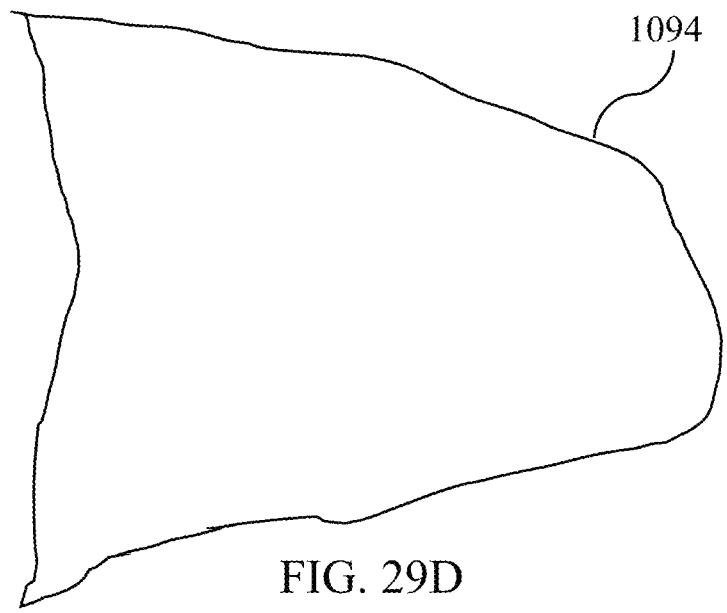
FIG. 29D is a simulated side profile view of an anatomical structure from the picture of FIG. 29B.
Figure 29E:
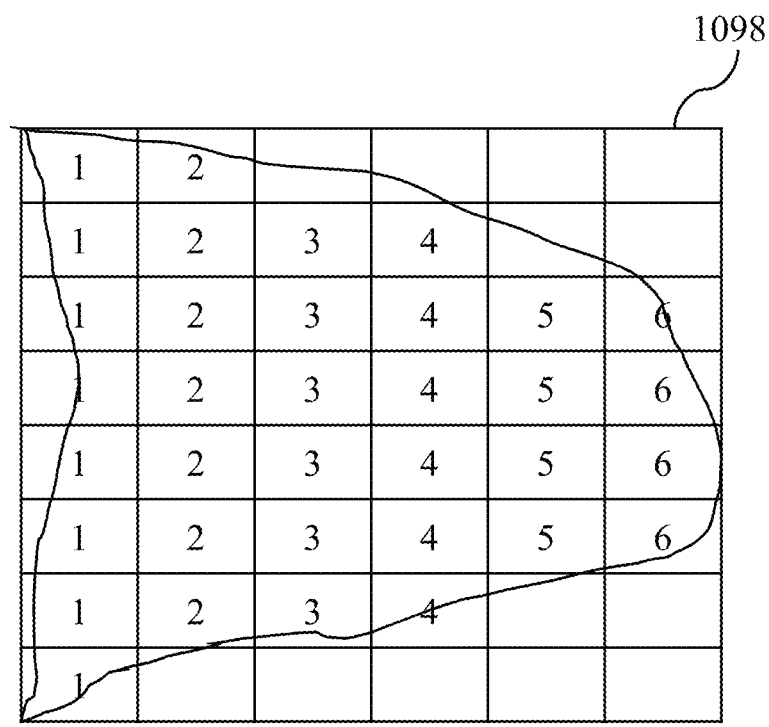
FIG. 29E is the simulated view of FIG. 29D with an overlaid numerical depth map that illustrates the correspondence between brightness and depth.

Thus, by configuring the image classification process (e.g., such as by training a machine learning process, or configuring another pattern identifying process) to account for tissue classification and optical axis offset, expected brightness values at varying depths can be determined across a wide range of scenarios. FIGS. 29B through 29E provide additional examples and illustrations of the above. FIG. 29B is an image captured within the nasal canal, while FIG. 29C shows the same image with a numerical depth map overlay such as might be produced by performing steps such as those shown in FIG. 28. Such a depth map (1096) might be utilized by the system to determine (1086) and display depth and volume information, as will be described in more detail below. FIG. 29D shows a simulated side view of an anatomical structure (1094) depicted in FIGS. 29B and 29C. FIG. 29E shows the simulated view of FIG. 29D with a depth map (1098), such as might be overlaid upon the anatomy (1094) when viewed from a typical endoscope, rotated and overlaid to illustrate the correspondence between depth and brightness.

Returning to FIG. 28, the system may also determine (1080) a position of the endoscope as part of the volume analysis, which may include determining (1080) a relative position of the endoscope (e.g., within the scope of the interior of an imaged airway) based on imaging, or determining a true position of the endoscope based on additional output from a location sensor (e.g., within a three-dimensional coordinate system of an image guided surgical (IGS) navigation system, as may be indicated by a tri-axis location sensor at the endoscope tip, for example), or both. While true position determination may be performed fairly simply based upon the IGS coordinate system, determining a relative position is not as simple. Immediate relative position may be determined as a function of the depth determination (1078) for some or all of the depth classified pixels depicted in a presently captured image.

This information for an immediate image may be combined with information from prior and/or subsequent images, and a determination (1082) of the scope position change between prior and/or subsequent images, in order determine the scopes position in a more meaningful way. For example, a relative position of the scope based on a single image is somewhat limited and only indicates the distance of the scope from the anatomy depicted from that particular orientation. However, where the relative position of the scope is known for a sequence of images, the depth classification of pixels can be correlated between two or more images captured from different orientations, and a depth-mapping can be developed that is not dependent on any single image or orientation. In this manner, the scope may be navigated throughout the airway (e.g., advancing, retracting, and rotating around other axes), with a relative position of the scope being determined in each singular image, and a plurality of images and corresponding depth mappings being combined together (e.g., based on phase correlation or other digital stitching techniques) to produce a full depth mapping of the anatomy.

Determination of the scope position change (1082) may be based entirely on image analysis and digital stitching techniques, and may also be based on one or more of sensor data from an IGS navigation tracking system, or sensor data from an accelerometer or motion sensor of the endoscope, or other sensor data.

The system may also depth segment (1084) the depth classified pixels of the image to produce a segmented depth map where pixels having the same or similar depth classification are grouped into segments at varying depths. This segmentation may be true to the classified pixel depth, or may organize the pixels into segmentation bands, as may be desirable for a particular implementation. For example, in a banded segmentation, the image may be depth segmented to the nearest millimeter (e.g., pixels at 1.1 mm and 1.3 mm would be segmented into a 1 mm depth band, while pixels at 1.5 mm, 1.8 mm, and 1.9 mm would be segmented into a 2 mm depth band), or half-millimeter, or other configured measurement based upon the desired level of resolution of the resulting segmented depth map. This segmentation may also be based upon the scopes determined position and/or change in position, as has been described (e.g., to produce a depth map not dependent on a singular image), but may also be influenced by position as a correction metric for depth classification and/or resulting segmentation. For example, where IGS navigation tracking, accelerometer and gyroscopic tracking, or other sensor feedback indicates a movement between images that disagrees with a corresponding depth mapping or digital stitching, the potentially erroneous data may be discarded or adjusted. As an example, where digital stitching between two images suggests that the scope advanced 4 mm into the airway, but IGS navigation data indicates that the scope actually advanced 6 mm into the airway between the two images, the erroneous frame may be discarded, re-factored based on the IGS data (e.g., taking 6 mm as the true change in position), or refactored based in-part on the IGS data (e.g., compromising with 5 mm as the change in position).

Finally, the system may determine (1086) and display one or more of the received (1074) image, a visualization of pixel tissue classification, a visualization of pixel depth classification, a visualization of depth segmentation (1084), or an aggregate depth map produced from multiple received (1074) images, via the imaging device (218) or another display, as has been described. The determined (1086) and displayed results may be for only the visible airway (e.g., that depicted in the immediately captured image) or the aggregate airway (e.g., the entire depth mapped space which the scope has navigated through), and may additionally be displayed numerically or in other ways (e.g., a volume in cubic millimeters or centimeters, a deviance from expected volume). Additionally, as has been described above, the determined (1086) volume may be provided in isolation, or in the context of one or more other volume determinations (e.g., a change between a maximum volume and minimum volume state, a change between pre-procedure and post-procedure, and other examples).

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

The invention claimed is:

1. A system for endoscopic imaging comprising:
  (a) an endoscope configured to capture images;
  (b) a display;
  (c) a user input device; and
  (d) a processor configured to:
    (i) determine an imaging mode, wherein the imaging mode is associated with an anatomical feature;
    (ii) receive one or more images from the endoscope;
    (iii) execute an object recognition process to identify the anatomical feature within the one or more images;
    (iv) determine at least one characteristic of the anatomical feature based upon the one or more images;
    (v) display the at least one characteristic via the display;
  wherein the processor is further configured to, when executing the object recognition process on an input image to identify anatomical features:
  (i) display the input image via the display;
  (ii) perform a first analysis of the input image to identify a position of a target anatomical feature depicted in the input image;
  (iii) where the target anatomical feature cannot be identified by the first analysis, receive a set of partial user inputs via the user input device and perform a second analysis of the input image based on the set of partial user inputs to identify the position of the target anatomical feature; and
  (iv) overlay a visual boundary on the position of the target anatomical feature on the display;
  wherein the anatomical feature is a turbinate, and wherein the processor is further configured to, when determining the at least one characteristic of the turbinate:
  (i) determine a first area measurement based upon a portion of an image contained within a first overlaid visual boundary that surrounds an identified turbinate;
  (ii) determine a second area measurement based upon a portion of the image contained within a second overlaid visual boundary that surrounds an identified reference anatomy that is proximate to the identified turbinate; and
  (iii) where a difference between the first area measurement and the second area measurement exceeds a configured threshold, determine the at least one characteristic as inflammation of the turbinate.

2. The system of claim 1, wherein:
  (a) the first analysis uses an artificial intelligence process, and is based on the input image and a training dataset of previously captured images; and
  (b) the second analysis uses the artificial intelligence process, and is based on the input image, the training dataset of previously captured images, and the set of partial user inputs.

3. The system of claim 2, wherein the set of partial user inputs comprises a sequence of inputs along part of an edge of the anatomical feature.

4. The system of claim 2, wherein the processor is further configured to modify the appearance of the input image to increase a visual contrast between the target anatomical feature and any other anatomy prior to receiving the set of partial user inputs.

5. The system of claim 1, wherein the processor is further configured to, after overlaying the visual boundary on the position of the target anatomical feature:
  (a) receive a set of modification inputs via the user input device, wherein the set of modification inputs are associated with a portion of the visual boundary and include a new position in the input image for the portion of the visual boundary; and
  (b) overlay an updated visual boundary on the display based on the set of modification inputs.

6. The system of claim 1, wherein the processor is further configured to, when determining the at least one characteristic of the anatomical feature:
  (a) determine one or more area measurements based upon portions of the one or more images contained within one or more overlaid visual boundaries; and
  (b) determine the at least one characteristic based upon the anatomical feature and the one or more area measurements.

7. The system of claim 6, wherein the area measurements describe a number of pixels contained within the one or more overlaid visual boundaries.

8. The system of claim 1, wherein the processor is configured to display a set of imaging mode options via the display, and determine the imaging mode based upon a user selection from the set of imaging mode options.

9. The system of claim 1, further comprising a touchscreen display that includes the display and the user input device.

10. A method comprising:
  (a) by a processor, determining an imaging mode, wherein the imaging mode is associated with an anatomical feature;
  (b) by the processor, receiving one or more images from an endoscope;
  (c) by the processor, executing an object recognition process to identify the anatomical feature within the one or more images;
  (d) by the processor, determining at least one characteristic of the anatomical feature based upon the one or more images;
  (e) by the processor, displaying the at least one characteristic via a touchscreen display;
  the method further comprising, when executing the object recognition process on an input image to identify anatomical features:
  displaying the input image via the touchscreen display;
  (ii) performing a first analysis of the input image to identify a position of a target anatomical feature depicted in the input image;
  (iii) where the target anatomical feature cannot be identified by the first analysis, receiving a set of partial user inputs via the touchscreen display and performing a second analysis of the input image based on the set of partial user inputs to identify the position of the target anatomical feature; and (iv) overlaying a visual boundary on the position of the target anatomical feature on the touchscreen display;

the method further comprising, wherein the anatomical feature is a turbinate, and wherein by the processor, when determining the at least one characteristic of the turbinate:

(i) determining a first area measurement based upon a portion of an image contained within a first overlaid visual boundary that surrounds an identified turbinate;

(ii) determining a second area measurement based upon a portion of the image contained within a second overlaid visual boundary that surrounds an identified reference anatomy that is proximate to the identified turbinate; and (iii) where a difference between the first area measurement and the second area measurement exceeds a configured threshold, determining the at least one characteristic as inflammation of the turbinate.

11. The method of claim 10, wherein:
(a) the first analysis uses an artificial intelligence process, and is based on the input image and a training dataset of previously captured images;
(b) the second analysis uses the artificial intelligence process, and is based on the input image, the training dataset of previously captured images, and the set of partial user inputs; and
(c) the set of partial user inputs comprises a sequence of inputs along part of an edge of the anatomical feature.

12. The method of claim 10, further comprising determining the at least one characteristic of the anatomical feature by:
(a) determining one or more area measurements based upon portions of the one or more images contained within one or more overlaid visual boundaries; and
(b) determining the at least one characteristic based upon the anatomical feature and the one or more area measurements.

13. A system for endoscopic imaging comprising:
(a) an endoscope configured to capture images;
(b) a display;
(c) a user input device; and
(d) a processor configured to:
(i) determine an imaging mode, wherein the imaging mode is associated with an anatomical feature;
(ii) receive one or more images from the endoscope;
(iii) execute an object recognition process to identify the anatomical feature within the one or more images;
(iv) determine at least one characteristic of the anatomical feature based upon the one or more images;
(v) display the at least one characteristic via the display;
wherein the processor is further configured to, when executing the object recognition process on an input image to identify anatomical features:
(i) display the input image via the display;
(ii) perform a first analysis of the input image to identify a position of a target anatomical feature depicted in the input image;
(iii) where the target anatomical feature cannot be identified by the first analysis, receive a set of partial user inputs via the user input device and perform a second analysis of the input image based on the set of partial user inputs to identify the position of the target anatomical feature; and
(iv) overlay a visual boundary on the position of the target anatomical feature on the display;
wherein the processor is further configured to modify the appearance of the input image to increase a visual contrast between the target anatomical feature and any other anatomy prior to receiving the set of partial user inputs, wherein the anatomical feature is a nasal polyp, and wherein the processor is further configured to, when determining the at least one characteristic of the nasal polyp:
(i) determine one or more area measurements based upon one or more portions of an image contained within one or more overlaid visual boundaries that surround nasal polyps;
(ii) where a combined area of the one or more area measurements exceeds a configured threshold, determine the at least one characteristic as obstruction by nasal polyps.

14. A method comprising:
(a) by a processor, determining an imaging mode, wherein the imaging mode is associated with an anatomical feature;
(b) by the processor, receiving one or more images from an endoscope;
(c) by the processor, executing an object recognition process to identify the anatomical feature within the one or more images;
(d) by the processor, determining at least one characteristic of the anatomical feature based upon the one or more images;
(e) by the processor, displaying the at least one characteristic via a touchscreen display;
the method further comprising, when executing the object recognition process on an input image to identify anatomical features:
(i) displaying the input image via the touchscreen display;
(ii) performing a first analysis of the input image to identify a position of a target anatomical feature depicted in the input image;
(iii) where the target anatomical feature cannot be identified by the first analysis, receiving a set of partial user inputs via the touchscreen display and performing a second analysis of the input image based on the set of partial user inputs to identify the position of the target anatomical feature; and
(iv) overlaying a visual boundary on the position of the target anatomical feature on the touchscreen display;
the method further comprising, by the processor, modifying the appearance of the input image to increase a visual contrast between the target anatomical feature and any other anatomy prior to receiving the set of partial user inputs, wherein the anatomical feature is a nasal polyp, and wherein by the processor, when determining the at least one characteristic of the nasal polyp:
(i) determining one or more area measurements based upon one or more portions of an image contained within one or more overlaid visual boundaries that surround nasal polyps;
(ii) where a combined area of the one or more area measurements exceeds a configured threshold, determining the at least one characteristic as obstruction by nasal polyps.

* * * * *